(12) United States Patent
Lingam et al.

(10) Patent No.: US 8,119,647 B2
(45) Date of Patent: Feb. 21, 2012

(54) FUSED PYRIMIDINEONE COMPOUNDS AS TRPV3 MODULATORS

(75) Inventors: Prasada Rao V. S. Lingam, Maharashtra (IN); Sachin Sundarlal Chaudhari, Maharashtra (IN); Abraham Thomas, Maharashtra (IN); Neelima Khairatkar-Joshi, Maharashtra (IN); Vidya Ganapati Kattige, Maharashtra (IN)

(73) Assignee: Glenmark Pharmaceuticals S.A., La Chaux-de-Fonds (CH)

( * ) Notice: Subject to any disclaimer, the term of this patent is extended or adjusted under 35 U.S.C. 154(b) by 272 days.

(21) Appl. No.: 12/421,145

(22) Filed: Apr. 9, 2009

(65) Prior Publication Data

US 2009/0286811 A1 Nov. 19, 2009

Related U.S. Application Data

(60) Provisional application No. 61/057,971, filed on Jun. 2, 2008, provisional application No. 61/074,112, filed on Jun. 19, 2008, provisional application No. 61/092,324, filed on Aug. 27, 2008, provisional application No. 61/113,344, filed on Nov. 11, 2008.

(30) Foreign Application Priority Data

| Apr. 23, 2008 | (IN) | 902/MUM/2008 |
| Jun. 5, 2008 | (IN) | 1201/MUM/2008 |
| Aug. 8, 2008 | (IN) | 1687/MUM/2008 |
| Oct. 10, 2008 | (IN) | 2174/MUM/2008 |

(51) Int. Cl.
*A01N 43/90* (2006.01)
*A01N 43/54* (2006.01)
*A61K 31/519* (2006.01)
*A61K 31/505* (2006.01)
*C07D 491/00* (2006.01)
*C07D 495/00* (2006.01)

(52) U.S. Cl. ............... 514/259.2; 514/267; 544/250; 544/278

(58) Field of Classification Search .................. None
See application file for complete search history.

(56) References Cited

U.S. PATENT DOCUMENTS

| 4,223,031 A | 9/1980 | Covington et al. |
| 4,444,773 A | 4/1984 | Doria et al. |
| 4,551,457 A | 11/1985 | Doria et al. |
| 4,558,046 A | 12/1985 | Doria et al. |
| 4,609,660 A | 9/1986 | Doria et al. |
| 5,703,085 A | 12/1997 | Suzuki et al. |
| 5,804,583 A | 9/1998 | Salimbeni et al. |
| 6,323,208 B1 | 11/2001 | Chenard et al. |
| 6,492,383 B1 | 12/2002 | Munchhof et al. |
| 2006/0040944 A1 | 2/2006 | Gosselin et al. |
| 2006/0052596 A1 | 3/2006 | Muller et al. |
| 2007/0179164 A1 | 8/2007 | Chong et al. |
| 2007/0219222 A1 | 9/2007 | Moran et al. |
| 2007/0249647 A1 | 10/2007 | Vander Jagt et al. |
| 2008/0194616 A1 | 8/2008 | Liu et al. |
| 2009/0176991 A1 | 7/2009 | Murray et al. |

FOREIGN PATENT DOCUMENTS

| WO | WO2007056124 A3 | 5/2007 |
| WO | WO2008094909 | 8/2008 |

OTHER PUBLICATIONS

Dorwald F. A. Side Reactions in Organic Synthesis, 2005, Wiley: VCH, Weinheim p. IX of Preface.*
International Search Report and Written Opinion from International Application No. PCT/IB2009/005290, filed Apr. 15, 2009, mailed on Aug. 20, 2009.
Passarotti, C.M. et al. "In the search for new antiinflammatory drugs: Synthesis and antiinflammatory activity of some Thiazolo (3,2-a) pyrimidine derivatives containing a thioether group" vol. 134, No. 11, Jan. 1, 1995; pp. 639-643.
Djekou, et al., An Efficient Synthesis of new Thiazolopyrimidinones under Microwave Irradiation, journal of heterocyclic chemistry, 43:55, 1225-1229 (2006).

* cited by examiner

*Primary Examiner* — James O Wilson
*Assistant Examiner* — Jeffrey Murray
(74) *Attorney, Agent, or Firm* — Gilman Pergament LLP

(57) ABSTRACT

The present invention provides transient receptor potential vanilloid (TRPV) modulators. In particular, compounds described herein are useful for treating or preventing diseases, conditions and/or disorders modulated by TRPV3. Also provided herein are processes for preparing compounds described herein, intermediates used in their synthesis, pharmaceutical compositions thereof, and methods for treating or preventing diseases, conditions and/or disorders modulated by TRPV3.

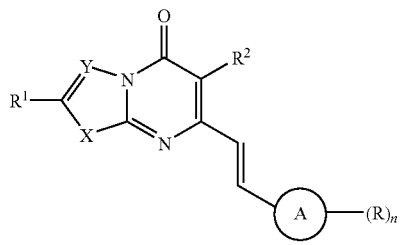

(I)

50 Claims, No Drawings

FUSED PYRIMIDINEONE COMPOUNDS AS TRPV3 MODULATORS

RELATED APPLICATIONS

This application claims the benefit of Indian Provisional Applications Nos. 902/MUM/2008, filed on Apr. 23, 2008, 1201/MUM/2008, filed on Jun. 5, 2008, 1687/MUM/2008, filed on Aug. 8, 2008, and 2174/MUM/2008, filed on Oct. 10, 2008, and U.S. Provisional Applications Nos. 61/057,971, filed on Jun. 2, 2008, 61/074,112, filed on Jun. 19, 2008, 61/092,324, filed on Aug. 27, 2008, and 61/113,344, filed on Nov. 11, 2008, all of which are hereby incorporated by reference in their entirety.

TECHNICAL FIELD

The present patent application relates to fused 'pyrimidineone' compounds with Transient Receptor Potential Vanilloid 3 (TRPV3) activity.

BACKGROUND

Movement of ions across cellular membranes is carried out by specialized proteins. TRP channels are one large family of non-selective cation channels that function to help regulate ion flux and membrane potential. TRP channels are subdivided into 6 sub-families including the TRPV family. TRPV3 is a member of the TRPV class of TRP channels.

TRPV3 is a calcium permeable nonselective cation channel. In addition to calcium ions, TRPV3 channels are permeable to other cations, for example sodium. Thus, TRPV3 channels modulate membrane potential by modulating the flux of cations such as calcium and sodium ions. TRPV3 receptors are mechanistically distinct from voltage-gated calcium channels. Generally, voltage-gated calcium channels respond to membrane depolarization and open to permit an influx of calcium from the extracellular medium that result in an increase in intracellular calcium levels or concentrations. In contrast, TRP channels which are non-selective, long lasting, produce more prolonged changes in ion concentration and are ligand gated (modulated by chemicals such as 2-aminoethoxydiphenyl borate [2-APB], vanilloids and heat). These mechanistic differences are accompanied by structural differences among voltage-gated and TRP channels. Thus, although many diverse channels act to regulate ion flux and membrane potential in various cell types and in response to numerous stimuli, it is important to recognize the significant structural, functional, and mechanistic differences among different classes of ion channels.

TRPV3 proteins are thermosensitive channels expressed in skin cells (Peier et al. *Science* (2002), 296, 2046-2049) and dorsal root ganglion, trigeminal ganglion, spinal cord and brain (Xu et al. *Nature* (2002), 418, 181-185; Smith et al. *Nature* (2002), 418, 186-188). In a keratinocyte cell line, stimulation of TRPV3 leads to release of inflammatory mediators including interleukin-1. Thus TRPV3 may also play an important role in regulating inflammation and pain that results from the release of inflammatory stimuli. Particular TRPV3 proteins that may be used in screening assays, as described herein, to identity compounds that modulate a function of TRPV3 include, but are not limited to human TRPV3, mouse TRPV3, rat TRPV3 and Drosophila TRPV3. US2004/0009537 (the '537 application) disclosed sequences corresponding to human, mouse, and Drosophila TRPV3. For example, SEQ ID Nos 106 and 107 of the '537 application correspond to the human nucleic acid and amino acid sequences, respectively. SEQ ID Nos 108 and 109 of the '537 application correspond to the mouse nucleic acid and amino acid sequences, respectively.

TRPV3 function has been basically implicated in the reception and transduction of pain. Accordingly, it would be desirable to identify and make compounds that can modulate one or more functions of TRPV3.

WO 2007/056124, WO 2008/140750 and WO 2008/033564 disclose TRPV3 modulators, in particular antagonists, for treatment of various diseases mediated TRPV3.

In efforts to discover better analgesics, there still exists a need for therapeutic treatment of diseases, conditions and/or disorders modulated by TRPV3.

SUMMARY

The present patent application relates to compounds of the formula (I):

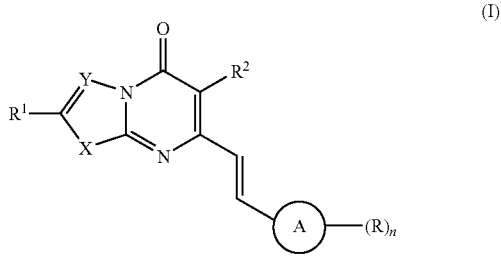

wherein X is O, S, or $NR^b$;

Y is $CR^3$ or N;

ring A is aryl, heterocyclyl or heteroaryl;

at each occurrence, R, which may be the same or different, is selected from hydrogen, nitro, cyano, halogen, $-OR^a$, substituted or unsubstituted alkyl, alkenyl, haloalkyl, cyanoalkyl, cyanoalkyloxy, cycloalkyl, aryl, heteroaryl or heterocyclic group;

$R^1$ and $R^3$, which may be the same or different, are each independently selected from hydrogen, halogen, nitro, cyano, —COOH, substituted or unsubstituted alkyl, alkenyl, alkynyl, haloalkyl, cycloalkyl, cycloalkenyl, aryl, heteroaryl, heterocyclic group, $-NR^4R^5$, $-S(O)_pNR^4R^5$, or $-S(O)_pR^4$; or $R^1$ and $R^3$ together with the carbon atoms to which they were attached may form a 5 to 7 membered cyclic ring, which may be substituted or unsubstituted, saturated, unsaturated or partially saturated, which cyclic ring may optionally contain one or more heteroatoms selected from O, $NR^b$ or S;

$R^2$ is aryl, heteroaryl, or heterocyclic group, each of which may be optionally mono- or polysubstituted with substituent(s) independently selected from the group consisting of halogen, hydroxyl, nitro, cyano, —COOH, $-NR^4R^5$, acyl, substituted or unsubstituted alkyl, alkenyl, alkoxy, cyanoalkoxy, haloalkyl, haloalkyloxy, cycloalkyl, cycloalkylalkyl, cycloalkylalkoxy, aryl, heterocyclic group, and heteroaryl;

at each occurrence, $R^a$, which may be the same or different, is selected from the group consisting of hydrogen, substituted or unsubstituted alkyl, haloalkyl, cyanoalkyl, alkenyl, cycloalkyl, alkoxyalkyl, aryl, heteroaryl, heterocyclic group, cycloalkylalkyl, arylalkyl, heteroarylalkyl, or heterocyclylalkyl;

at each occurrence, $R^b$ is selected from hydrogen, substituted or unsubstituted alkyl, or arylalkyl;

at each occurrence of $R^4$ and $R^5$, which may be the same or different, are independently selected from hydrogen, substituted or unsubstituted alkyl, alkenyl, cycloalkyl, cycloalkylalkyl, cycloalkenyl, aryl, arylalkyl, heteroaryl, heteroarylalkyl, heterocyclic group, or heterocyclylalkyl;

'n' is an integer ranging from 0 to 5, inclusive; and

'p' is an integer ranging from 0 to 2, inclusive.

It should be understood that the formula (I) structurally encompasses all geometrical isomers, stereoisomers, including enantiomers and diastereomers, and pharmaceutically acceptable salts that may be contemplated from the chemical structure of the genus described herein.

According to one embodiment, specifically provided are compounds of the formula (I) in which X is S.

According to another embodiment, specifically provided are compounds of the formula (I) in which X is $NR^b$, where $R^b$ is hydrogen or alkyl, such as methyl.

According to another embodiment, specifically provided are compounds of the formula (I) in which Y is $CR^3$, where $R^3$ is hydrogen, halogen, alkyl or haloalkyl.

According to another embodiment, specifically provided are compounds of the formula (I) in which $R^1$ is hydrogen, halogen, or alkyl.

According to another embodiment, specifically provided are compounds of the formula (I) in which $R^2$ is substituted or unsubstituted aryl, preferably phenyl.

According to another embodiment, specifically provided are compounds of the formula (I) in which $R^2$ is substituted or unsubstituted heteroaryl. In this embodiment $R^2$ is substituted or unsubstituted pyridyl, wherein substituent(s) is halogen, such as F or Cl.

According to another embodiment, specifically provided are compounds of the formula (I) in which ring A is aryl.

According to another embodiment, specifically provided are compounds of the formula (I) in which ring A is heteroaryl. In this embodiment ring A is pyridine.

According to one embodiment, there is provided a compound of formula (II)

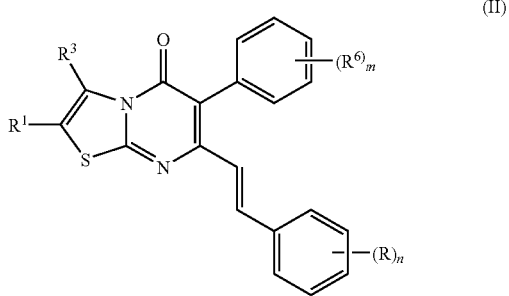

(II)

wherein at each occurrence R, which may be the same or different, is selected from hydrogen, nitro, cyano, halogen, —$OR^a$, substituted or unsubstituted alkyl, alkenyl, haloalkyl, cyanoalkyl, cyanoalkyloxy, cycloalkyl, aryl, heteroaryl, or heterocyclic group;

$R^1$ and $R^3$, which may be the same or different, are each independently selected from hydrogen, halogen, nitro, cyano, —COOH, substituted or unsubstituted alkyl, alkenyl, alkynyl, haloalkyl, haloalkyl, cycloalkyl, cycloalkenyl, aryl, heteroaryl, heterocyclic group, —$NR^4R^5$, —$S(O)_pNR^4R^5$, or —$S(O)_pR^4$; or $R^1$ and $R^3$ together with the carbon atoms to which they were attached may form a 5 to 7 membered cyclic ring, which may be substituted or unsubstituted, saturated, unsaturated or partially saturated, which cyclic ring may optionally contain one or more heteroatoms selected from O, $NR^b$ or S;

at each occurrence, $R^a$, which may be the same or different, is selected from the group consisting of hydrogen, substituted or unsubstituted alkyl, haloalkyl, cyanoalkyl, alkenyl, cycloalkyl, alkoxyalkyl, aryl, heteroaryl, heterocyclic group, cycloalkylalkyl, arylalkyl, heteroarylalkyl, or heterocyclylalkyl;

at each occurrence, $R^b$ is selected from hydrogen, substituted or unsubstituted alkyl, or arylalkyl;

at each occurrence, $R^4$ and $R^5$, which may be the same or different, are independently hydrogen, substituted or unsubstituted alkyl, alkenyl, cycloalkyl, cycloalkylalkyl, cycloalkenyl, aryl, arylalkyl, heteroaryl, heteroarylalkyl, heterocyclic group, or heterocyclylalkyl;

at each occurrence, $R^6$, which may be the same or different, is independently selected from halogen, hydroxyl, nitro, cyano, —COOH, —$NR^4R^5$, acyl, substituted or unsubstituted alkyl, alkenyl, alkoxy, cyanoalkoxy, haloalkyl, haloalkyloxy, cycloalkyl, cycloalkylalkyl, cycloalkylalkoxy, aryl, heterocyclic group, or heteroaryl;

'm' is an integer ranging from 0 to 3, inclusive;

'n' is an integer ranging from 0 to 5, inclusive; and

'p' is an integer ranging from 0 to 2, inclusive.

It should be understood that the formula (II) structurally encompasses all geometrical isomers, stereoisomers, including enantiomers and diastereomers, and pharmaceutically acceptable salts that may be contemplated from the chemical structure of the genus described herein.

According to one embodiment, specifically provided are compounds of the formula (II) in which both $R^1$ and $R^3$ are hydrogen.

According to another embodiment, specifically provided are compounds of the formula (II) in which $R^1$ and $R^3$ are independently hydrogen, halogen (for eg., F or Cl), substituted or unsubstituted alkyl (for eg., methyl), or haloalkyl (for eg., trifluoromethyl).

According to another embodiment, specifically provided are compounds of the formula (II) in which $R^6$ is halogen (for eg., F or Cl), hydroxyl, cyano, acyl (for eg., —C(O)CH$_3$), substituted or unsubstituted alkyl (for eg., t-butyl), substituted or unsubstituted alkoxy (for eg., methoxy or ethoxy), haloalkyl (for eg., trifluoromethyl), haloalkoxy (for eg., difluoromethoxy, trifluoromethoxy or trifluoroethoxy), cyanoalkoxy (for eg., cyanopropoxy), cycloalkylalkoxy (for eg., cyclopropylmethoxy), or alkylamine (for eg., —N(CH$_3$)$_2$). In this embodiment 'm' is 1 or 2.

According to another embodiment, specifically provided are compounds of the formula (II) in which 'm' is 0.

According to another embodiment, specifically provided are compounds of the formula (II) in which 'n' is 0.

According to another embodiment, specifically provided are compounds of the formula (II) in which R is halogen such as F or Cl; and 'n' is 1.

According to another embodiment, specifically provided are compounds of the formula (II) in which R is —$OR^a$. In this embodiment, $R^a$ may be same or different and are independently selected from hydrogen, alkyl (for eg., methyl, ethyl, n-propyl, n-butyl, n-pentyl, iso-butyl, iso-pentyl, or neo-pentyl), alkoxyalkyl (for eg., methoxyethyl or ethoxyethyl), cycloalkyl (for eg., cyclopentyl or cyclohexyl), cycloalkylalkyl (for eg., cyclopropylmethyl, cyclobutylmethyl or cyalohexylmethyl) haloalkyl (for eg., difluoromethyl, trifluoropropyl or 4-fluorobutyl), cyanoalkyl (cyanopropyl), substituted or unsubstituted arylalkyl (for eg., 3-fluorobenzyl), substituted or unsubstituted heteroarylalkyl (for eg., pyridylmethyl); and 'n' is 1 or 2.

According to another embodiment, specifically provided are compounds of the formula (II) in which R is —OR$^a$. In this embodiment —OR$^a$ substitution is at 2- and 3-position; and 'n' is 2.

According to another embodiment, specifically provided are compounds of the formula (II) in which R is —OR$^a$. In this embodiment —OR$^a$ substitution is at 3- and 4-position; and 'n' is 2.

According to another preferred embodiment, there is provided a compound of formula (IIa),

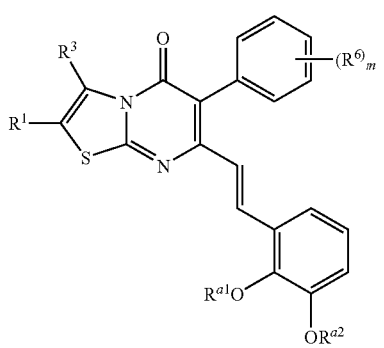

(IIa)

R$^1$, R$^3$, R$^6$, and 'm' are as defined herein above;

each of R$^{a1}$ and R$^{a2}$, which may be the same or different, is selected from hydrogen, substituted or unsubstituted alkyl, haloalkyl, cyanoalkyl, alkenyl, cycloalkyl, alkoxyalkyl, aryl, heteroaryl, heterocyclic group, cycloalkylalkyl, arylalkyl, heteroarylalkyl, or heterocyclylalkyl;

It should be understood that the formula (IIa) structurally encompasses all geometrical isomers, stereoisomers, including enantiomers and diastereomers, and pharmaceutically acceptable salts that may be contemplated from the chemical structure of the genus described herein.

According to one embodiment, specifically provided are compounds of the formula (IIa) in which both R$^1$ and R$^3$ are hydrogen.

According to another embodiment, specifically provided are compounds of the formula (IIa) in which R$^1$ and R$^3$ are independently hydrogen, halogen (for eg., F or Cl), substituted or unsubstituted alkyl (for eg., methyl), or haloalkyl (for eg., trifluoromethyl).

According to another embodiment, specifically provided are compounds of the formula (IIa) in which R$^6$ is halogen (for eg., F or Cl), hydroxyl, cyano, acyl (for eg., —C(O)CH$_3$), substituted or unsubstituted alkyl (for eg., t-butyl), substituted or unsubstituted alkoxy (for eg., methoxy or ethoxy), substituted or unsubstituted cycloalkylalkoxy (for eg., cyclopropylmethoxy), haloalkyl (for eg., trifluoromethyl), haloalkoxy (for eg., difluoromethoxy, trifluoromethoxy or trifluoroethoxy), cyanoalkoxy (for eg., cyanopropoxy), cycloalkylalkoxy (for eg., cyclopropylmethoxy) or alkylamine (for eg., —N(CH$_3$)$_2$). In this embodiment 'm' is 1 or 2.

According to another embodiment, specifically provided are compounds of the formula (IIa) in which 'm' is 0.

According to another embodiment, specifically provided are compounds of the formula (IIa) in which each occurrence of R$^{a1}$ and R$^{a2}$ may be same or different are independently selected from hydrogen, alkyl (for eg., methyl, ethyl, n-propyl, n-butyl, n-pentyl, iso-butyl, iso-pentyl, or neo-pentyl), alkoxyalkyl (for eg., methoxyethyl or ethoxyethyl), cycloalkyl (for eg., cyclopentyl or cyclohexyl), cycloalkylalkyl (for eg., cyclopropylmethyl, cyclobutylmethyl or cyalo-hexylmethyl), haloalkyl (for eg., fluorobutyl, difluoromethyl, trifluoropropyl or 4-fluorobutyl), cyanoalkyl (for eg., cyanopropyl), substituted or unsubstituted arylalkyl (for eg., 3-fluoro benzyl), substituted or unsubstituted heteroarylalkyl (for eg., pyridylmethyl).

According to another more preferred embodiment, there is provided a compound of formula (IIb),

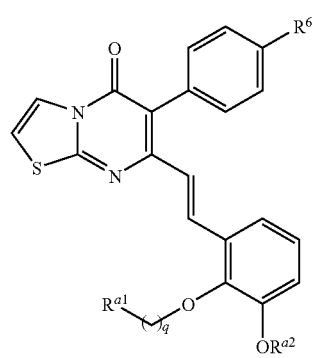

(IIb)

at each occurrence, R$^6$ is independently selected from halogen, hydroxyl, nitro, cyano, —COOH, —NR$^4$R$^5$, substituted or unsubstituted alkyl, alkoxy, haloalkyl, or haloalkyloxy;

R$^{a1}$ is selected from substituted or unsubstituted alkyl, alkoxy, or cycloalkyl;

R$^{a2}$ is selected from substituted or unsubstituted alkyl or haloalkyl; and

'q' is an integer ranging from 1 to 4, inclusive.

It should be understood that the formula (IIb) structurally encompasses all geometrical isomers, stereoisomers, including enantiomers and diastereomers, and pharmaceutically acceptable salts that may be contemplated from the chemical structure of the genus described herein.

According to one embodiment, there is provided a compound of formula (III),

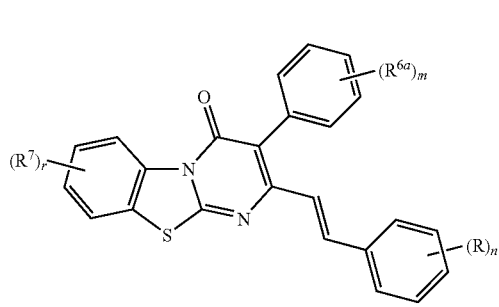

(III)

'r' is an integer ranging from 0 to 4, inclusive;

wherein at each occurrence, R$^{6a}$, which may be the same or different, is independently selected from halogen, hydroxyl, nitro, cyano, —COOH, —NR$^4$R$^5$, acyl, substituted or unsubstituted alkyl, alkenyl, alkoxy, cyanoalkoxy, haloalkyl, haloalkyloxy, cycloalkyl, cycloalkylalkyl, cycloalkylalkoxy, aryl, heterocyclic group, or heteroaryl;

at each occurrence, R$^7$, is independently selected from halogen, nitro, cyano, substituted or unsubstituted alkyl, alkenyl, alkynyl, cycloalkyl, aryl, heteroaryl, heterocyclic group, —NR$^4$R$^5$, —S(O)$_p$NR$^4$R$^5$, or —S(O)$_p$R$^4$; and R, R$^4$, R$^5$, 'm' 'n' and 'p' are as defined herein above;

It should be understood that the formula (III) structurally encompasses all geometrical isomers, stereoisomers, including enantiomers and diastereomers, and pharmaceutically acceptable salts that may be contemplated from the chemical structure of the genus described herein.

According to one embodiment, specifically provided are compounds of the formula (III) in which $R^6$ is cyano, haloalkoxy (for eg., trifluoromethoxy), In this embodiment 'm' is 1.

According to another embodiment, specifically provided are compounds of the formula (III) in which R is —$OR^a$. In this embodiment —$OR^a$ substitution is at 2- and 3-position; and 'n' is 2.

According to another embodiment, specifically provided are compounds of the formula (III) in which R is —$OR^a$. In this embodiment —$OR^a$ substitution is at 3- and 4-position; and 'n' is 2.

According to another embodiment, specifically provided are compounds of the formula (III) in which R is —$OR^a$. In this embodiment, $R^a$ is independently hydrogen, alkyl (for eg., methyl, n-butyl, or iso-pentyl), alkoxyalkyl (for eg., methoxyethyl or ethoxyethyl), cycloalkylalkyl (for eg., cyclopropylmethyl or cyclobutylmethyl), cyanoalkyl (for eg., cyanopropyl) or heterocycloalkyl (for eg., pyridylmethyl); and 'n' is 1 or 2.

Below are the representative compounds, which are illustrative in nature only and are not intended to limit to the scope of the invention.

7-[(E)-2-(4-Chlorophenyl)vinyl]-6-phenyl-5H-[1,3]thiazolo[3,2-a]pyrimidin-5-one (Compound 1), 7-{(E)-2-[2-(Cyclopropylmethoxy)-3-methoxyphenyl]vinyl}-6-phenyl-5H-[1,3]thiazolo[3,2-a]pyrimidin-5-one, 7-[(E)-2-(2-Cyclopropylmethoxy)-3-methoxyphenyl)-1-ethenyl]-6-(6-fluoro-3-pyridyl)-5H-[1,3]thiazolo[3,2-a]pyrimidin-5-one, 6-[4-(tert-Butylphenyl)]-7-[(E)-2-(2-cyclopropylmethoxy)-3-methoxyphenyl)-1-ethenyl]-5H-[1,3]thiazolo[3,2-a]pyrimidin-5-one, 1-{4-{7-[(E)-2-(2-Cyclopropylmethoxy)-3-methoxyphenyl)-1-ethenyl]-5-oxo-5H-[1,3]thiazolo[3,2-a]pyrimidin-6-yl}phenyl}-1-ethanone, 6-(4-Dimethylaminophenyl)-7-[(E)-2-(2-cyclopropylmethoxy-3-methoxyphenyl]-1-ethenyl]-5H-[1,3]thiazolo[3,2-a]pyrimidin-5-one, 7-[(E)-2-(2-Cyclopropylmethoxy-3-methoxyphenyl)-1-ethenyl]-6-(4-hydroxyphenyl)-5H-[1,3]thiazolo[3,2-a]pyrimidin-5-one, 7-[(E)-2-(2-Cyclopropylmethoxy)-3-methoxyphenyl)-1-ethenyl]-6-(3,5-difluorophenyl)-5H-[1,3]thiazolo[3,2-a]pyrimidin-5-one, 4-{7-[(E)-2-(2-Butoxy-3-methoxyphenyl)-1-ethenyl]-5-oxo-5H-[1,3]thiazolo[3,2-a]pyrimidin-6-yl}benzonitrile, 4-{7-[(E)-2-(3-Methoxy-2-pentyloxyphenyl)-1-ethenyl]-5-oxo-5H-[1,3]thiazolo[3,2-a]pyrimidin-6-yl}benzonitrile, 4-{7-[(E)-2-(2-Isopentyloxy-3-methoxyphenyl)-1-ethenyl]-5-oxo-5H-[1,3]thiazolo[3,2-a]pyrimidin-6-yl}benzonitrile, 4-{7-[(E)-2-(2-Isobutoxy-3-methoxyphenyl)-1-ethenyl]-5-oxo-5H-[1,3]thiazolo[3,2-a]-pyrimidin-6-yl}benzonitrile, 4-{7-[(E)-2-(3-Methoxy-2-neopentyloxyphenyl)-1-ethenyl]-5-oxo-5H-[1,3]thiazolo[3,2-a]pyrimidin-6-yl}benzonitrile, 4-{7-[(E)-2-(3-Methoxy-2-(2-methoxyethoxy)phenyl]-1-ethenyl}-5-oxo-5H-[1,3]-thiazolo[3,2-a]pyrimidin-6-yl}benzonitrile, 4-{7-[(E)-2-(2-Ethoxyethoxy-3-methoxyphenyl]-1-ethenyl}-5-oxo-5H-[1,3]thiazolo[3,2-a]pyrimidin-6-yl}benzonitrile, 4-{7-[(E)-2-[2-(Cyclopropylmethoxy)-3-methoxyphenyl]-ethenyl]-5-oxo-5H-[1,3]thiazolo[3,2-a]pyrimidin-6-yl}benzonitrile 4-{7-[(E)-2-(2-Cyclobutylmethoxy-3-methoxy)phenyl-1-ethenyl]-5-oxo-5H-[1,3]-thiazolo[3,2-a]pyrimidin-6-yl}benzonitrile, 4-{7-[(E)-2-(2-Cyclopentyloxy-3-methoxy)phenyl-1-ethenyl]-5-oxo-5H-[1,3]thiazolo-[3,2-a]pyrimidin-6-yl}benzonitrile, 4-{7-[(E)-2-(2-Cyclohexylmethoxy-3-methoxy)phenyl-1-ethenyl]-5-oxo-5H-[1,3]-thiazolo[3,2-a]pyrimidin-6-yl}benzonitrile, 4-{7-[(E)-2-[2-(3-Fluorobenzyloxy)-3-methoxyphenyl]-1-ethenyl]-5-oxo-5H-[1,3]-thiazolo[3,2-a]pyrimidin-6-yl}benzonitrile, 4-{7-[(E)-2-{3-Methoxy-2-(2-pyridinylmethoxy)phenyl]-1-ethenyl]}-5-oxo-5H-[1,3]-thiazolo[3,2-a]pyrimidin-6-yl}benzonitrile, 4-{7-[(E)-2-{2-(3-Cyanopropoxy)-3-(methoxyphenyl)-1-ethenyl]}-5-oxo-5H-[1,3]thiazolo[3,2-a]pyrimidin-6-yl}benzonitrile, 4-{5-Oxo-7-[(E)-2-(3-pyridyl)-1-ethenyl]-5H-[1,3]thiazolo[3,2-a]pyrimidin-6-yl}-benzonitrile, 7-[(E)-2-(2-Cyclopropylmethoxy)-1-ethenyl]-6-[4-(trifluoromethyl)phenyl]-5H-[1,3]-thiazolo[3,2-a]pyrimidin-5-one, 7-[(E)-2-(3-Methoxy-2-propoxyphenyl)-1-ethenyl]-6-[4-(trifluoromethyl)phenyl]-5H-[1,3]thiazolo[3,2-a]pyrimidin-5-one, 7-[(E)-2-(2-Butoxy-3-methoxyphenyl)-1-ethenyl]-6-[4-(trifluoromethyl)phenyl]-5H-[1,3]thiazolo[3,2-a]pyrimidin-5-one, 7-[(E)-2-(2-Isobutoxy-3-methoxyphenyl)-1-ethenyl]-6-[4-(trifluoromethyl)phenyl]-5H-[1,3]thiazolo[3,2-a]pyrimidin-5-one, 7-[(E)-2-(2-Isopentyloxy-3-methoxyphenyl)-1-ethenyl]-6-[4-(trifluoromethyl)phenyl]-5H-[1,3]thiazolo[3,2-a]pyrimidin-5-one, 7-[(E)-2-(3-Methoxy-2-neopentyloxy)phenyl-1-ethenyl]-6-(4-(trifluoromethyl)phenyl)-5H-[1,3]thiazolo[3,2-a]pyrimidin-5-one, 3-{2-Methoxy-6-{[(E)-2-{5-oxo-6-[4-(trifluoromethyl)phenyl]-5H-[1,3]thiazolo[3,2-a]pyrimidin-7-yl}-1-ethenyl]phenoxy)propyl cyanide, {7-[(E)-2-(2-Methoxyethoxy-3-methoxy)phenyl}vinyl]-6-[4-(trifluoromethyl)phenyl]-5H-[1,3]thiazolo[3,2-a]pyrimidin-5-one, {7-[(E)-2-(2-Ethoxyethoxy-3-methoxy)phenyl-1-ethenyl]-6-[4-(trifluoromethyl)phenyl]-5H-[1,3]thiazolo[3,2-a]pyrimidin-5-one, {7-[(E)-2-(2-Cyclopropylmethoxy)-3-methoxyphenyl]-1-ethenyl]-6-[4-(trifluoromethyl)-phenyl]-5H-[1,3]thiazolo[3,2-a]pyrimidin-5-one, 7-[(E)-2-(2-Cyclobutylmethoxy-3-methoxyphenyl)-1-ethenyl]-6-[4-(trifluoromethyl)-phenyl]-5H-[1,3]thiazolo[3,2-a]pyrimidin-5-one, 7-[(E)-2-(2-Cyclopentyloxy-3-methoxyphenyl)-1-ethenyl]-6-[4-(trifluoromethyl)-phenyl]-5H-[1,3]thiazolo[3,2-a]pyrimidin-5-one (Compound 35), 7-[(E)-2-{3-Methoxy-2-(pyridin-2-ylmethoxy)phenylvinyl]-6-[4-(trifluoromethyl)phenyl]-5H-[1,3]thiazolo[3,2-a]pyrimidin-5-one, 7-[(E)-2-(3-Cyclopropylmethoxy-4-methoxyphenyl)-1-ethenyl]-6-[4-(trifluoromethyl)-phenyl]-5H-[1,3]thiazolo[3,2-a]pyrimidin-5-one, 7-[(E)-2-(4-Cyclopropylmethoxy-3-methoxyphenyl)-1-ethenyl]-6-[4-(trifluoromethyl)-phenyl]-5H-[1,3]thiazolo[3,2-a]pyrimidin-5-one, 7-[(E)-2-Pyridin-3-ylvinyl]-6-[4-(trifluoromethyl)phenyl]-5H-[1,3]thiazolo[3,2-a]pyrimidin-5-one, 7-[(E)-2-(2-Cyclopropylmethoxy-3-methoxyphenyl)-1-ethenyl]-6-[3-(trifluoromethyl)phenyl]-5H-[1,3]thiazolo[3,2-a]pyrimidin-5-one, 6-(4-Dimethylaminophenyl)-7-[(E)-2-(2-isobutoxy-3-methoxyphenyl)-1-ethenyl]-5H-[1,3]thiazolo[3,2-a]pyrimidin-5-one, 6-(4-Dimethylaminophenyl)-7-[(E)-2-(3-methoxy-2-neopentyloxy)phenyl-1-ethenyl]-5H-[1,3]thiazolo[3,2-a]pyrimidin-5-one (Compound 42), 7-[(E)-2-(2-Cyclopropylmethoxy-3-methoxyphenyl)-1-ethenyl]-6-(4-methoxyphenyl)-5H-[1,3]thiazolo[3,2-a]pyrimidin-5-one, 7-[(E)-2-(2-Cyclopropylmethoxy-3-methoxyphenyl)-1-ethenyl]-6-(4-ethoxyphenyl)-5H-[1,3]thiazolo[3,2-a]pyrimidin-5-one, 7-[(E)-2-(2-Cyclopropylmethoxy-3-methoxyphenyl)-1-ethenyl]-6-(4-(2,2,2-trifluoroethoxy)phenyl]-5H-[1,3]thiazolo[3,2-a]pyrimidin-5-one, 3-4-{7-[(E)-2-(2-Cyclopropylmethoxy-3-methoxyphenyl)-1-ethenyl]-5H-[1,3]thiazolo-[3,2-a]pyrimidin-6-yl}phenoxy)propyl cyanide, 7-[(E)-2-(2-Cyclopropylmethoxy-3-methoxyphenyl)-1-ethenyl]-6-(4-cyclopropylmethoxyphenyl)-5H-[1,3]thiazolo[3,2-a]pyrimidin-5-one, 7-[(E)-2-(2-Cyclopropylmethoxy-3-methoxyphenyl)-1-ethenyl]-6-(4-difluoromethoxy phenyl]-5H-[1,3]thiazolo[3,2-a]pyrimidin-5-one, 7-[(E)-2-(2-Cyclopropylmethoxy-3-fluorophenyl)-1-ethenyl]-6-[4-(trifluoromethoxy)-phenyl]-5H-[1,3]thiazolo[3,2-a]pyrimidin-5-one, 7-[(E)-2-{2-Isopentyloxy-3-methoxyphenyl}-1-ethenyl]-6-[4-(trifluoromethoxy)phenyl]-5H-[1,3]thiazolo[3,2-a]pyrimidin-5-one, 7-[(E)-2-(2-Isobutoxy-3-methoxyphenyl)-1-ethenyl]-6-[4-(trifluoromethoxy)phenyl]-5H-[1,3]thiazolo[3,2-a]pyrimidin-5-one, 7-[(E)-2-{3-Methoxy-2-neopentyloxyphenyl}-1-ethenyl]-6-[4-(trifluoromethoxy)-phenyl]-5H-[1,3]thiazolo[3,2-a]pyrimidin-5-one, 7-[(E)-2-{2-(2-Ethoxyethoxy)-3-methoxyphenyl}-1-ethenyl]-6-[4-(trifluoromethoxy)-phenyl]-5H-[1,3]thiazolo[3,2-a]pyrimidin-5-one, 7-[(E)-2-(3-Methoxy-2-propoxyphenyl)-1-ethenyl]-6-[4-(trifluoromethoxy)phenyl]-5H-[1,3]thiazolo[3,2-a]pyrimidin-5-one, 7-[(E)-2-(3-Methoxy-2-pentyloxyphenyl)-1-ethenyl]-6-[4-(trifluoromethoxy)phenyl]-5H-[1,3]thiazolo[3,2-a]pyrimidin-5-one, 4-{7-[(E)-2-{2-(4-Fluorobutoxy)-3-methoxyphenyl}-1-ethenyl]-6-[4-(trifluoromethoxy)-phenyl]-5H-[1,3]thiazolo[3,2-a]pyrimidin-5-one, 7-[(E)-2-(2-Butoxy-3-methoxyphenyl)-1-ethenyl]-6-[4-(trifluoromethoxy)phenyl]-5H-[1,3]thiazolo[3,2-a]pyrimidin-5-one, 7-{(E)-2-[2-(Cyclopropylmethoxy)-3-methoxyphenyl}-1-ethenyl]-6-(4-trifluoromethoxy)phenyl)-5H-[1,3]thiazolo[3,2-a]pyrimidin-5-one, 7-{(E)-(2,3-Dihydroxy)phenyl}-1-ethenyl]-6-(4-trifluoromethoxy-phenyl)-5H-[1,3]thiazolo[3,2-a]pyrimidin-5-one, 7-{(E)-(2-Cyclopropylmethoxy-3-hydroxy)phenyl]-1-ethenyl}-6-(4-trifluoromethoxyphenyl)-5H-[1,3]thiazolo[3,2-a]pyrimidin-5-one, 7-{(E)-2-[2-(Cyclopropylmethoxy)-3-ethoxyphenyl}-1-ethenyl]-6-(4-trifluoromethoxy-phenyl)-5H-[1,3]thiazolo[3,2-a]pyrimidin-5-one, 7-{(E)-2-[2-(Cyclopropylmethoxy)-3-(2-ethoxyethoxy)phenyl]-1-ethenyl}-6-(4-trifluoromethoxyphenyl)-5H-[1,3]thiazolo[3,2-a]pyrimidin-5-one, 7-{(E)-2-[2-(Cyclopropylmethoxy)-3-difluoromethoxyphenyl]-1-ethenyl}-6-(4-trifluoromethoxyphenyl)-5H-[1,3]thiazolo[3,2-a]pyrimidin-5-one, 7-{(E)-2-[2-(Cyclopropylmethoxy)-3-(cyclopropylmethoxy)phenyl]-1-ethenyl}-6-(4-trifluoromethoxyphenyl)-5H-[1,3]thiazolo[3,2-a]pyrimidin-5-one, 7-{(E)-2-[2-(Cyclopropylmethoxy)-3-(3-cyanopropoxy)phenyl]-1-ethenyl}-6-(4-trifluoromethoxyphenyl)-5H-[1,3]thiazolo[3,2-a]pyrimidin-5-one, 7-{(E)-2-[2-(Cyclopropylmethoxy)-3-propoxyphenyl}-1-ethenyl]-6-(4-trifluoromethoxy-phenyl)-5H-[1,3]thiazolo[3,2-a]pyrimidin-5-one, 7-[(E)-2-{2-Cyclobutylmethoxy-3-methoxyphenyl}-1-ethenyl]-6-[4-(trifluoromethoxy)-phenyl]-5H-[1,3]thiazolo[3,2-a]pyrimidin-5-one, 7-[(E)-2-{2-(Cyclopentyloxy-3-methoxyphenyl}-1-ethenyl]-6-[4-(trifluoromethoxy)-phenyl]-5H-[1,3]thiazolo[3,2-a]pyrimidin-5-one, 7-[(E)-2-(2-Hydroxy-3-methoxyphenyl)-1-ethenyl]-6-[4-(trifluoromethoxy)phenyl]-5H-[1,3]thiazolo[3,2-a]pyrimidin-5-one, 4-{7-[(E)-2-{3-Methoxy-2-2-trifluoromethylethoxy)phenyl}-1-ethenyl]-6-[4-(trifluoromethoxy)phenyl]-5H-[1,3]thiazolo[3,2-a]pyrimidin-5-one, 7-[(E)-2-(2-Cyclohexylmethoxy-3-methoxyphenyl)-1-ethenyl]-6-[4-(trifluoromethoxy)-phenyl]-5H-[1,3]thiazolo[3,2-a]pyrimidin-5-one, 7-[(E)-2-(2-Cyclohexyloxy-3-methoxyphenyl)-1-ethenyl]-6-[4-(trifluoromethoxy)-phenyl]-5H-[1,3]thiazolo[3,2-a]pyrimidin-5-one, 7-[(E)-2-{3-Methoxy-2-(2-methoxyethoxy)phenyl}-1-ethenyl]-6-[4-(trifluoromethoxy)phenyl]-5H-[1,3]thiazolo[3,2-a]pyrimidin-5-one, 4-{7-[(E)-2-{(3-Cyanopropoxy)-3-methoxy}phenylvinyl]-6-[4-(trifluoromethoxy)-phenyl]-5H-[1,3]thiazolo[3,2-a]pyrimidin-5-one, 7-[(E)-2-(2-Cyclopropylmethoxy-3-methoxyphenyl)-1-ethenyl]-2-methyl-6-[4-(trifluoromethoxy)phenyl]-5H-[1,3]thiazolo[3,2-a]pyrimidin-5-one, 7-[(E)-2-(2-Cyclopropylmethoxy-3-methoxyphenyl)-1-ethenyl]-3-methyl-6-[4-(trifluoromethoxy)phenyl]-5H-[1,3]thiazolo[3,2-a]pyrimidin-5-one, 7-[(E)-2-(2-Cyclopropylmethoxy-3-methoxyphenyl)-1-ethenyl]-2,3-dimethyl-6-[4-(trifluoromethoxy)phenyl]-5H-[1,3]thiazolo[3,2-a]pyrimidin-5-one, 2-Chloro-7-[(E)-2-(2-(2,2-dimethylpropoxy)-3-methoxyphenyl)vinyl]-6-[4-(trifluoromethoxy)phenyl]-5H-[1,3]thiazolo[3,2-a]pyrimidin-5-one, 2-Chloro-6-[4-(dimethylamino)phenyl]-7-[(E)-2-(2-(2,2-dimethylpropoxy)-3-methoxy-phenyl)vinyl]-5H-[1,3]thiazolo[3,2-a]pyrimidin-5-one, 4-{2-Chloro-7-[(E)-2-(2-(2,2-dimethylpropoxy)-3-methoxyphenyl)vinyl]-5-oxo-5H-[1,3]thiazolo[3,2-a]pyrimidin-6-yl}benzonitrile, 2-Chloro-6-[4-(dimethylamino)phenyl]-7-[(E)-2-(2-isobutoxy-3-methoxyphenyl)vinyl]-5H-[1,3]thiazolo[3,2-a]pyrimidin-5-one, 4-{7-[(E)-2-(3-Methoxy-2-neopentyloxyphenyl)-1-ethenyl]-5-oxo-3-(trifluoromethyl)-5H-[1,3]thiazolo[3,2-a]pyrimidin-6-yl}benzonitrile, 4-(2-{(E)-2-[2-(3-Cyanopropoxy)-3-methoxyphenyl}-1-ethenyl}-4-oxo-4H-benzo[4,5]-[1,3]thiazolo-[3,2]pyrimidin-3-yl)benzonitrile, 4-(2-{(E)-2-[3-Methoxy-2-(methoxyethoxy)phenyl}-1-ethenyl}-4-oxo-4H-benzo[4,5]-[1,3]thiazolo-[3,2]pyrimidin-3-yl)benzonitrile, 4-{2-[(E)-2-[2-(2-Ethoxyethoxy)-3-methoxy]phenyl}-1-ethenyl]-4-oxo-4H-benzo[4,5]-[1,3]thiazolo-[3,2]pyrimidin-3-yl)benzonitrile, 4-{2-[(E)-2-[2-Cyclopropylmethoxy-3-methoxy]phenyl}-1-ethenyl]-4-oxo-4H-benzo[4,5]-[1,3]thiazolo-[3,2]pyrimidin-3-yl)benzonitrile, 4-{2-[(E)-2-[2-Butoxy-3-methoxy]phenyl}-1-ethenyl]-4-oxo-4H-benzo[4,5]-[1,3]thiazolo-[3,2]pyrimidin-3-yl)benzonitrile, 4-{2-[(E)-2-[2-(3-Methylbutoxy-3-methoxy]phenyl}-1-ethenyl]-4-oxo-4H-benzo[4,5]-[1,3]thiazolo-[3,2]pyrimidin-3-yl)benzonitrile, 4-{2-[(E)-2-[2-Cyclobutylmethoxy-3-methoxy]phenyl}-1-ethenyl]-4-oxo-4H-benzo[4,5]-[1,3]thiazolo-[3,2]pyrimidin-3-yl)benzonitrile, 4-{2-[(E)-2-[3-Methoxy-2-pyridin-2-ylmethoxy]phenyl}-1-ethenyl]-4-oxo-4H-benzo[4,5]-[1,3]thiazolo-[3,2]pyrimidin-3-yl)benzonitrile, 2-{(E)-2-[(2-Cyclopropylmethoxy)-3-methoxyphenyl]-1-ethenyl}-3-(4-trifluoromethyl-phenyl)-4H-benzo[4,5][1,3]thiazolo-[3,2-a]pyrimidin-4-one, 2-{(E)-2-[(2-Methoxyethoxy)-3-methoxyphenyl]-1-ethenyl}-3-(4-trifluoromethyl-phenyl)-4H-benzo[4,5][1,3]thiazolo-[3,2-a]pyrimidin-4-one, 2-{(E)-2-[(2-Ethoxyethoxy)-3-methoxyphenyl]-1-ethenyl}-3-(4-trifluoromethyl-phenyl)-4H-benzo[4,5][1,3]thiazolo-[3,2-a]pyrimidin-4-one, 2-{(E)-2-[(3-Cyanopropoxy-3-methoxy)phenyl]-1-ethenyl}-3-(4-trifluoromethyl-phenyl)-4H-benzo[4,5][1,3]thiazolo-[3,2-a]pyrimidin-4-one, 2-{(E)-2-[2 Cyclopropylmethoxy-3-methoxy phenyl]-1-ethenyl}-3-(4-trifluoromethoxy-phenyl)-4H-benzo[4,5][1,3]thiazolo-[3,2-a]pyrimidin-4-one, 2-{(E)-2-[3-Methoxy-2-(2-methoxyethoxy)phenyl]-1-ethenyl}-3-(4-trifluoromethoxy-phenyl)-4H-benzo[4,5][1,3]thiazolo-[3,2-a]pyrimidin-4-one, 2-{(E)-2-[(2-Ethoxyethoxy)-3-methoxyphenyl]-1-ethenyl}-3-(4-trifluoromethoxy-phenyl)-4H-benzo[4,5][1,3]thiazolo-[3,2-a]pyrimidin-4-one, and 2-[(E)-2-(2-Cyclopropylmethoxy-3-methoxyphenyl)vinyl]-3-(4-trifluoromethoxyphenyl)-10-methylpyrimido[1,2-a]benzimidazol-4(10H)-one or an analog, tautomer, regiomer, geometrical isomers, stereoisomer, enantiomer, diastereomer or pharmaceutically acceptable salt of compounds 1 to 98 are also contemplated.

According to another embodiment, specifically provided are compounds of Formula I, Formula II, Formula IIa, Formula IIb or Formula III, or a salt thereof, that inhibits a TRPV3 function with an $IC_{50}$ value of less than 10,000 nM, or even less than 1000, 500, 250 or 100 nM. In other embodiments, specifically provided are compounds of Formula I, Formula II, Formula IIa, Formula IIb or Formula III, or a salt thereof, that inhibits a TRPV3 function with an $IC_{50}$ value of less than 50 nM.

Also provided herein are processes for preparing compounds described herein.

DETAILED DESCRIPTION

The present patent application provides fused pyrimidine-one compounds, which may be used as TRPV3 modulators, and processes for the synthesis of these compounds. Pharmaceutically acceptable salts, enantiomers, and diastereomers of compounds described herein are separately and individually contemplated. Pharmaceutical compositions containing the described compounds together with pharmaceutically acceptable carriers, excipients or diluents, which can be used for the treatment of diseases, condition and/or disorders mediated by TRPV3 are separately contemplated.

The invention is defined by the claims and not limited by the description provided herein below. The terms used in the appended claims are defined herein in this glossary section, with the proviso that the claim terms may be used in a different manner if so defined ly by express recitation.

The terms "halogen" or "halo" includes fluorine, chlorine, bromine, or iodine

The term "alkyl" refers to hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl). The term "$C_{1-6}$ alkyl" refers to an alkyl chain having 1 to 6 carbon atoms. Unless set forth or recited to the contrary, all alkyl groups described or claimed herein may be straight chain or branched, substituted or unsubstituted.

The term "alkenyl" refers to an hydrocarbon chain containing from 2 to 10 carbon atoms and including at least one carbon-carbon double bond. Non-limiting examples of alkenyl groups include ethenyl, 1-propenyl, 2-propenyl (allyl), iso-propenyl, 2-methyl-1-propenyl, 1-butenyl, and 2-butenyl. Unless set forth or recited to the contrary, all alkenyl groups described or claimed herein may be straight chain or branched, substituted or unsubstituted.

The term "alkynyl" refers to a hydrocarbyl radical having at least one carbon-carbon triple bond, and having 2 to about 12 carbon atoms (with radicals having 2 to about 10 carbon atoms being preferred). Non-limiting examples of alkynyl groups include ethynyl, propynyl, and butynyl. Unless set forth or recited to the contrary, all alkynyl groups described or claimed herein may be straight chain or branched, substituted or unsubstituted.

The term "alkoxy" denotes an alkyl group attached via an oxygen linkage to the rest of the molecule. Representative examples of such groups are —$OCH_3$ and —$OC_2H_5$. Unless set forth or recited to the contrary, all alkoxy groups described or claimed herein may be straight chain or branched, substituted or unsubstituted.

The term "cycloalkyl" denotes a non-aromatic mono or multicyclic ring system of 3 to about 12 carbon atoms, such as cyclopropyl, cyclobutyl, cyclopentyl, and cyclohexyl. Examples of multicyclic cycloalkyl groups include, but are not limited to, perhydronapththyl, adamantyl and norbornyl groups, bridged cyclic groups or sprirobicyclic groups, e.g., sprio(4,4)non-2-yl. Unless set forth or recited to the contrary, all cycloalkyl groups described or claimed herein may be substituted or unsubstituted.

The term "cycloalkylalkyl" refers to a cyclic ring-containing radical having 3 to about 8 carbon atoms directly attached to an alkyl group. The cycloalkylalkyl group may be attached to the main structure at any carbon atom in the alkyl group that results in the creation of a stable structure. Non-limiting examples of such groups include cyclopropylmethyl, cyclobutylethyl, and cyclopentylethyl. Unless set forth or recited to the contrary, all cycloalkylalkyl groups described or claimed herein may be substituted or unsubstituted.

The term "cycloalkenyl" refers to a cyclic ring-containing radical having 3 to about 8 carbon atoms with at least one carbon-carbon double bond, such as cyclopropenyl, cyclobutenyl, and cyclopentenyl. Unless set forth or recited to the contrary, all cycloalkenyl groups described or claimed herein may be substituted or unsubstituted.

The term "aryl" refers to an aromatic radical having 6 to 14 carbon atoms, including monocyclic, bicyclic and tricyclic aromatic systems, such as phenyl, naphthyl, tetrahydronapthyl, indanyl, and biphenyl. Unless set forth or recited to the contrary, all aryl groups described or claimed herein may be substituted or unsubstituted.

The term "arylalkyl" refers to an aryl group as defined above directly bonded to an alkyl group as defined above, e.g., —$CH_2C_6H_5$ and —$C_2H_4C_6H_5$.

The term "heterocyclyl" and "heterocyclic ring" "heterocyclic group" refers to a stable 3- to 15-membered ring radical which consists of carbon atoms and from one to five heteroatoms selected from nitrogen, phosphorus, oxygen and sulfur. For purposes of this invention, the heterocyclic ring radical may be a monocyclic, bicyclic or tricyclic ring system, which may include fused, bridged or spiroing systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heterocyclic or heteroaryl). Examples of such heterocyclic ring radicals include, but are not limited to, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazolyl, imidazolyl, tetrahydroisoquinolinyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxazolidinyl, triazolyl, indanyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofuranyl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, and isochromanyl. The heterocyclic ring radical may be attached to the main structure at any heteroatom or carbon atom that results in the creation of a stable structure. Unless set forth or recited to the contrary, all heterocyclyl groups described or claimed herein may be substituted or unsubstituted, including those included in more complex substructures.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure.

The term "heteroaryl" refers to an aromatic heterocyclic ring radical. The heteroaryl ring radical may be attached to the main structure at any heteroatom or carbon atom that results in the creation of a stable structure. Unless set forth or recited to the contrary, all heteroaryl groups described or claimed herein may be substituted or unsubstituted, including those included in more complex substructures.

The term "heteroarylalkyl" refers to a heteroaryl ring radical directly bonded to an alkyl group. The heteroarylalkyl radical may be attached to the main structure at any carbon atom in the alkyl group that results in the creation of a stable structure.

Unless otherwise specified, the term "substituted" as used herein refers to a group or moiety having one or more of the substituents attached to the structural skeleton of the group or moiety, including, but not limited to such substituents as hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenylalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstiuted heterocyclic ring, substituted or unsubstiuted guanidine, —$COOR^x$, —$C(O)R^x$, —$C(S)R^x$, —$C(O)NR^xR^y$, —$C(O)ONR^xR^y$, —$NR^xCONR^yR^z$, —$N(R^x)SOR^y$, —$N(R^x)SO_2R^y$, —(=N—N($R^x$)$R^y$), —$NR^xC(O)OR^y$, —$NR^xR^y$, —$NR^xC(O)R^y$, —$NR^xC(S)R^y$, —$NR^xC(S)NR^yR^z$, —$SONR^xR^y$, —$SO_2NR^xR^y$, —$OR^x$, —$OR^xC(O)NR^xR^y$, —$OR^xC(O)OR^y$, —$OC(O)R^x$, —$OC(O)NR^xR^y$, —$R^xNR^yC(O)R^z$, —$R^xOR^y$, —$R^xC(O)OR^y$, —$R^xC(O)NR^xR^z$, —$R^xC(O)R^y$, —$R^xOC(O)R^y$, —$SR^x$, —$SOR^x$, —$SO_2R^x$, and —$ONO_2$, wherein $R^x$, $R^y$ and $R^z$ are independently selected from hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, or substituted or unsubstituted heterocyclic ring. The substituents in the aforementioned "substituted" groups cannot be further substituted. For example, when the substituent on "substituted alkyl" is "substituted aryl", the substituent on "substituted aryl" cannot be "substituted alkenyl".

The term "treating" or "treatment" of a state, disorder or condition includes: (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof, or (c) relieving the disease, i.e., causing regression of the state, disorder or condition or at least one of its clinical or subclinical symptoms.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disorder or condition, is sufficient to cause the effect in the subject which is the purpose of the administration. The "therapeutically effective amount" will vary depending on the compound, the disease and its severity and the age, weight, physical condition and responsiveness of the subject to be treated.

The compound described in the present patent application may form salts. Non-limiting examples of pharmaceutically acceptable salts forming part of this patent application include salts derived from inorganic bases, salts of organic bases, salts of chiral bases, salts of natural amino acids and salts of non-natural amino acids. With respect to the overall compounds described by the Formula (I), the present patent application extends to these stereoisomeric forms and to mixtures thereof. To the extent prior art teaches synthesis or separation of particular stereoisomers, the different stereoisomeric forms of the present patent application may be separated from one another by the method known in the art, or a given isomer may be obtained by stereospecific or asymmetric synthesis. Tautomeric forms and mixtures of compounds described herein are also contemplated.

Pharmaceutical Compositions

The pharmaceutical composition provided in the present invention includes at least one compound described herein and at least one pharmaceutically acceptable excipient (such as a pharmaceutically acceptable carrier or diluent). Preferably, the contemplated pharmaceutical compositions include the compound(s) described herein in an amount sufficient to inhibit TRPV3 receptor in a subject.

The subjects contemplated include, for example, a living cell and a mammal, including human. The compound of the present invention may be associated with a pharmaceutically acceptable excipient (such as a carrier or a diluent) or be diluted by a carrier, or enclosed within a carrier which can be in the form of a capsule, sachet, paper or other container.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone.

The carrier or diluent may include a sustained release material, such as glyceryl monostearate or glyceryl distearate, alone or mixed with a wax.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared by conventional techniques known in the art. For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be in conventional forms, for example, capsules, tablets, aerosols, solutions, suspensions or products for topical application.

The route of administration may be any route which effectively transports the active compound of the invention to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment).

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Liquid formulations include, but are not limited to, syrups, emulsions, soft gelatin and sterile injectable liquids, such as aqueous or non-aqueous liquid suspensions or solutions. For parenteral application, particularly suitable are injectable solutions or suspensions formulation.

Liquid formulations include, but are not limited to, syrups, emulsions, soft gelatin and sterile injectable liquids, such as aqueous or non-aqueous liquid suspensions or solutions.

For parenteral application, particularly suitable are injectable solutions or suspensions, preferably aqueous solutions with the active compound dissolved in polyhydroxylated castor oil.

Suitable doses of the compounds for use in treating the diseases and disorders described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects. For example, the daily dosage of the TRPV3 modulator can range from about 0.1 to about 30.0 mg/kg. Mode of administration, dosage forms, suitable pharmaceutical excipients, diluents or carriers can also be well used and adjusted by those skilled in the art. All changes and modifications are envisioned within the scope of the present invention.

Methods of Treatment

The present invention provides compounds and pharmaceutical formulations thereof that are useful in the treatment of diseases, conditions and/or disorders modulated by TRPV3. The present patent application further provides a method of treating a disease, condition and/or disorder modulated by TRPV3 in a subject in need thereof by administering to the subject a therapeutically effective amount of a compound or a pharmaceutical composition of the present invention.

Diseases, conditions, and/or disorders that are modulated by TRPV3 are believed to include, but are not limited to pain, nociceptive pain, dental pain, cardiac pain arising from an ischemic myocardium, pain due to migraine, acute pain, chronic pain, neuropathic pain, post-operative pain, pain due to neuralgia (e.g., post-herpetic neuralgia or trigeminal neuralgia), pain due to diabetic neuropathy, dental pain and cancer pain, inflammatory pain conditions (e.g. arthritis and osteoarthritis), arthralgia, neuropathies, neurodegeneration, retinopathy, neurotic skin disorder, stroke, urinary bladder hypersensitiveness, urinary incontinence, vulvodynia, gastrointestinal disorders such as irritable bowel syndrome, gastro-esophageal reflux disease, enteritis, ileitis, stomach-duodenal ulcer, inflammatory bowel disease, Crohn's disease, celiac disease, an inflammatory disease such as pancreatitis, a respiratory disorder such as allergic and non-allergic rhinitis, asthma or chronic obstructive pulmonary disease, irritation of skin, eye or mucous membrane, dermatitis, pruritic conditions such as uremic pruritus, fervescence, muscle spasms, emesis, dyskinesias, depression, Huntington's disease, memory deficits, restricted brain function, amyotrophic lateral sclerosis (ALS), dementia, arthritis, osteoarthritis, diabetes, obesity, urticaria, actinic keratosis, keratocanthoma, alopecia, Meniere's disease, tinnitus, hyperacusis, anxiety disorders and benign prostate hyperplasia. Additional diseases, conditions and/or disorders modulated by TRPV3 is illustrated, for example in WO2007/056124; Wissenbach, U. et al, Biology of the cell (2004), 9, 47-54; Nilius, B. et al., Physiol Rev (2007), 87, 165-217; Okuhara, D. Y. et al, Expert Opinion on Therapeutic Targets (2007), 11, 391-401; Hu, H. Z. et al, Journal of Cellular Physiology, (2006), 208, 201-212 and references cited therein, all of which are incorporated herein by reference in their entirety and for the purpose stated.

Methods of Preparation

The compounds described herein, including compounds of general formula (I), formula (II), formula (IIa), formula (IIb), and formula (III) and specific examples, are prepared using techniques known to one of ordinary skill in the art. The compounds described herein are prepared through the reaction sequences as depicted in schemes 1 to 7. All possible stereoisomers are also envisioned within the scope of this invention.

The starting materials for the below reaction schemes are commercially available or can be prepared according to methods known to one skilled in the art or by methods disclosed herein. In general, the compounds according to the present invention may be prepared through the reaction schemes as follows, wherein all symbols are as defined above.

A general approach for the synthesis of the general formula (I) is described in schemes 1 to 3. Amine of a general formula (1) is either commercially available or prepared by the reaction of thiourea with appropriately substituted carbonyl compounds in presence of iodine or hydrobromic acid and bromine at reflux temperatures in polar protic solvents such as ethanol according to methods known in the art. (Foulis, M. J. et al. *J. Med. Chem.*, (1971), 14, 1075-1077; Kikugawa, Y. et al. *Synthesis.*, (1981), 124-125; Tanaka, K. et al. *J. Het. Chem.*, (1991), 28, 907-911; Kauffman J. M. et al. *J. Org. Chem.* (2003), 68, 839-853).

Scheme 1:

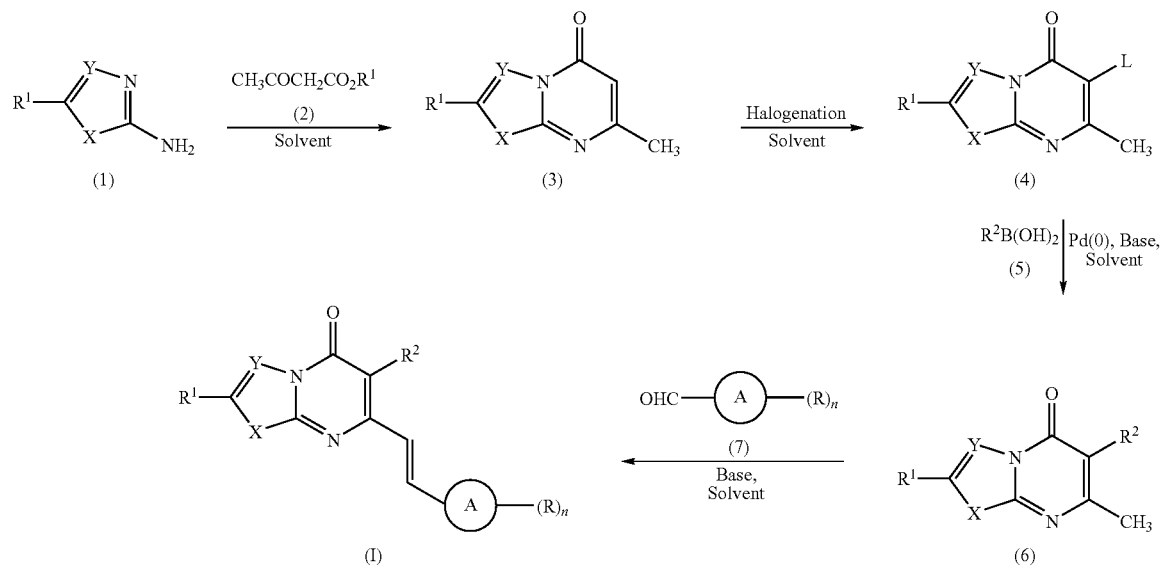

According to one embodiment, a compound of formula (I) is prepared by the process described in scheme 1. Amine of a general (1) is converted into compound of formula (3) by reacting with compound of formula (2) (where R' is H or alkyl), in the presence of suitable solvent e.g. acetic acid, polyphosphoric acid etc. (Allen, C. F. H. et al. *J. Org. Chem.*, (1959), 24, 779-787; Andrew, H. F. et al. *J. Het. Chem.*, (1967), 4, 577-581; Hermecz, I. et al. *Synthesis.*, (1984), 155-158). Halogenation of intermediate of a formula (3) with suitable halogenating agents [e.g., N-Iodosuccinimide (NIS), N-Bromosuccinimide (NBS), Iodine and Ceric ammonium nitrate (CAN) etc.] in suitable polar aprotic solvents (e.g., acetonitrile, tetrahydrofuran etc.) affords halogenated compound of formula (4) (where L is halogen) which, in turn, subjected to palladium (0) catalyzed C—C coupling (e.g, Suzuki coupling) reactions with appropriate boronic acid of formula (5) gives compound of formula (6). Compound of formula (6) is then converted into compound of general formula (I) by classical modified Knoevenagel reaction with appropriate aldehyde of formula (7) and in the presence of suitable base (e.g. sodium acetate, sodium ethoxide, potassium tert-butoxide, sodium hydride etc.) in suitable polar solvent (e.g, ethanol, dimethylformamide, tetrahydrofuran etc.).

Scheme 2:

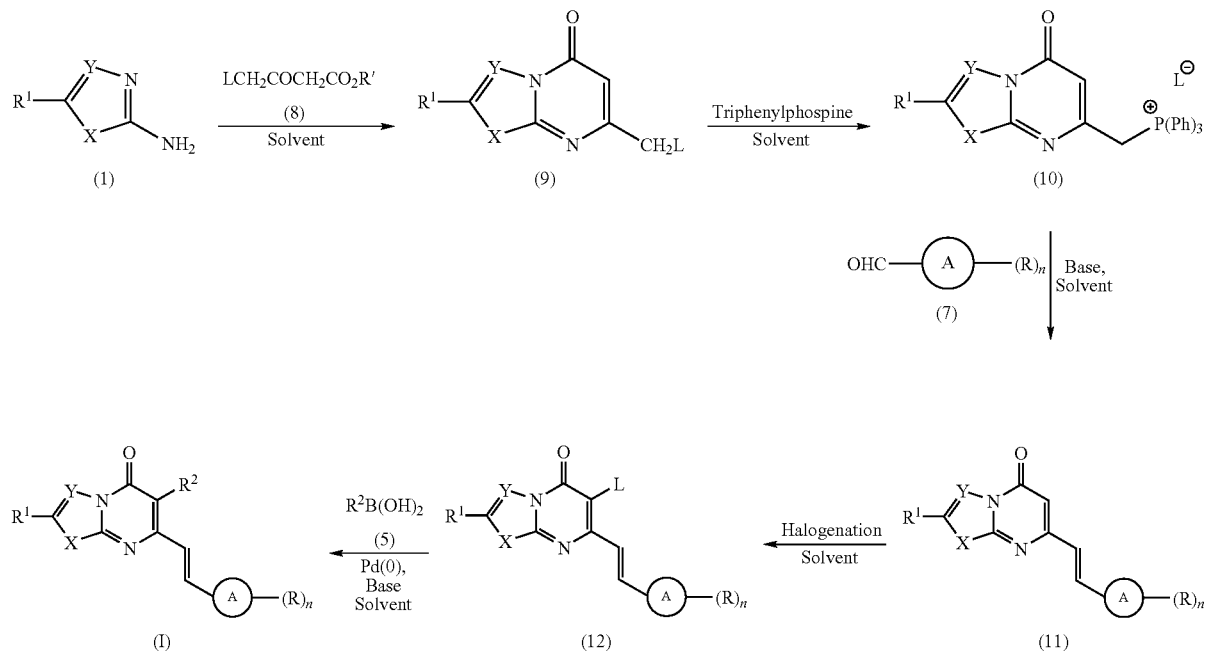

According to another embodiment, compound of formula (I) is prepared by the process described in scheme 2. Amine of general formula (1) is converted into compound of formula (9) by reacting with compound of formula (8) (where R' is H or alkyl; and L is halogen), in the presence of suitable solvent e.g. acetic acid, polyphosphoric acid etc. (Vanelle, P. et al. *J. Het. Chem.*, (2006), 43, 1225-1229). Compound of formula (9) is then converted into corresponding phosphonium salt of formula (10) (where L⊖ is halide) by reaction with triphenylphospine (TPP) and in the presence of a suitable solvent (e.g, acetonitrile, toluene etc.). Compound of formula (11) is prepared by classical Wittig reaction of corresponding phosphonium salt of formula (10) with appropriate aldehyde of formula (7) in the presence of suitable base (e.g. triethylamine, potassium tert-butoxide, sodium hydride etc.) in suitable polar aprotic solvent (e.g, dimethylformamide, tetrahydrofuran etc.). Halogenation of intermediate of formula (11) with suitable halogenating agents [e.g., N-Iodosuccinimide (NIS), N-Bromosuccinimide (NBS), Iodine and Ceric ammonium nitrate (CAN) etc.] in suitable polar aprotic solvents (e.g., acetonitrile, tetrahydrofuran etc.) affords intermediate of formula (12) (where L is halogen) which, in turn, subjected to palladium (0) catalyzed C—C coupling (e.g, Suzuki coupling) reactions with appropriate boronic acid of formula (5) gives compound of general formula (I).

Scheme 3:

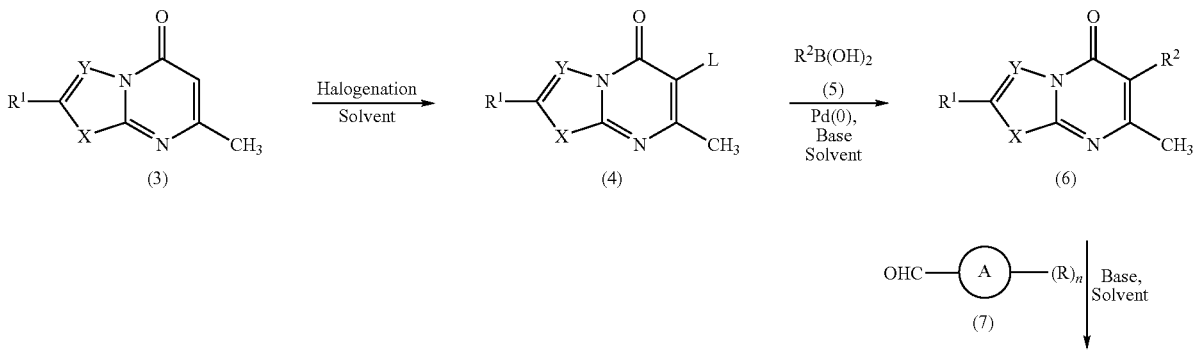

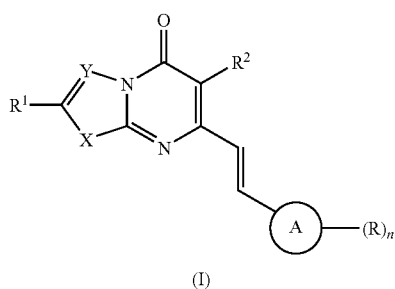

(I)

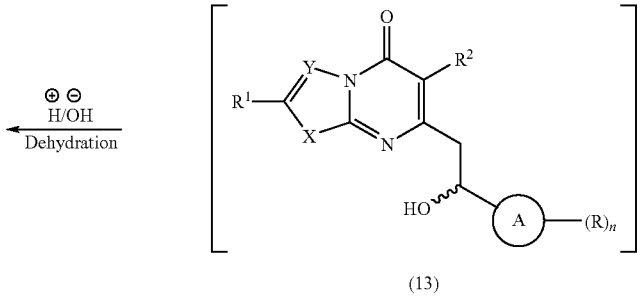

(13)

According to another embodiment, a compound of formula (I) is prepared by the process described in scheme 3. Halogenation of intermediate of formula (3) with suitable halogenating agents [e.g., N-Iodosuccinimide (NIS), N-Bromosuccinimide (NBS), Iodine and Ceric ammonium nitrate (CAN) etc.] in suitable polar aprotic solvents (e.g., acetonitrile, tetrahydrofuran etc.) affords halogenated compound of a formula (4) (where L is halogen) which, in turn, subjected to palladium (0) catalyzed C—C coupling (e.g, Suzuki coupling) reactions with appropriate boronic acid of formula (5) gives intermediate of formula (6). Compound of formula (6) is then converted into alcohol of formula (13) by reaction with appropriate aldehyde of formula (7) and in the presence of suitable base [e.g. lithium diisopropylamide (LDA), lithium hexamethyldisilazide (LHMDS), sodium hydride etc.) in suitable polar solvent (e.g, tetrahydrofuran). Dehydration of resulting alcohol of formula (13) with suitable dehydrating agent (e.g. trifluoroacetic acid) gives compound of general formula (I), according to methods known in the art (Philipova, P. et al. *J. Het. Chem.*, (2006), 43, 1057-1063).

According to another embodiment, a compound of formula (III) is prepared by the process described in scheme 4. Amine of general (14) is converted into compound of formula (15) by reacting with compound of formula (2) (where R' is H or alkyl), in the presence of suitable solvent e.g. acetic acid, polyphosphoric acid etc. (Hermecz, I. et al. *Synthesis.*, (1984), 155-158). Halogenation of intermediate of formula (15) with suitable halogenating agents [e.g., N-Iodosuccinimide (NIS), N-Bromosuccinimide (NBS), Iodine and Ceric ammonium nitrate (CAN) etc.] in suitable polar aprotic solvents (e.g., acetonitrile, tetrahydrofuran etc.) affords halogenated compound of formula (16) (where L is halogen) which, in turn, subjected to palladium (0) catalyzed C—C coupling (e.g, Suzuki coupling) reactions with appropriate boronic acid of formula (5b) gives intermediate of formula (17). Intermediate of formula (17) is then converted into compound of general formula (III) by classical modified Knoevenagel reaction with appropriate aldehyde of formula (7a) in the presence of suitable base (e.g. sodium acetate, sodium ethoxide, potassium tert-butoxide, sodium hydride etc.) in suitable polar solvent (e.g, ethanol, dimethylformamide, tetrahydrofuran etc.).

Scheme 4:

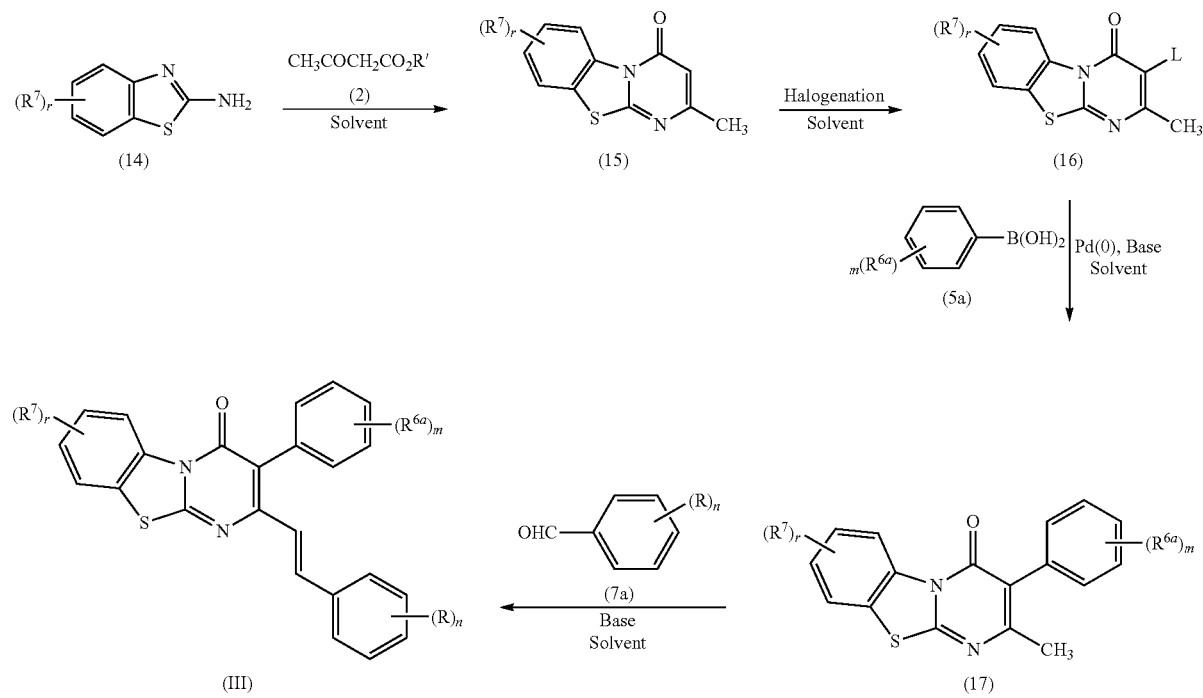

Scheme 5:
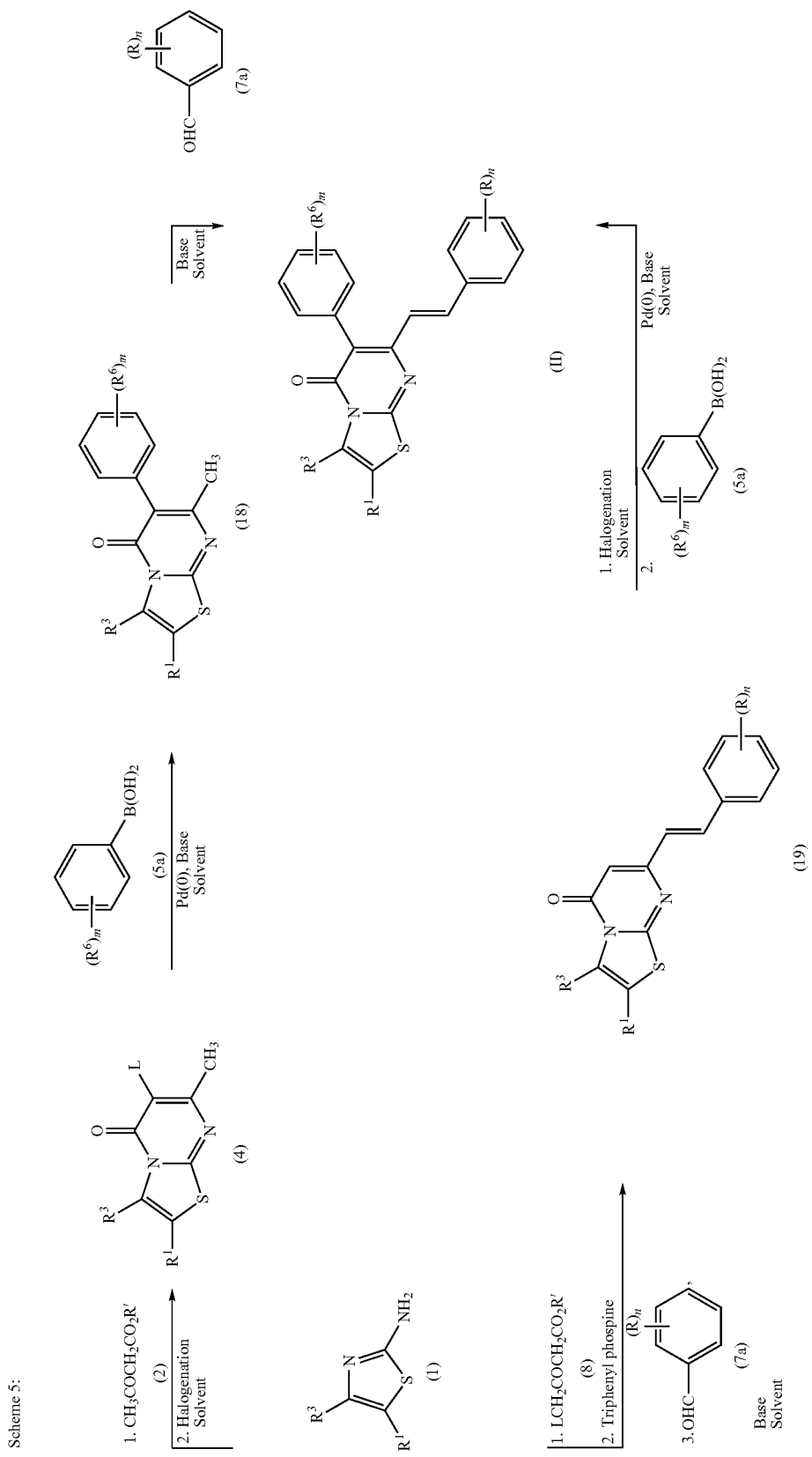

Specific compounds pertaining to this invention are prepared by the process depicted in scheme 5. Amine of a general formula (1) is converted into compound of formula (4) by reacting with compound of formula (2) (where R' is H or alkyl), according to process described in scheme 1. Compound of formula (4), in turn, subjected to palladium (0) catalyzed C—C coupling (e.g., Suzuki coupling) reactions with appropriately substituted arylboronic acid of formula (5b) give compound of formula (18). Compound of formula (18) is then converted into compound of general formula (II) by classical modified Knoevenagel reaction with appropriately substituted aromatic aldehyde of formula (7a), in the presence of suitable base (e.g. sodium acetate, sodium ethoxide, potassium tert-butoxide, sodium hydride etc.) and in suitable polar solvent (e.g, ethanol, dimethylformamide, tetrahydrofuran etc.).

Alternatively, amine of general formula (1) is converted into compound of formula (19) according to process described in Scheme 2 using appropriately substituted aromatic aldehyde of formula (7a). Halogenation of intermediate of formula (19) with suitable halogenating agents [e.g., N-Iodosuccinimide (NIS), N-Bromosuccinimide (NBS), Iodine and Ceric ammonium nitrate (CAN) etc.] in suitable polar aprotic solvents (e.g., acetonitrile, tetrahydrofuran etc.) followed by palladium (0) catalyzed C—C coupling (e.g, Suzuki coupling) reactions with appropriately substituted arylboronic acid of formula (5b) gives compound of a general formula (II).

Scheme 6:
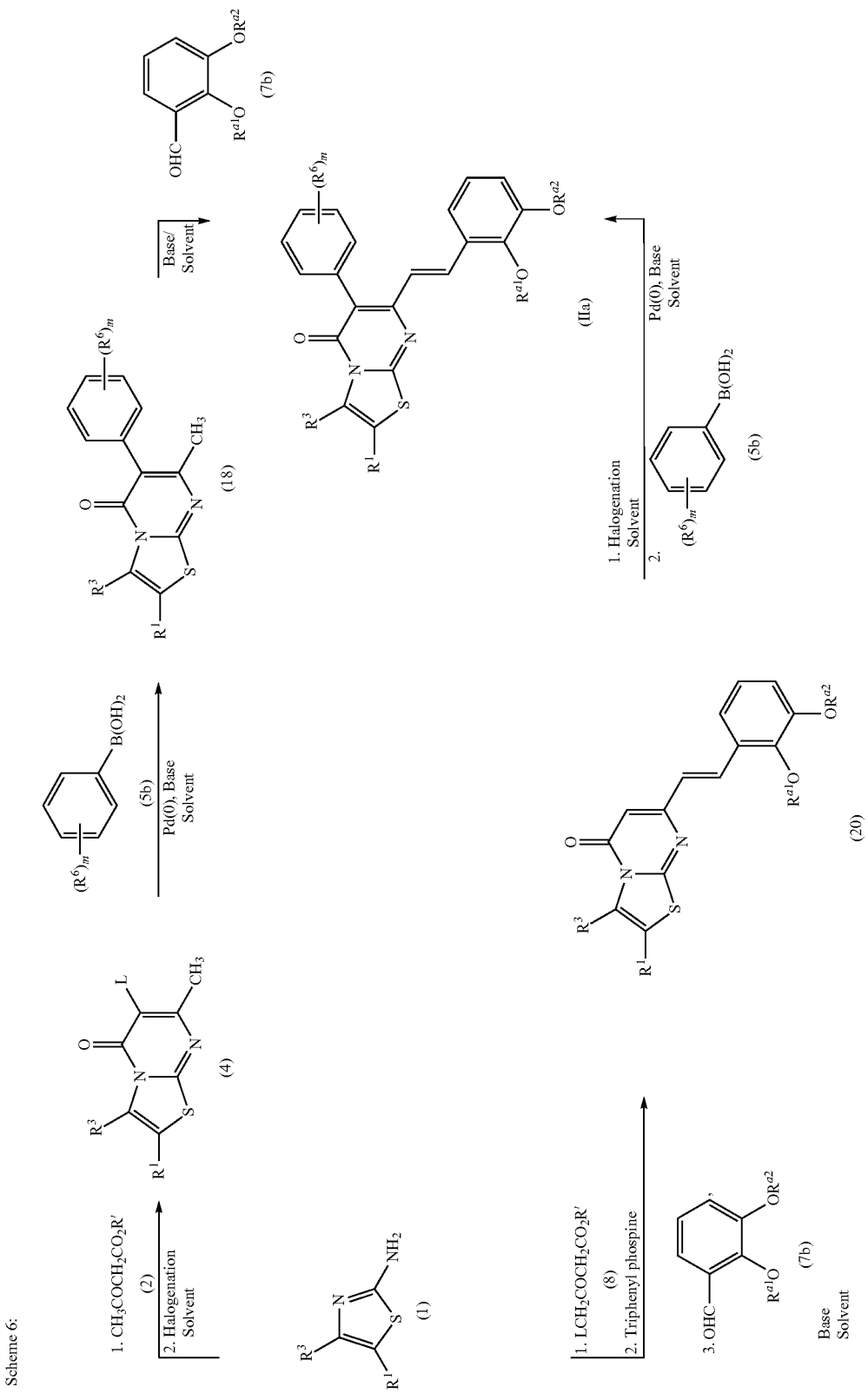

Specific compounds pertaining to this invention are prepared by the process depicted in scheme 6. Amine of a general formula (1) is converted into compound of formula (4) by reacting with compound of formula (2) (where R' is H or alkyl), according to process described in scheme 1. Compound of formula (4), in turn, subjected to palladium (0) catalyzed C—C coupling (e.g., Suzuki coupling) reactions with appropriately substituted arylboronic acid of formula (5b) give compound of formula (18). Compound of formula (18) is then converted into compound of general formula (IIa) by classical modified Knoevenagel reaction with appropriately substituted aromatic aldehyde of formula (7b), in the presence of suitable base (e.g. sodium acetate, sodium ethoxide, potassium tert-butoxide, sodium hydride etc.) and in suitable polar solvent (e.g, ethanol, dimethylformamide, tetrahydrofuran etc.).

Alternatively, amine of general formula (1) is converted into compound of formula (20) according to process described in Scheme 2 using appropriately substituted aromatic aldehyde of formula (7b). Halogenation of intermediate of formula (20) with suitable halogenating agents [e.g., N-Iodosuccinimide (NIS), N-Bromosuccinimide (NBS), Iodine and Ceric ammonium nitrate (CAN) etc.] in suitable polar aprotic solvents (e.g., acetonitrile, tetrahydrofuran etc.) followed by palladium (0) catalyzed C—C coupling (e.g, Suzuki coupling) reactions with appropriately substituted arylboronic acid of formula (5a) gives compound of a general formula (IIa).

Further, specific compounds pertaining to this invention are prepared by the process depicted in Scheme 7. O-dealkylation of compound of a general formula (IIa) under acidic condition (e.g. mixture of 48% hydrobromic acid and acetic acid) or using Lewis acid (e.g. Boron tribromide) affords dihydroxy compound of general formula (21). Alkylation of compound of formula (21) with suitable alkyl halide of formula $R^{a1}X$ using suitable base (e.g. potassium carbonate, sodium hydride, cesium carbonate etc.) and in suitable polar solvent (e.g, dimethylformamide, tetrahydrofuran, dimethyl sulfoxide etc.) affords compound of formula (22). Compound of formula (22) is then converted into compound of general formula (IIa) by alkylation with suitable alkyl halide of formula $R^{a2}X$ using suitable base (e.g. potassium carbonate, sodium hydride, cesium carbonate etc.) and in suitable polar solvent (e.g, dimethylformamide, tetrahydrofuran, dimethyl sulfoxide etc.). Alternatively, compound of formula (21) and (22) can be prepared by classical modified Knoevenagel reaction, specifically with mono- or dihydroxyaldehyde of formula (7b), in the presence of suitable base (e.g. sodium acetate, sodium ethoxide, potassium tert-butoxide, sodium hydride etc.) and in suitable polar solvent (e.g, ethanol, dimethylformamide, tetrahydrofuran etc.) as depicted in scheme 6.

Scheme-7:

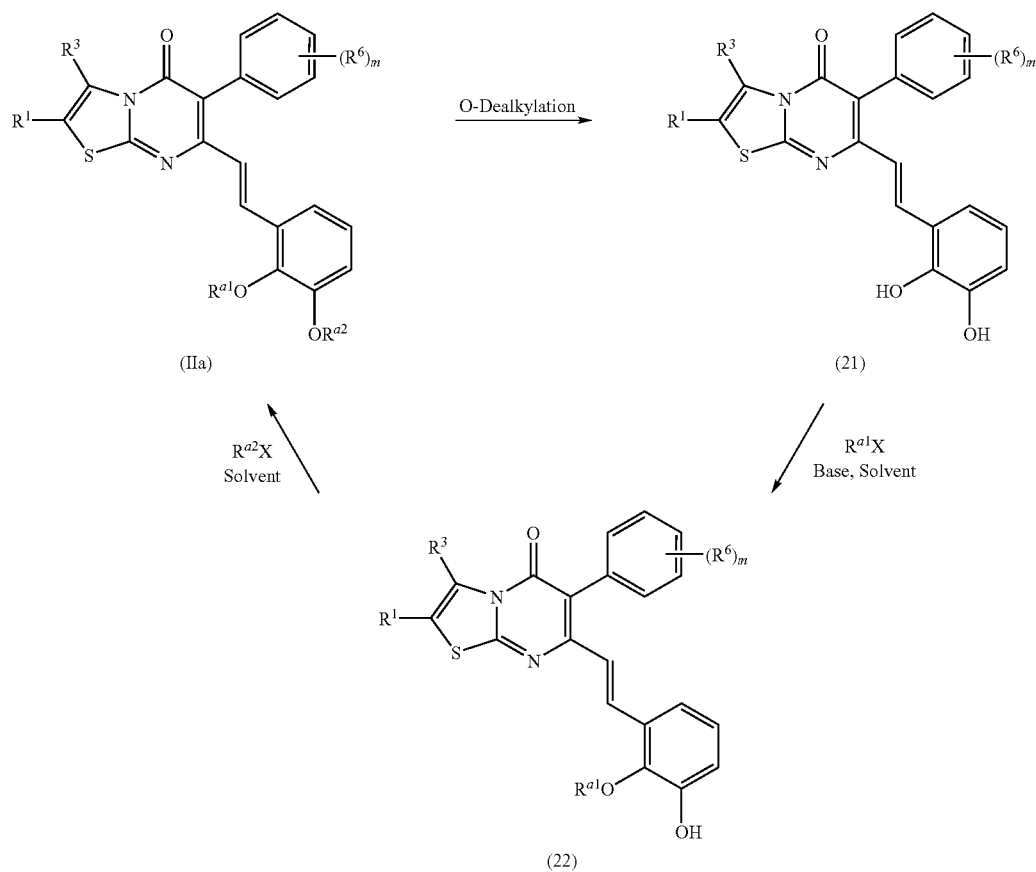

Experimental

Intermediate 1: 7-[(E)-2-(4-Chlorophenyl)vinyl]-6-iodo-5H-[1,3]thiazolo[3,2-a]pyrimidin-5-one Step 1: 7-Methyl-5H-[1,3]thiazolo[3,2-a]pyrimidin-5-one: To a stirred solution of 2-aminothiazole (5 g, 49.931 mmol) in acetic acid (40 ml) was added ethyl acetoacetate (9.48 ml, 74.843 mmol) at room temperature. The reaction mixture was heated to reflux for 12 h under nitrogen. The reaction mixture was cooled to room temperature. The residue obtained after concentration under reduced pressure was basified with saturated $NaHCO_3$ solution and diluted with ethyl acetate (50 ml). The organic layer was washed with brine (100 ml), dried ($Na_2SO_4$) and concentrated to afford a crude product which was purified by silica gel column chromatography using 1% methanol in chloroform to give 3.3 g of the product as a white solid; $^1$H NMR (300 MHz, $CDCl_3$) δ 2.38 (s, 3H), 6.15 (s, 1H), 6.95 (d, J=4.8 Hz, 1H), 7.94 (d, J=4.8 Hz, 1H).

Step 2: 7-[(E)-2-(4-Chlorophenyl)vinyl]-5H-[1,3]thiazolo[3,2-a]pyrimidin-5-one: To a stirred solution of Step 1 intermediate (200 mg, 1.206 mmol) in ethanol (30 ml) was added 4-chlorobenzaldehyde (253 mg, 1.795 mmol) followed by sodium ethoxide (122 mg, 1.795 mmol) in ethanol at room temperature. The reaction mixture was heated to reflux for 12 h. The reaction mixture was allowed to cool to room temperature and concentrated under reduced pressure. The residue obtained was partitioned between chloroform (100 ml) and water (50 ml). The organic layer was washed with brine (100 ml), dried ($Na_2SO_4$) and concentrated to afford a crude product which was purified by silica gel column chromatography using 2% acetone in chloroform to give 59 mg of the product as a white solid; $^1$H NMR (300 MHz, $CDCl_3$) δ 6.25 (s, 1H), 6.87 (d, J=15.6 Hz, 1H), 6.94 (d, J=4.8 Hz, 1H), 7.33 (d, J=9.0 Hz, 2H), 7.49 (d, J=8.4 Hz, 2H), 7.73 (d, J=15.6 Hz, 1H), 7.90 (d, J=4.8 Hz, 1H); ESI-MS (m/z) 289.37 (M+H)$^+$.

Step 3: 7-[(E)-2-(4-Chlorophenyl)vinyl]-6-iodo-5H-[1,3]thiazolo[3,2-a]pyrimidin-5-one A mixture of Step 2 intermediate (3.0 g, 0.018 mmol), iodine (2.75 g, 0.018 mmol) and ceric ammonium nitrate (CAN) (4.93 g, 0.009 mmol) in $CH_3CN$ (30 ml) was stirred at 80° C. for 2 h. The reaction mixture was allowed to cool to room temperature. Distilled water (50 ml) was added to the residue obtained after concentration of the reaction mixture and stirred at room temperature for 1 h. The reaction mixture was filtered, dried under vacuum to give 5.30 g of the product as a light yellow solid; $^1$H NMR (300 MHz, $CDCl_3$) δ 6.87 (d, J=15.6 Hz, 1H), 6.94 (d, J=4.8 Hz, 1H), 7.33 (d, J=9.0 Hz, 2H), 7.49 (d, J=8.4 Hz, 2H), 7.73 (d, J=15.6 Hz, 1H), 7.90 (d, J=4.8 Hz, 1H); ESI-MS (m/z) 289.37 (M+H)$^+$.

Intermediate 2: 7-{(E)-2-[2-(Cyclopropylmethoxy)-3-methoxyphenyl]vinyl}-6-iodo-5H-[1,3]thiazolo[3,2-a]pyrimidin-5-one Step 1: 7-(Chloromethyl)-5H-[1,3]thiazolo[3,2-a]pyrimidin-5-one: A solution of 2-aminothiazole (5.0 g, 49.993 mmol) in polyphosphoric acid (40.0 g) was treated with ethyl chloroacetoacetate (11.176 g, 67.866 mmol) and heated at 110° C. for 5.0 h. The reaction mixture was cooled to room temperature and adjusted to pH 7 with 10% aq. NaOH. The solid formed was filtered and purified by column chromatography using ethyl acetate in dichloromethane as solvent to afford 2.6 g of the desired compound as a brown solid: $^1$H NMR (300 MHz, DMSO-$d_6$) δ 4.59 (s, 2H), 6.41 (s, 1H), 7.56 (d, J=4.8 Hz, 1H), 8.03 (d, J=4.8 Hz, 1H); ESI-MS (m/z) 200.42 (M+H)$^+$.

Step 2: 5-oxo-5H-[1,3]thiazolo[3,2-a]pyrimidin-7-ylmethyl(triphenyl)phosphonium chloride: To a stirred suspension of Step 1 intermediate (6.0 g, 29.90 mmol) in acetonitrile was added triphenylphosphine (8.6 g, 32.89 mmol) at room temperature. The resulting reaction mixture was slowly heated to reflux for 30 min. The solvent was concentrated in vacuo and the residue stirred with diisopropyl ethyl ether and filtered. The solid was dried under vacuum to afford 13.5 g of the desired compound as an off-white solid: $^1$H NMR (300 MHz, DMSO-$d_6$) δ 4.96 (d, J=15.0 Hz, 2H), 6.15 (br s, 1H), 7.32 (br s, 1H), 7.60-7.74 (m, 15H), 7.86 (br s, 1H); ESI-MS (m/z) 427.33 (M+H)$^+$.

Step 3: 7-{(E)-2-[2-(Cyclopropylmethoxy)-3-methoxyphenyl]vinyl}-5H-[1,3]thiazolo[3,2-a]pyrimidin-5-one: To a stirred suspension of Step 2 intermediate (13.0 g, 28.08) was added NaH (1.2 g, 30.88) in dry DMSO (75 ml) and stirred for 0.5 h. A solution of 2-(cyclopropylmethoxy)-3-methoxybenzaldehyde (6.3 g, 30.88 mmol) in DMSO was added dropwise to this solution at room temperature and stirred for 2 h. The reaction mixture was diluted with ethyl acetate, washed with water and brine, dried over anhydrous $Na_2SO_4$ to yield a crude solid which was purified by column chromatography using 10% ethyl acetate in DCM to afford 7.5 g of the desired compound as a white solid: $^1$H NMR (300 MHz, DMSO-$d_6$) δ 0.30-0.33 (m, 2H), 0.52-057 (m, 2H), 1.10-1.20 (br m, 1H), 3.72-3.90 (m, 5H), 6.29 (s, 1H), 7.00-7.11 (m, 3H), 7.34 (d, J=6.3 Hz, 1H), 7.44-7.50 (m, 1H), 7.90-8.00 (m, 1H), 8.14 (d, J=6.2 Hz, 1H); ESI-MS (m/z) 355.17 (M+H)$^+$ Step 4: 7-{(E)-2-[2-(Cyclopropylmethoxy)-3-methoxyphenyl]vinyl}-6-iodo-5H-[1,3]thiazolo[3,2-a]pyrimidin-5-one: To a solution of Step 3 intermediate (3.89 g, 10.72 mmol) was added N-iodosuccinimide (2.69 g, 11.79 mmol) in acetonitrile at room temperature. The reaction temperature was then raised to 60° C. and stirred for 4 h. The reaction mixture was then cooled to room temperature, diluted with water and stirred for 20 min. The filtered solid was washed with water and dried to afford 5.19 g of the desired compound; $^1$H NMR (300 MHz, $CDCl_3$) δ 0.32-0.33 (m, 2H), 0.54-0.56 (d, J=7.2 Hz, 2H), 1.22 (br s, 1H), 3.77-3.81 (m, 5H), 7.06-7.14 (m, 2H), 7.27-7.29 (d, J=7.2 Hz, 1H), 7.49-7.52 (m, 1H), 7.57 (s, 1H), 7.96 (d, J=3.9 Hz, 1H), 8.18 (d, J=15.6 Hz, 1H); ESI-MS (m/z) 481.45 (M+H)$^+$.

Intermediate 3: 6-(3,5-Difluorophenyl)-7-methyl-5H-[1,3]thiazolo[3,2-a]pyrimidin-5-one Step 1: 7-Methyl-5H-[1,3]thiazolo[3,2-a]pyrimidin-5-one: To a stirred solution of 2-aminothiazole (5.0 g, 49.930 mmol) in acetic acid (40 ml) was added ethyl acetoacetate (9.746 g, 74.90 mmol) at room temperature. The reaction mixture was heated to reflux for 12 h under nitrogen. The reaction mixture was allowed to cool to room temperature. The residue obtained after concentration of the reaction mixture was basified with saturated solution of sodium bicarbonate and diluted with ethyl acetate (500 ml). The organic layer was washed with brine, dried over anhydrous $Na_2SO_4$ and concentrated to afford a crude product which was purified by silica gel column chromatography using 1% methanol in chloroform to give 4.20 g of the product as a white solid; $^1$H NMR (300 MHz, $CDCl_3$) δ 2.38 (s, 3H), 6.15 (s, 1H), 6.95 (d, J=4.8 Hz, 1H), 7.94 (d, J=4.8 Hz, 1H).

Step 2: 6-Iodo-7-methyl-5H-[1,3]thiazolo[3,2-a]pyrimidin-5-one: A stirred solution of Step 1 Intermediate (20 g, 120.463 mmol) in acetonitrile (200 ml) was treated with ceric ammonium nitrate (33 g, 60.233 mmol) and iodine (18 g, 72.281 mmol) at room temperature according to the procedure outlined in Intermediate 1, Step 3 to give 35 g of the product as a light yellow solid; $^1$H NMR (300 MHz, DMSO-d$_6$) δ 2.56 (s, 3H), 7.52 (d, J=5.1 Hz, 1H), 7.97 (d, J=4.8 Hz, 1H); ESI-MS (m/z) 291.29 (M−H)$^-$.

Step 3: 6-(3,5-Difluorophenyl)-7-methyl-5H-[1,3]thiazolo[3,2-a]pyrimidin-5-one: To a solution of Step 2 intermediate (0.300 g, 1.027 mmol) in toluene (10 ml) was added Pd[(C$_6$H$_5$)$_3$P]$_4$ [tetrakis(triphenylphosphine)palladium(0)] (0.048 g. 0.042 mmol) and a solution of Na$_2$CO$_3$ (0.653 g, 6.162 mmol) in water (4 ml). A solution of 3,5-difluorophenylboronic acid (6.5 g, 44.235 mmol) in ethanol (6 ml) was added to the reaction mixture and it was refluxed for 1.5 h. After completion of the reaction mixture, the solvent was concentrated in vacuo, the residue partitioned between ethyl acetate (200 ml) and water (50 ml). The organic layer was washed with brine (50 ml) and dried over anhydrous Na$_2$SO$_4$ to afford a crude product which was purified by silica gel column chromatography using 10% ethyl acetate in chloroform to give 280 mg of the product as an off-white solid; $^1$H NMR (300 MHz, DMSO-d$_6$) δ 2.19 (s, 3H), 7.53 (d, J=7.8 Hz, 3H), 7.88 (d, J=7.8 Hz, 1H) 8.02 (d, J=4.8 Hz, 1H); ESI-MS (m/z) 276.31 (M−H)$^-$.

Intermediate 4: 4-(7-Methyl-5-oxo-5H-[1,3]thiazolo[3,2-a]pyrimidin-6-yl)benzonitrile Step 1: 7-Methyl-5H-[1,3]thiazolo[3,2-a]pyrimidin-5-one: A solution of 2-aminothiazole (50 g, 499.301 mmol), ethyl acetoacetate (96 ml, 748.885 mmol) and acetic acid (400 ml) was reacted together according to the procedure described in Intermediate 3, Step 1 to afford a crude product which was purified by silica gel column chromatography using 1% methanol in chloroform to give 40 g of the product as a white solid; $^1$H NMR (300 MHz, CDCl$_3$) δ 2.38 (s, 3H), 6.15 (s, 1H), 6.95 (d, J=4.8 Hz, 1H), 7.94 (d, J=4.8 Hz, 1H).

Step 2: 6-Iodo-7-methyl-5H-[1,3]thiazolo[3,2-a]pyrimidin-5-one: A stirred solution of the Step 1 intermediate (20 g, 120.463 mmol) in acetonitrile (200 ml) was reacted with ceric ammonium nitrate (33 g, 60.233 mmol) followed by iodine (18 g, 72.281 mmol) according to the procedure described in Intermediate 1, Step 3 to give 35 g of the product as a light yellow solid; $^1$H NMR (300 MHz, DMSO-d$_6$) δ 2.56 (s, 3H), 7.52 (d, J=5.1 Hz, 1H), 7.97 (d, J=4.8 Hz, 1H); ESI-MS (m/z) 291.29 (M−H)$^-$.

Step 3: 4-(7-Methyl-5-oxo-5H-[1,3]thiazolo[3,2-a]pyrimidin-6-yl)benzonitrile: This compound was prepared from Step 2 intermediate (10 g, 34.234 mmol), 4-cyanophenylboronic acid (6.5 g, 44.235 mmol), Pd[(C$_6$H$_5$)$_3$P]$_4$ (1.62 g, 1.401 mmol) and Na$_2$CO$_3$ (21.7 g, 2.051 mmol) in a mixture of toluene (250 ml), ethanol (150 ml) and water (100 ml) according to the procedure described in Intermediate 3, Step 3 to afford a crude product which was purified by silica gel column chromatography using 10% ethyl acetate in chloroform to give 5 g of the product as a light yellow solid; $^1$H NMR (300 MHz, DMSO-d$_6$) δ 2.19 (s, 3H), 7.53 (d, J=7.8 Hz, 3H), 7.88 (d, J=7.8 Hz, 2H) 8.02 (d, J=4.8 Hz, 1H); ESI-MS (m/z) 265.31 (M−H)$^-$.

Intermediate 5: 7-Methyl-6-[4-(trifluoromethyl)phenyl]-5H-[1,3]thiazolo[3,2-a]pyrimidin-5-one The title compound was prepared by coupling reaction of Step 2 intermediate from Intermediate 4 (10.9 g, 37.312 mmol) with 4-(trifluoromethyl)phenyl boronic acid (9.9 g, 52.241 mmol) in the presence of Pd[(C$_6$H$_5$)$_3$P]$_4$ (1.72 g, 1.491 mmol) and sodium carbonate (23.7 g, 223.891 mol) in a mixture of toluene, ethanol and water according to the procedure described in Intermediate 3, step 3 yielded 18.5 g of the desired compound as a light yellow solid; $^1$H NMR (300 MHz, DMSO-d$_6$) δ 2.18 (s, 3H), 7.53-7.59 (m, 4H), 7.58-7.80 (m, 1H), 8.01 (d, J=4.8 Hz, 1H); ESI-MS (m/z) 311.28 (M+H)$^+$.

Intermediate 6: 7-Methyl-6-[3-(trifluoromethyl)phenyl]-5H-[1,3]thiazolo[3,2-a]pyrimidin-5-one The title compound was prepared by coupling reaction of Step 2 intermediate from Intermediate 4 (600 mg, 2.001 mmol) with 3-(trifluoromethyl)phenyl boronic acid (585 g, 3.020 mmol) in the presence of Pd[(C$_6$H$_5$)$_3$P]$_4$ (92 mg, 0.0812 mmol) and sodium carbonate (1.27 g, 12.061 mol) in a mixture of toluene, ethanol and water according to the procedure described in Intermediate 3, step 3 1.21 g yielded 18.5 g of the desired compound as a light yellow solid; $^1$H NMR (300 MHz, DMSO-d$_6$) δ 2.18 (s, 3H), 7.53-7.59 (m, 4H), 7.58-7.80 (m, 1H), 8.01 (d, J=4.8 Hz, 1H); ESI-MS (m/z) 311.28 (M+H)$^+$.

Intermediate 7: 6-Iodo-7-[(E)-2-(2-isobutoxy-3-methoxyphenyl)vinyl]-5H-[1,3]thiazolo-[3,2-a]pyrimidin-5-one Step 1: 7-[(E)-2-(2-Isobutoxy-3-methoxyphenyl)vinyl]-5H-[1,3]thiazolo[3,2-a]pyrimidin-5-one: This compound was prepared using Step 2 intermediate from Intermediate 2 (1.00 g, 2.160 mmol), (2-isobutoxy-3-methoxy)benzaldehyde (494 mg, 2.376 mmol) and NaH (95 mg, 3.958 mmol) in dry DMSO (10 ml) according to the procedure outlined in Intermediate 2, Step 3 to yield a crude residue which was purified by column chromatography using 2% ethyl acetate in DCM to afford the 500 mg of the desired compound as a white solid: $^1$H NMR (300 MHz, DMSO-d$_6$) 1.05 (d, J=6.9 Hz, 6H), 2.01-2.06 (m, 1H), 3.69 (d, J=6.3 Hz, 2H), 3.80 (s, 3H), 6.28 (s, 1H), 6.94-7.18 (m, 3H), 7.34 (d, J=6.3 Hz, 1H), 7.47 (d, J=5.1 Hz, 1H), 7.97 (d, J=4.8 Hz, 1H), 8.09 (d, J=16.2 Hz, 1H).

Step 2: 6-Iodo-7-[(E)-2-(2-isobutoxy-3-methoxyphenyl)vinyl]-5H-[1,3]thiazolo[3,2-a]pyrimidin-5-one: A solution of Step 1 intermediate (600 mg, 1.683 mmol) was treated with N-iodosuccinimide (416 g, 1.851 mmol) in acetonitrile (10 ml) according to the procedure described in Step 4 of Intermediate 2 to afford 600 mg of the desired compound as a yellow solid; $^1$H NMR (300 MHz, DMSO-d$_6$) 1.05 (d, J=6.9 Hz, 6H), 2.04-2.08 (m, 1H), 3.71 (d, J=6.3 Hz, 2H), 3.81 (s, 3H), 7.10-7.12 (m, 2H), 7.27-7.30 (m, 1H), 7.48-7.53 (m, 2H), 7.96 (d, J=4.8 Hz, 1H), 8.17 (d, J=15.6 Hz, 1H); ESI-MS (m/z) 483.16 (M+H)$^+$.

Intermediate 8: 7-{(E)-2-[2-(2,2-Dimethylpropoxy)-3-methoxyphenyl]vinyl}-6-iodo-5H-[1,3]thiazolo-[3,2-a]pyrimidin-5-one Step 1: 7-{(E)-2-[2-(2,2-Dimethylpropoxy)-3-methoxyphenyl]vinyl}-5H-[1,3]thiazolo-[1,2-a]pyrimidin-5-one: This compound was prepared using Step 2 intermediate from Intermediate 2 (1.00 g, 2.160 mmol), [2-(2,2-dimethylpropoxy)-3-methoxy)]benzaldehyde (527 mg, 2.316 mmol) and NaH (92 mg, 2.685 mmol) in dry DMSO (10 ml) according to the procedure outlined in Intermediate 2, Step 3 to yield a crude residue which was purified by column chromatography using 2% ethyl acetate in chloroform to afford the 1.416 g of the desired compound as a white solid: $^1$H NMR (300 MHz, DMSO-$d_6$) 1.08 (s, 9H), 3.56 (s, 2H), 3.79 (s, 3H), 6.26 (s, 1H), 7.01-7.17 (m, 2H), 7.33-7.35 (m, 1H), 7.46 (d, J=4.8 Hz, 1H), 7.97 (d, J=4.8 Hz, 1H), 8.11-8.16 (m, 1H); ESI-MS (m/z) 371.52 (M+H)$^+$.

Step 2: 7-{(E)-2-[2-(2,2-Dimethylpropoxy)-3-methoxyphenyl]vinyl}-6-iodo-5H-[1,3]thiazolo[3,2-a]pyrimidin-5-one: A solution of Step 1 intermediate (275 mg, 5.816 mmol) was treated with N-iodosuccinimide (143 g, 6.327 mmol) in acetonitrile (10 ml) according to the procedure described in Step 4 of Intermediate 2 to afford a crude product which was purified by column chromatography using 2% ethyl acetate in chloroform as eluent to afford 510 mg of the desired compound as a yellow solid; $^1$H NMR (300 MHz, DMSO-$d_6$) 1.08 (s, 9H), 3.58 (m, 2H), 3.81 (m, 3H), 7.07-7.12 (m, 2H), 7.30-7.33 (m, 2H), 7.41-7.48 (m, 1H), 7.94-7.96 (m, 1H), 8.23-8.29 (m, 1H); ESI-MS (m/z) 497.21 (M+H)$^+$.

Intermediate 9: 6-(4-Methoxyphenyl)-7-methyl-5H-[1,3]thiazolo[3,2-a]pyrimidin-5-one The title compound was prepared by coupling reaction of Step 2 intermediate from Intermediate 4 (6.8 g, 23.271 mmol) with 4-methoxyphenylboronic acid (4.95 g, 32.490 mmol) in the presence of Pd[($C_6H_5$)$_3$P]$_4$ (1.076 g, 0.931 mmol) and sodium carbonate (14.812 g, 139.071 mmol) in a mixture of toluene, ethanol and water according to the procedure described in Intermediate 3, step 3 yielded 5.0 g of the desired compound as an off-white solid; $^1$H NMR (300 MHz, DMSO-$d_6$) δ 2.29 (s, 3H), 3.83 (s, 3H), 6.92-6.96 (m, 3H), 7.20-7.23 (m, 2H), 7.94 (d, J=4.8 Hz, 1H); ESI-MS (m/z) 273.51 (M+H)$^+$.

Intermediate 10: 6-(4-Ethoxyphenyl)-7-methyl-5H-[1,3]thiazolo[3,2-a]pyrimidin-5-one Step 1: 6-(4-Hydroxyphenyl)-7-methyl-5H-[1,3]thiazolo[3,2-a]pyrimidin-5-one: Intermediate 9 (4.8 g, 17.726 mmol) was treated with HBr (35 ml) and acetic acid (35 ml) at room temperature and the reaction mixture was then heated to reflux overnight for 15.0 g. After completion of the reaction, the mixture was concentrated and basified with NaHCO$_3$ and extracted with ethyl acetate. Combined organic layer was washed with water, brine, dried over anhydrous Na$_2$SO$_4$ purified using 5% CH$_3$OH in chloroform to afford 3.0 g of the desired compound; $^1$H NMR (300 MHz, DMSO-$d_6$) δ 2.17 (s, 3H), 6.76-6.79 (m, 2H), 7.05-7.08 (m, 2H), 7.48 (d, J=4.8 Hz, 1H), 7.96 (d, J=5.1 Hz, 1H), 9.47 (s, 1H); ESI-MS (m/z) 259.50 (M+H)$^+$.

Step 2: 6-(4-Ethoxyphenyl)-7-methyl-5H-[1,3]thiazolo[3,2-a]pyrimidin-5-one: To a solution of Step 1 intermediate (250 mg, 0.967 mmol) in DMF (4 ml) was added ethyl bromide (0.147 g, 1.355 mmol) and NaH (0.053 g, 1.355 mmol) and heated to 80° C. for 15.0 h. After completion of the reaction, the mixture was diluted with ethyl acetate, washed with water, brine, dried over anhydrous Na$_2$SO$_4$ to afford 300 mg of the desired compound as a white solid; $^1$H NMR (300 MHz, DMSO-$d_6$) δ 1.34 (t, J=6.6 Hz, 3H), 2.17 (s, 3H), 4.05 (q, J=6.6 Hz, 2H), 6.93-6.96 (m, 2H), 7.17-7.20 (m, 2H), 7.50 (d, J=4.5 Hz, 1H), 7.98 (d, J=4.8 Hz, 1H); ESI-MS (m/z) 311.28 (M+H)$^+$.

Intermediate 11: 7-Methyl-6-[4-(2,2,2-trifluoroethoxy)phenyl]-5H-[1,3]thiazolo[3,2-a]-pyrimidin-5-one To a solution of Step 1 intermediate from Intermediate 10 (400 mg, 2.712 mmol) in DMF (4 ml) was added 1,1,1-trifluoro-2-iodoethane (1.131 g, 5.413 mmol) at room temperature followed by Cs$_2$CO$_3$ (2.63 g, 8.120 mmol) and the reaction temperature was heated to 80° C. for 15.0 h overnight. The reaction mixture was diluted with ethyl acetate, washed with water and brine and purified by column chromatography using 1% methanol in chloroform to afford the desired compound; $^1$H NMR (300 MHz, CDCl$_3$) δ 2.17 (s, 3H), 4.79 (q, J=9.3 Hz, 2H), 7.07-7.10 (m, 2H), 7.24-7.27 (m, 2H), 7.50 (d, J=4.8 Hz, 1H), 7.98 (d, J=4.5 Hz, 1H).

Intermediate 12: 4-[4-(7-Methyl-5-oxo-5H-[1,3]thiazolo[3,2-a]pyrimidin-6-yl)phenoxy]-butane nitrile To a solution of Step 1 intermediate, Intermediate 10 (350 mg, 1.355 mmol) in DMF (10 ml) was added 4-bromobutyronitrile (280 mg, 1.897 mmol) at room temperature followed by K$_2$CO$_3$ (560 mg, 4.065 mmol) and the reaction temperature was heated to 80° C. for 15.0 h overnight. The reaction mixture was diluted with ethyl acetate, washed with water and brine and purified by column chromatography to afford 250 mg the desired compound as a white solid; $^1$H NMR (300 MHz, CDCl$_3$) δ 2.17 (s, 3H), 3.80-3.85 (m, 2H), 7.07-7.10 (m, 2H), 7.24-7.27 (m, 2H), 7.50 (d, J=4.8 Hz, 1H), 7.98 (d, J=4.5 Hz, 1H).

Intermediate 13: 6-(4-Cyclopropylmethoxyphenyl)-7-methyl-5H-[1,3]thiazolo[3,2-a]pyrimidin-5-one To a solution of Step 1 intermediate from Intermediate 10 (500 mg, 1.932 mmol) in DMF (5 ml) was added cyclopropylmethyl bromide (0.313 g, 2.321 mmol) at room temperature followed by Cs$_2$CO$_3$ (1.88 g, 5.770 mmol) and the reaction temperature was heated to 80° C. for 15.0 h overnight. The reaction mixture was diluted with ethyl acetate, washed with water and brine and purified by column chromatography using 1% methanol in chloroform to afford the desired compound; $^1$H NMR (300 MHz, CDCl$_3$) δ 0.35-0.37 (m, 2H), 0.59-0.61 (m, 2H), 1.01-1.03 (m, 1H), 2.19 (s, 3H), 3.80-3.85 (m, 2H), 7.09-7.11 (m, 2H), 7.26-7.29 (m, 2H), 7.52 (d, J=4.8 Hz, 1H), 7.97 (d, J=4.5 Hz, 1H); MS (m/z) 313.25 (M+H)$^+$.

Intermediate 14: 6-[4-(Difluoromethoxy)phenyl]-7-methyl-5H-[1,3]thiazolo[3,2-a]-pyrimidin-5-one A solution of Step 1 intermediate, Intermediate 10 (400 mg, 1.548 mmol) in DMF (15 ml) was treated with Cs$_2$CO$_3$ (1.513 g, 4.645 mmol) slowly at room temperature. The reaction temperature was raised to 80° C. at which the chlorodifluoro-methane (ClCHF$_2$) gas was passed into the reaction mixture till TLC indicated completion of the reaction. The reaction mixture was diluted with ethyl acetate, washed with water and brine, dried over anhydrous Na$_2$SO$_4$ and purified using column chromatography to afford the desired compound; $^1$H NMR (300 MHz, CDCl$_3$) δ 2.20 (s, 3H), 7.18-7.22 (m, 2H), 7.25 (s, 1H), 7.37-7.40 (m, 2H), 7.55 (d, J=5.1 Hz, 1H), 7.99 (d, J=4.8 Hz, 1H); ESI-MS (m/z) 309.45 (M+H)$^+$.

Intermediate 15: 7-Methyl-6-[4-(trifluoromethoxy)phenyl]-5H-[1,3]thiazolo[3,2-a]-pyrimidin-5-one The title compound was prepared by coupling reaction of Step 2 of Intermediate 4 (9.5 g, 37.312 mmol) with 4-(trifluoromethoxy)phenyl boronic acid (9.5 g, 32.523 mmol) in the presence of Pd[($C_6H_5$)$_3$P]$_4$ (1.5 g, 1.301 mmol) and sodium carbonate (20.6 g, 195.13 mol) in a mixture of toluene, ethanol and water according to the procedure described in Intermediate 3, step 3 yielded 7.3 g of the desired compound as a pale yellow solid; IR (KBr) 3088, 1658, 1646, 1513, 1269, 1160 cm$^{-1}$; $^1$H NMR (300 MHz, DMSO-d$_6$) δ 2.18 (s, 3H), 7.42-7.4 (m, 4H), 7.53 (d, J=4.8 Hz, 1H), 8.01 (d, J=4.8 Hz, 1H); ESI-MS (m/z) 327.16 (M+H)$^+$.

Intermediate 16: 7-{(E)-2-[2-(Cyclopropylmethoxy)-3-methoxyphenyl]vinyl}-6-iodo-2-methyl-5H-[1,3]-thiazolo[3,2-a]pyrimidin-5-one Step 1: 7-(Chloromethyl)-2-methyl-5H-[1,3]thiazolo[3,2-a]pyrimidin-5-one: This compound was synthesized from 2-amino-5-methyl thiazole (5.0 g, 43.710 mmol) and ethyl chloroacetoacetate (9.893 g, 59.561 mmol) in polyphosphoric acid (40.0 g) according to the procedure described in Step 1, Intermediate 2 to afford 6.0 g of the desired compound as a black solid; $^1$H NMR (300 MHz, DMSO-d$_6$) δ 2.43 (s, 3H), 4.58 (s, 2H), 6.39 (s, 1H), 7.87 (s, 1H); ESI-MS (m/z) 215.37 (M+H)$^+$.

Step 2: 2-Methyl-5-oxo-5H-[1,3]thiazolo[3,2-a]pyrimidin-7-ylmethyl(triphenyl)-phosphonium chloride: Treatment of Step 1 intermediate (2.0 g, 9.317 mmol) with triphenylphosphine (2.688 g, 10.249 mmol) in acetonitrile (70 ml) according to the procedure described in Step 2, Intermediate 2 afforded 3.5 g of the desired compound: $^1$H NMR (300 MHz, DMSO-d$_6$) δ 2.36 (s, 3H), 2.20-2.26 (m, 2H), 6.17 (s, 1H), 7.71-7.84 (m, 15H); ESI-MS (m/z) 441.37 (M+H)$^+$.

Step 3: 7-{(E)-2-[2-(Cyclopropylmethoxy)-3-methoxyphenyl]vinyl}-2-methyl-5H-[1,3]-thiazolo[3,2-a]pyrimidin-5-one: A stirred suspension of Step 2 intermediate (1.0 g, 2.096 mmol) in dry DMSO (12 ml) was treated with NaH (92 mg, 2.306 mmol) and 2-(cyclopropylmethoxy)-3-methoxybenzaldehyde (475 mg, 2.306 mmol) according to the procedure described in Step 3, Intermediate 2 to yield a crude solid which was purified by column chromatography using 2% ethyl acetate in DCM to afford the 600 mg of the desired compound as an off-white solid; $^1$H NMR (300 MHz, DMSO-d$_6$) δ 0.31-0.32 (m, 2H), 0.53-0.55 (m, 2H), 0.84-0.86 (s, 1H), 2.42 (s, 1H), 3.74-3.76 (m, 2H), 3.79 (s, 3H), 6.25 (s, 1H), 7.00-7.16 (m, 2H), 7.31-7.33 (m, 1H), 7.80 (s, 1H), 8.06-8.11 (m, 1H); ESI-MS (m/z) 369.24 (M+H)$^+$.

Step 4: 7-{(E)-2-[2-(Cyclopropylmethoxy)-3-methoxyphenyl]vinyl}-6-iodo-2-methyl-5H-[1,3]thiazolo[3,2-a]pyrimidin-5-one: To a solution of Step 3 intermediate (700 mg, 1.810 mmol) in acetonitrile (10 ml) was added N-iodosuccinimide (641 mg, 2.841 mmol) and reacted according to the procedure described in Step 4, Intermediate 2 to afford 600 mg of the desired compound; $^1$H NMR (300 MHz, CDCl$_3$) δ 0.31-0.33 (m, 2H), 0.53-0.56 (m, 2H), 1.22 (br s, 1H), 2.43 (s, 3H), 3.76-3.81 (m, 2H), 3.81 (s, 3H), 7.05-7.11 (m, 2H), 7.25-7.28 (m, 1H), 7.51 (d, J=15.6 Hz, 1H), 7.80 (s, 1H), 8.14 (d, J=15.6 Hz, 1H); ESI-MS (m/z) 495.10 (M+H)$^+$.

Intermediate 17: 7-{(E)-2-[2-(Cyclopropylmethoxy)-3-methoxyphenyl]vinyl}-6-iodo-3-methyl-5H-[1,3]-thiazolo[3,2-a]pyrimidin-5-one Step 1: 7-(Chloromethyl)-3-methyl-5H-[1,3]thiazolo[3,2-a]pyrimidin-5-one: This compound was synthesized from 2-amino-4-methyl thiazole (5.0 g, 43.710 mmol) and ethyl chloroacetoacetate (9.893 g, 59.561 mmol) in polyphosphoric acid (40.0 g) according to the procedure described in Step 1, Intermediate 2 to afford 8.0 g of the desired compound as a black solid; $^1$H NMR (300 MHz, DMSO-d$_6$) δ 2.67 (s, 3H), 4.53 (s, 2H), 6.27 (s, 1H), 7.05 (s, 1H); ESI-MS (m/z) 215.39 (M+H)$^+$.

Step 2: 3-Methyl-5-oxo-5H-[1,3]thiazolo[3,2-a]pyrimidin-7-ylmethyl(triphenyl)-phosphonium chloride: Treatment of Step 1 intermediate (2.0 g, 9.317 mmol) with triphenylphosphine (2.688 g, 10.249 mmol) in acetonitrile (70 ml) according to the procedure described in Step 2, Intermediate 2 afforded 4.0 g of the desired compound: $^1$H NMR (300 MHz, DMSO-d$_6$) δ 2.07 (s, 3H), 5.17-5.22 (m, 2H), 6.07 (s, 1H), 7.01 (m, 1H), 7.75-7.85 (m, 15H); ESI-MS (m/z) 441.46 (M+H)$^+$.

Step 3: 7-{(E)-2-[2-(Cyclopropylmethoxy)-3-methoxyphenyl]vinyl}-3-methyl-5H-[1,3]-thiazolo[3,2-a]pyrimidin-5-one: A stirred suspension of Step 2 intermediate (1.0 g, 2.096 mmol) in dry DMSO (12 ml) was treated with NaH (92 mg, 2.306 mmol) and 2-(cyclopropylmethoxy)-3-methoxybenzaldehyde (475 mg, 2.306 mmol) according to the procedure described in Step 3, Intermediate 2 to yield a crude solid which was purified by column chromatography using 2% ethyl acetate in DCM to afford 260 mg of the desired compound as an off-white solid; $^1$H NMR (300 MHz, DMSO-d$_6$) δ 0.31-0.32 (m, 2H), 0.53-0.55 (m, 2H), 1.18-1.22 (m, 1H), 2.66 (s, 3H), 3.73-3.76 (m, 2H), 3.79 (s, 3H), 6.15 (s, 1H), 6.97-7.13 (m, 4H), 7.30-7.33 (m, 1H), 8.07 (d, J=16.2 Hz 1H); ESI-MS (m/z) 369.26 (M+H)$^+$.

Step 4: 7-{(E)-2-[2-(Cyclopropylmethoxy)-3-methoxyphenyl]vinyl}-6-iodo-3-methyl-5H-[1,3]thiazolo[3,2-a]pyrimidin-5-one: To a solution of Step 3 intermediate (700 mg, 1.810 mmol) in acetonitrile (10 ml) was added N-iodosuccinimide (641 mg, 2.841 mmol) and reacted according to the procedure described in Step 4, Intermediate 2 to afford 600 mg of the desired compound; $^1$H NMR (300 MHz, CDCl$_3$) δ 0.32-0.35 (m, 2H), 0.52-0.58 (m, 2H), 1.18-1.22 (m, 1H), 2.64 (s, 3H), 3.76-3.78 (m, 2H), 7.01-7.14 (m, 3H), 7.25-7.28 (m, 1H), 7.49 (d, J=15.6 Hz, 1H), 8.10-8.16 (d, J=15.9 Hz, 1H); ESI-MS (m/z) 494.99 (M+H)$^+$.

Intermediate 18: 7-{(E)-2-[2-(Cyclopropylmethoxy)-3-methoxyphenyl]vinyl}-6-iodo-2,3-di methyl-5H-[1,3]thiazolo[3,2-a]pyrimidin-5-one Step 1: 7-(Chloromethyl)-2,3-dimethyl-5H-[1,3]thiazolo[3,2-a]pyrimidin-5-one: This compound was synthesized from 2-amino-4,5-dimethylthiazole (5.0 g, 30.365 mmol) and ethyl chloroacetoacetate (6.519 g, 42.511 mmol) in polyphosphoric acid (40.0 g) according to the procedure described in Step 1, Intermediate 2 to afford 10.0 g of the desired compound as a black solid; $^1$H NMR (300 MHz, DMSO-d$_6$) δ 2.28 (s, 3H), 2.60 (s, 3H), 4.52 (s, 1H), 6.25 (s, 1H); ESI-MS (m/z) 229.60 (M+H)$^+$.

Step 2: 2,3-Dimethyl-5-oxo-5H-[1,3]thiazolo[3,2-a]pyrimidin-7-ylmethyl(triphenyl)-phosphonium chloride: Treatment of Step 1 intermediate (2.0 g, 8.746 mmol) with triphenylphosphine (2.520 g, 9.621 mmol) in acetonitrile (50 ml) according to the procedure described in Step 2, Intermediate 2 afforded 4.0 g of the desired compound: $^1$H NMR (300 MHz, DMSO-d6) δ 2.22 (s, 3H), 2.53 (m, 3H), 5.19-5.24 (m, 2H), 6.07-6.08 (m, 1H), 7.68-7.87 (m, 15H); ESI-MS (m/z) 455.35 (M+H)$^+$.

Step 3: 7-{(E)-2-[2-(Cyclopropylmethoxy)-3-methoxyphenyl]vinyl}-2,3-dimethyl-5H-[1,3]thiazolo[3,2-a]pyrimidin-5-one: A stirred suspension of Step 2 intermediate (1.0 g, 2.00 mmol) in dry DMSO (12 ml) was treated with NaH (89 mg, 2.240 mmol) and 2-(cyclopropylmethoxy)-3-methoxybenzaldehyde (462 mg, 2.240 mmol) according to the procedure described in Step 3, Intermediate 2 to yield a crude solid which was purified by column chromatography using 2% ethyl acetate in DCM to afford 600 mg of the desired compound as an off-white solid: $^1$H NMR (300 MHz, DMSO-d6)

δ 0.32-0.35 (m, 2H), 0.54-0.58 (m, 2H), 1.15-1.21 (m, 1H), 2.26 (s, 3H), 2.59 (s, 3H), 3.73-3.75 (m, 2H), 3.79 (s, 3H), 6.13 (s, 1H), 6.99-7.00 (m, 3H), 7.29-7.31 (m, 1H), 8.03 (d, J=16.2 Hz, 1H).

Step 4: 7-{(E)-2-[2-(Cyclopropylmethoxy)-3-methoxyphenyl]vinyl}-6-iodo-2,3-dimethyl-5H-[1,3]thiazolo[3,2-a]pyrimidin-5-one: To a solution of Step 3 intermediate (500 mg, 1.568 mmol) in acetonitrile (10 ml) was added N-iodosuccinimide (494 mg, 2.195 mmol) and reacted according to the procedure described in Step 4, Intermediate 2 to afford 600 mg of the desired compound; $^1$H NMR (300 MHz, CDCl$_3$) δ 0.32-0.34 (m, 2H), 0.54-0.56 (m, 2H), 1.17-1.20 (m, 1H), 2.29 (s, 3H), 2.58 (s, 3H), 3.75-3.77 (m, 2H), 3.80 (s, 3H), 7.04-7.13 (m, 2H), 7.25-7.27 (m, 1H), 7.47 (d, J=15.9 Hz, 1H), 8.12 (d, J=15.6 Hz, 1H); ESI-MS (m/z) 509.01 (M+H)$^+$.

Intermediate 19: 2-Chloro-7-{(E)-2-[2-(2,2-dimethylpropoxy)-3-methoxyphenyl]vinyl}-6-iodo-5H-[1,3]thiazolo[3,2-a]pyrimidin-5-one Step 1: 2-Chloro-7-(chloromethyl)-5H-[1,3]thiazolo[3,2-a]pyrimidin-5-one: Step 1: This compound was prepared according to the procedure outlined in Intermediate 2, Step 1 using 5-chloro-1,3-thiazol-2-amine hydrochloride (3.01 g, 17.482 mmol) polyphosphoric acid (81.0 g) and ethyl chloroacetoacetate (4.03 g, 24.475 mmol) to afford 5.1 g of the desired compound as a brown solid: $^1$H NMR (300 MHz, DMSO-d$_6$) δ 4.55 (s, 2H), 6.45 (s, 1H), 8.31 (s, 1H); ESI-MS (m/z) 235.57 (M+H)$^+$.

Step 2: 2-Chloro-5-oxo-5H-[1,3]thiazolo[3,2-a]pyrimidin-7-ylmethyl(triphenyl)-phosphonium chloride: Step 1 intermediate (3.01 g, 12.761 mmol) was reacted with triphenylphosphine (3.68 g, 14.037 mmol) in acetonitrile (75 ml) according to the procedure outlined in Intermediate 2, Step 2 to afford 3.4 g of the desired compound as an off-white solid: $^1$H NMR (300 MHz, DMSO-d6) δ 5.24 (d, J=16.5 Hz, 2H), 6.23 (s, 1H), 7.43-7.86 (m, 15H), 8.28 (s, 1H); ESI-MS (m/z) 461.42 (M+H)$^+$.

Step 3: 2-Chloro-7-{(E)-2-[2-(2,2-dimethylpropoxy)-3-methoxyphenyl]vinyl}-5H-[1,3]-thiazolo[3,2-a]pyrimidin-5-one: Step 2 intermediate (1.5 g, 3.015 mmol) was reacted with NaH (60% dispersion in mineral oil, 0.079 g, 3.317) and 2-(2,2-dimethylpropoxy)-3-methoxybenzaldehyde (0.736 g, 3.317 mmol) in dry DMSO (20 ml) according to the procedure outlined in Intermediate 2, Step 3 to yield 5.5 g of the desired compound as a white solid; $^1$H NMR (300 MHz, CDCl$_3$) δ 1.12 (s, 9H), 3.61 (s, 2H), 3.84 (s, 3H), 6.21 (s, 1H), 6.87 (d, J=6.9 Hz, 1H), 6.90 (d, J=15.0 Hz, 1H), 7.02 (t, J=7.8 Hz, 1H), 7.19 (d, J=7.8 Hz, 1H), 7.80 (s, 1H), 8.15 (d, J=15.6 Hz, 1H); ESI-MS (m/z) 405.56 (M+H)$^+$.

Step 4: 2-Chloro-7-{(E)-2-[2-(2,2-dimethylpropoxy)-3-methoxyphenyl]vinyl}-6-iodo-5H-[1,3]thiazolo[3,2-a]pyrimidin-5-one:

This compound was prepared using the above Step 3 intermediate (0.501 g, 1.234 mmol) and N-iodosuccinimide (0.416 g, 1.852 mmol) in acetonitrile (10 ml) according to the procedure described in Intermediate 2, Step 4 to afford 0.601 g of the desired compound; $^1$H NMR (300 MHz, CDCl$_3$) δ 1.12 (s, 9H), 3.62 (s, 2H), 3.85 (s, 3H), 6.89 (d, J=8.4 Hz, 1H), 7.06 (t, J=7.8 Hz, 1H), 7.31 (d, J=7.8 Hz, 1H), 7.44 (d, J=15.0 Hz, 1H), 7.79 (s, 1H), 8.35 (d, J=15.0 Hz, 1H); ESI-MS (m/z) 405.56 (M+H)$^+$.

Intermediate 20: 2-Chloro-6-iodo-7-[(E)-2-(2-isobutoxy-3-methoxyphenyl)vinyl]-5H-[1,3]thiazolo[3,2-a]pyrimidin-5-one Step 1: 2-Chloro-7-[(E)-2-(2-isobutoxy-3-methoxyphenyl)vinyl]-5H-[1,3]thiazolo[3,2-a]pyrimidin-5-one: Step 2 intermediate from Intermediate 19 (1.2 g, 2.412 mmol) was reacted with NaH (60% dispersion in mineral oil, 105 mg, 2.610) and 2-isobutoxy-3-methoxybenzaldehyde (546 mg, 2.412 mmol) in dry DMSO (10 ml) according to the procedure outlined in Intermediate 2, Step 3 to yield 5.5 g of the desired compound as a white solid; $^1$H NMR (300 MHz, CDCl$_3$) δ 1.03 (d, J=6.6 Hz, 6H), 1.98-2.06 (m, 1H), 3.68 (d, J=6.6 Hz, 2H), 3.79 (s, 3H), 6.30 (s, 1H), 6.98-7.16 (m, 3H), 7.30-7.33 (m, 1H), 8.05 (d, J=16.2 Hz, 1H), 8.23 (s, 1H).

Step 2: 2-Chloro-6-iodo-7-[(E)-2-(2-isobutoxy-3-methoxyphenyl)vinyl]-5H-[1,3]-thiazolo[3,2-a]pyrimidin-5-one:

This compound was prepared using the above Step 1 intermediate (0.360 g, 0.928 mmol) and N-iodosuccinimide (227 g, 1.012 mmol) in acetonitrile (10 ml) according to the procedure described in Intermediate 2, Step 4 to afford 0.601 g of the desired compound; $^1$H NMR (300 MHz, CDCl$_3$) δ 1.04 (d, J=6.6 Hz, 6H), 2.04-2.11 (m, 1H), 3.72 (d, J=6.3 Hz, 2H), 3.82 (s, 3H), 7.12-7.17 (m, 2H), 7.29-7.31 (m, 1H), 7.50 (d, J=15.6 Hz, 1H), 8.15 (d, J=15.3 Hz, 1H), 8.26 (s, 1H); ESI-MS (m/z) 517.10, 519.29 (M+H)$^+$.

Intermediate 21: 6-Iodo-7-{(E)-2-[3-(methoxy)-2-neopentyloxyphenyl]-1-ethenyl]-3-trifluoro methyl-5H-1,3-thiazolo-[3,2-a]pyrimidin-5-one Step 1: 4-(Trifluoromethyl)-1,3-thiazol-2-amine: A solution of 3-bromo-1,1,1-trifluoroacetone (5.0 g, 26.184 mmol) and thiourea (2.0 g, 26.184 mmol) in ethanol was heated to 50-55° C. for 2.0 h till TLC indicated completion of the reaction. The reaction mixture was concentrated and the residue made basic with 5% NaOH. The mixture was then extracted with ethyl acetate and concentrated to yield a residue which was column purified to afford 3.8 g of the desired compound: $^1$H NMR (300 MHz, DMSO-d$_6$) δ 7.25 (s, 1H), 7.43 (br s, 2H); ESI-MS (m/z) 169.37 (M+H)$^+$.

Step 2: 7-(Chloromethyl)-3-(trifluoromethyl)-5H-[1,3]thiazolo[3,2-a]pyrimidin-5-one:

This compound was synthesized from 2-amino-4-trifluoromethylthiazole, Step 1 intermediate (3.70 g, 22.541 mmol) and ethyl chloroacetoacetate (5.194 g, 31.558 mmol) in polyphosphoric acid (30.0 g) according to the procedure described in Step 1, Intermediate 2 to afford 4.0 g of the desired compound: $^1$H NMR (300 MHz, DMSO-d$_6$) δ 2.28 (s, 3H), 2.60 (s, 3H), 4.52 (s, 1H), 6.25 (s, 1H); ESI-MS (m/z) 269.22 (M+H)$^+$.

Step 3: 5-Oxo-3-trifluoromethyl-5H-[1,3]thiazolo[3,2-a]pyrimidin-7-ylmethyl-(triphenyl) phosphonium chloride: Treatment of Step 2 intermediate (2.0 g, 7.472 mmol) with triphenylphosphine (2.150 g, 8.219 mmol) in acetonitrile (75 ml) according to the procedure described in Step 2, Intermediate 2 afforded 4.0 g of the desired compound as a black solid: $^1$H NMR (300 MHz, DMSO-d6) δ 5.20-5.25 (m, 2H), 6.24 (s, 1H), 7.20 (s, 1H), 7.36 (br s, 3H), 7.74-7.86 (m, 15H); ESI-MS (m/z) 495.15 (M+H)$^+$.

Step 4: 7-{(E)-2-[3-(Methoxy)-2-neopentyloxyphenyl]-1-ethenyl]-3-trifluoromethyl-5H-1,3-thiazolo-[3,2-a]pyrimidin-5-one: A stirred suspension of Step 3 intermediate (1.0 g, 1.886 mmol) in dry DMSO (10 ml) was treated with NaH (83 mg, 2.075 mmol) and 3-methoxy-2,2-dimethylpropoxy-benzaldehyde (460 mg, 2.075 mmol) according to the procedure described in Step 3, Intermediate 2 to yield a crude solid which was purified by column chromatography using 10% ethyl acetate in petroleum ether to afford 300 mg of the desired compound: $^1$H NMR (300 MHz, DMSO-d6) δ 1.08 (s, 9H), 3.56 (s, 2H), 3.79 (s, 3H), 6.13 (s, 1H), 7.02-7.18 (m, 3H), 7.32-7.35 (m, 1H), 8.15 (d, J=15.6 Hz 1H), 8.25 (s, 1H); ESI-MS (m/z) 439.11 (M+H)$^+$.

Step 5: 6-Iodo-7-{(E)-2-[3-(methoxy)-2-neopentyloxyphenyl]-1-ethenyl]-3-trifluoro-methyl-5H-1,3-thiazolo-[3,2-a]pyrimidin-5-one: To a solution of Step 4 intermediate (270 mg, 0.615 mmol) in acetonitrile (10 ml) was added N-iodosuccinimide (193 mg, 0.862 mmol) and reacted according to the procedure described in Step 4, Intermediate 2 to afford 225 mg of the desired compound; $^1$H NMR (300 MHz, CDCl$_3$) δ 1.08 (s, 9H), 3.58 (s, 2H), 3.80 (s, 3H), 7.10-7.12 (m, 2H), 7.31-7.34 (m, 1H), 7.42 (d, J=15.6 Hz, 1H), 8.24-8.29 (m, 2H); ESI-MS (m/z) 565.05 (M+H)$^+$.

Intermediate 22: 4-(2-Methyl-4-oxo-4H-pyrimido[2,1-b][1,3]benzothiazol-3-yl)benzonitrile Step 1: 2-Methtl-4H-pyrimido[2,1-b][1,3]-benzothiazol-4-one: A solution of 1,3-benzothiazol-2-amine (20 g, 0.133 mmol), ethyl acetoacetate (25.96 g, 0.199 mmol) and acetic acid (150 ml) was reacted together according to the procedure described in Intermediate 3, Step 1 to afford 9 g of the desired product as a pale yellow solid; $^1$H NMR (300 MHz, CDCl$_3$) δ 2.38 (s, 3H), 6.15 (s, 1H), 6.95 (d, J=4.8 Hz, 1H), 7.94 (d, J=4.8 Hz, 1H).

Step 2: 3-Iodo-2-methyl-4H-pyrimido[2,1-b][1,3]benzothiazol-4-one: A stirred solution of the Step 1 intermediate (9 g, 41.613 mmol) in acetonitrile (150 ml) was reacted with ceric ammonium nitrate (11 g, 20.803 mmol) followed by iodine (6 g, 24.961 mmol) according to the procedure outlined in Intermediate 1, Step 3 to give 9 g of the product as a pale yellow solid; $^1$H NMR (300 MHz, DMSO-d$_6$) $^1$H NMR (300 MHz, DMSO-d$_6$) δ 3.15 (s, 3H), 7.54-7.60 (m, 2H), 8.00-8.07 (m, 1H), 8.84-8.90 (m, 1H).

Step 3: 4-(2-Methyl-4-oxo-4H-pyrimido[2,1-b][1,3]-benzothiazol-3-yl)benzo-nitrile: This compound was prepared from Step 2 intermediate (800 mg, 2.331 mmol), 4-cyanophenylboronic acid (480 mg, 8.271 mmol), Pd[(C$_6$H$_5$)$_3$P]$_4$ (108 mg, 0.093 mmol) and Na$_2$CO$_3$ (1.48 g, 14.023 mol) in a mixture of toluene, ethanol and water according to the procedure described in Intermediate 3, Step 3 to afford the desired product as a light yellow solid; $^1$H NMR (300 MHz, DMSO-d$_6$) δ 2.49 (s, 3H), 7.53-7.59 (m, 4H), 7.91 (d, J=7.8 Hz, 2H), 8.03-8.10 (m, 1H), 8.80-8.90 (m, 1H); ESI-MS (m/z) 318.30 (M+H)$^+$.

Intermediate 23: 2-Methyl-3-[4-(trifluoromethyl)phenyl]-4H-pyrimido[2,1-b][1,3]benzothiazol-4-one The title compound was prepared by treatment of Step 2 intermediate, Intermediate 22 (2.0 g, 5.845 mmol) with 4-trifluoromethylphenylboronic acid (1.50 g, 8.18 mmol) in the presence of Pd[(C$_6$H$_5$)$_3$P]$_4$ (270 mg, 0.233 mmol) and sodium carbonate (3.71 g, 35.07 mmol) in a mixture of toluene, ethanol and water to afford 2.27 g of the desired product as an off-white solid; $^1$H NMR (300 MHz, DMSO-d$_6$) δ 2.30 (s, 3H), 7.42-7.48 (m, 2H), 7.65-7.67 (m, 2H), 8.00-8.03 (m, 2H), 8.86-8.88 (m, 2H); ESI-MS (m/z) 361.32 (M+H)$^+$.

Intermediate 24: 2-Methyl-3-[4-(trifluoromethoxy)phenyl]-4H-pyrimido[2,1-b][1,3]benzo thiazol-4-one The title compound was prepared by treatment of Step 2 intermediate, Intermediate 22 (2.0 g, 5.845 mmol) with 4-trifluoromethoxyphenylboronic acid (1.684 g, 8.183 mmol) in the presence of Pd[(C$_6$H$_5$)$_3$P]$_4$ (270 mg, 0.233 mmol) and sodium carbonate (3.11 g, 35.07 mmol) in a mixture of toluene, ethanol and water to afford 1.5 g of the desired product as an off-white solid; $^1$H NMR (300 MHz, DMSO-d$_6$) δ 2.02 (s, 3H), 7.41-7.59 (m, 3H), 7.53-7.56 (m, 3H), 8.03-8.07 (m, 1H), 8.84-8.87 (m, 1H); ESI-MS (m/z) 377.17 (M+H)$^+$.

Intermediate 25: 2,10-Dimethyl-3-[4-(trifluoromethoxy)phenyl]pyrimido[1,2-a]benzimidazol-4(10H)-one Step 1: 1-Methyl-1H-benzimidazol-2-amine: To a solution of 2-aminobenzimidazole (3.0 g, 0.0225 mol) in acetone (30 ml) was added KOH (6.32 g, 0.112 mol) followed by methyl iodide (3.51 g, 0.025 mol) and stirred at room temperature for 10 min. The reaction mixture was diluted with ethyl acetate and the organic layer washed with water, brine and dried over anhydrous Na$_2$SO$_4$ to afford crude residue which was column purified to yield the desired product: $^1$H NMR (300 MHz, DMSO-d$_6$) δ 3.47 (s, 3H), 6.34 (br s, 2H), 6.82-6.92 (m, 2H), 7.06-7.09 (m, 2H); ESI-MS (m/z) 148.49 (M+H)$^+$.

Step 2: 2,10-dimethylpyrimido[1,2-a]benzimidazol-4(10H)-one: Step 1 intermediate (1.8 g, 0.0122 mol) was taken in POCl$_3$ (5.0 ml, 0.0488 mol) and treated with polyphosphoric acid (2 g) followed by ethyl acetoacetate and stirred at 130° C. for 3.0 h. The reaction mixture was neutralized with sodium bicarbonate and the precipitated solid was filtered under vacuum followed by column purification to afford the desired compound: $^1$H NMR (300 MHz, DMSO-d$_6$) δ 2.31 (s, 3H), 3.73 (s, 3H), 5.93 (s, 1H), 7.30-7.35 (m, 1H), 7.48-7.53 (m, 1H), 7.63-7.66 (s, 1H), 8.39-8.42 (s, 1H); ESI-MS (m/z) 214.48 (M+H)$^+$.

Step 3: 3-Iodo-2,10-dimethylpyrimido[1,2-a]benzimidazol-4(10H)-one: To a solution of Step 2 intermediate (1.2 g, 5.620 mmol) in acetonitrile (15 ml) was added ceric ammonium nitrate (1.53 g, 2.812 mmol) followed by iodine (0.857 g, 3.325 mmol) and refluxed for 2.0 h. After completion of the reaction, the solvent was evaporated and the residue dissolved in ethyl acetate. Combined organic layer was washed with water, saturated NaHSO$_3$ solution, brine and dried and purified to afford the desired compound: $^1$H NMR (300 MHz, DMSO-d$_6$) δ 2.61 (s, 3H), 3.75 (s, 3H), 7.39-7.42 (s, 1H), 7.52-7.58 (m, 1H), 7.68-7.70 (m, 1H), 8.38-8.41 (s, 1H); ESI-MS (m/z) 340.48 (M+H)$^+$.

Step 4: 2,10-Dimethyl-3-[4-(trifluoromethoxy)phenyl]pyrimido[1,2-a]benzimidazol-4(10H)-one: A solution of Step 3 intermediate (1.2 g, 3.512 mmol), 4-trifluoromethoxyphenyl boronic acid (0.864 g, 4.212 mmol), Pd[(C$_6$H$_5$)$_3$P]$_4$ (0.161 g, 1.420 mmol), Na$_2$CO$_3$ (2.32 g) was reacted together in a mixture of toluene (20 ml), ethanol (5 ml) and water (5 ml) according to the procedure outlined in Step 3, Intermediate 3 to afford the desired product: $^1$H NMR (300 MHz, DMSO-d$_6$) δ 2.24 (s, 3H), 3.78 (s, 3H), 7.33-7.46 (m, 4H), 7.52-7.57 (m, 1H), 7.68-7.71 (m, 1H), 8.40-8.43 (s, 1H); ESI-MS (m/z) 374.62 (M+H)$^+$.

EXAMPLES

Examples 1-9 mentioned in Table 1 below were prepared using appropriate intermediate and appropriate aldehydes according to procedure described in Example 1

TABLE 1

Structural details of Examples 1-9

[Structure: thiazolo[3,2-a]pyrimidin-5-one core with substituents R¹, R², R³ on one phenyl ring via vinyl linker, and a second aryl ring (X = CH or N) with $(R^4)_n$ substituents]

n = 1 or 2

| Example | R¹ | R² | R³ | R⁴ | X | Mol. Formula |
|---|---|---|---|---|---|---|
| Example 1 | H | H | Cl | H | CH | $C_{20}H_{13}ClN_2OS$ |
| Example 2 | cyclopropylmethoxy | OCH₃ | H | H | CH | $C_{25}H_{22}N_2O_3S$ |
| Example 3 | cyclopropylmethoxy | OCH₃ | H | F | N | $C_{24}H_{20}FN_3O_3S$ |
| Example 4 | cyclopropylmethoxy | OCH₃ | H | 4-C(CH₃)₃ | CH | $C_{29}H_{30}N_2O_3S$ |
| Example 5 | cyclopropylmethoxy | OCH₃ | H | 4-COCH₃ | CH | $C_{27}H_{24}N_2O_4S$ |
| Example 6 | cyclopropylmethoxy | OCH₃ | H | 4-N(CH₃)₂ | CH | $C_{27}H_{27}N_3O_3S$ |
| Example 7 | cyclopropylmethoxy | OCH₃ | H | 4-OH | CH | $C_{25}H_{22}N_2O_4S$ |
| Example 8 | cyclopropylmethoxy | OCH₃ | H | 3-F, 5-F | CH | $C_{25}H_{20}F_2N_2O_3S$ |
| Example 9 | OCH₂CH₂CH₂CH₃ | OCH₃ | H | 4-CN | CH | $C_{26}H_{23}N_3O_3S$ |

Example 1

7-[(E)-2-(4-Chlorophenyl)vinyl]-6-phenyl-5H-[1,3]thiazolo[3,2-a]pyrimidin-5-one

To a stirred solution of Intermediate 1 (100 mg, 0.231 mmol) in toluene (20 ml) and ethanol (10 ml) was added phenylboronic acid (33 mg, 0.276 mmol) and Pd[(C₆H₅)₃P]₄ (26 mg, 0.023 mmol) in) followed by sodium carbonate (Na₂CO₃) (48 mg, 0.461 mmol) in water (10 ml). The reaction mixture was heated to reflux for 12 h under nitrogen. The reaction mixture was allowed to cool to room temperature. The residue obtained after evaporation was partitioned between ethyl acetate (500 ml) and water (100 ml). The organic layer was washed with brine (100 ml), dried (Na₂SO₄) and concentrated to afford a crude product which was purified by silica gel column chromatography using 10% ethyl acetate in chloroform to give 5 g of the product as a light yellow solid; ¹H NMR (300 MHz, DMSO-d₆) δ 2.19 (s, 3H), 6.85 (d, J=4.8 Hz, 1H), 7.53 (d, J=7.8 Hz, 3H), 7.77 (m, 4H), 7.88 (d, J=7.8 Hz, 1H), 8.02 (d, J=4.8 Hz, 1H); ESI-MS (m/z) 265.31 (M−H)⁻.

Example 2

7-{(E)-2-[2-(Cyclopropylmethoxy)-3-methoxyphenyl]vinyl}-6-phenyl-5H-[1,3]thiazolo[3,2-a]pyrimidin-5-one The title compound was prepared from Intermediate 2 (100 mg, 0.231 mmol) and phenylboronic acid (33 mg, 0.276 mmol) using Pd[(C₆H₅)₃P]₄ (26 mg, 0.023 mmol) and sodium carbonate (48 mg, 0.461 mmol) in toluene (5 ml) and ethanol (2 ml) and water (2 ml) according to the procedure outlined in Example 1 to yield crude product which was purified by column chromatography to afford 15 mg of the desired product; ¹H NMR (300 MHz, CDCl₃) δ 0.32 (d, J=4.2 Hz, 2H), 0.57 (d, J=7.2 Hz, 2H), 0.99-1.70 (m, 1H), 3.76-3.82 (m, 5H), 6.78-6.82 (m, 3H), 6.91-6.98 (m, 3H), 7.36-7.43 (m, 4H), 7.93 (d, J=6.5 Hz, 1H), 8.27 (d, J=15.6 Hz, 1H); ESI-MS (m/z) 431.33 (M+H)⁺.

Example 3

7-[(E)-2-(2-Cyclopropylmethoxy)-3-methoxyphenyl)-1-ethenyl]-6-(6-fluoro-3-pyridyl)-5H-[1,3]thiazolo[3,2-a]pyrimidin-5-one The title compound was prepared from Intermediate 2 (100 mg, 0.200 mmol) and 2-fluoro-5-pyridylboronic acid (35 mg, 0.24 mmol) using Pd[(C₆H₅)₃P]₄ (9 mg, 0.008 mmol) and sodium carbonate (133 mg, 1.2 mmol) in toluene (5 ml) and ethanol (2 ml) and water (2 ml) according to the procedure outlined in Example 1 to yield crude product which was purified by column chromatography to afford 76 mg of the desired product; ¹H NMR (300 MHz, DMSO-d₆) δ 0.28 (br s, 2H), 0.52-0.54 (m, 2H), 1.04-1.07 (m, 1H), 3.69-3.71 (m, 2H), 3.77 (s, 3H), 6.88 (d, J=15.6 Hz, 1H), 7.00 (br s, 3H), 7.29-7.31 (m, 1H), 7.54 (br s, 1H), 7.97-8.00 (m, 2H), 8.18-8.21 (m, 2H); ESI-MS (m/z) 450.28 (M+H)⁺.

Example 4

6-[4-(tert-Butylphenyl)]-7-[(E)-2-(2-cyclopropylmethoxy)-3-methoxyphenyl)-1-ethenyl]-5H-[1,3]thiazolo[3,2-a]pyrimidin-5-one The title compound was prepared from Intermediate 2 (200 mg, 0.41 mmol) and 4-tert-butylphenylboronic acid (104 mg, 0.580 mmol) using Pd[(C₆H₅)₃P]₄ (20 mg, 0.010 mmol) and sodium carbonate (265 mg, 2.49 mmol) in toluene (10 ml) and ethanol (5 ml) and water (4 ml) according to the procedure outlined in Example 1 to afford crude residue which was purified by column chromatography to afford 198 mg of the desired product as an off-white solid; ¹H NMR (300 MHz, DMSO-$d_6$) δ 0.23-0.25 (m, 2H), 0.46-0.48 (m, 2H), 0.90-1.10 (m, 1H), 1.33 (s, 9H), 3.67 (d, J=7.2 Hz, 2H), 3.76 (s, 3H), 6.87-6.89 (m, 1H), 6.96-7.01 (m, 3H), 7.25-7.28 (m, 2H), 7.46-7.49 (m, 2H), 7.96-7.98 (m, 2H), 8.09 (d, J=16.2 Hz, 1H); ESI-MS (m/z) 487.51 (M+H)$^+$.

Example 5

1-{4-{7-[(E)-2-(2-Cyclopropylmethoxy)-3-methoxyphenyl)-1-ethenyl]-5-oxo-5H-[1,3]thiazolo[3,2-a]pyrimidin-6-yl}phenyl}-1-ethanone The title compound was prepared from Intermediate 2 (250 mg, 0.520 mmol) and 4-acetylphenylboronic acid (120 mg, 0.728 mmol) using Pd[($C_6H_5$)$_3$P]$_4$ (24 mg, 0.020 mmol) and sodium carbonate (331 mg, 3.122 mmol) in toluene (10 ml) and ethanol (5 ml) and water (4 ml) according to the procedure outlined in Example 1 to afford crude residue which was purified by column chromatography to afford 181 mg of the desired product as an off-white solid; $^1$H NMR (300 MHz, DMSO-$d_6$) δ 0.24-0.26 (m, 2H), 0.47-0.49 (m, 2H), 0.9-1.10 (m, 1H), 2.63 (s, 3H), 3.68 (d, J=7.5 Hz, 2H), 3.76 (s, 3H), 6.86-6.90 (m, 1H), 6.91-6.93 (m, 1H), 7.48-7.51 (m, 4H), 7.99-8.04 (m, 4H), 8.17 (d, J=15.6 Hz, 1H); ESI-MS (m/z) 473.13 (M+H)$^+$.

Example 6

6-(4-Dimethylaminophenyl)-7-[(E)-2-(2-cyclopropylmethoxy-3-methoxy phenyl]-1-ethenyl]-5H-[1,3]thiazolo[3,2-a]pyrimidin-5-one The title compound was prepared from Intermediate 2 (150 mg, 31 mmol), 4-N,N-dimethylaminophenylboronic acid (61 mg, 37 mmol), Pd[($C_6H_5$)$_3$P]$_4$ (61 mg, 37 mmol) and sodium carbonate (206 mg, 1.91 mmol) in a mixture of toluene, ethanol and water according to the procedure outlined in Example 1 to afford a crude product which was purified by silica gel column chromatography using 10% ethyl acetate in chloroform to give 110 mg of the product; $^1$H NMR (300 MHz, DMSO-$d_6$) δ 0.26-0.28 (m, 1H), 0.50 (d, J=7.8 Hz, 2H), 1.06-1.08 (m, 1H), 6.77 (d, J=8.4 Hz, 2H), 6.88-6.90 (m, 1H), 6.97-7.04 (m, 3H), 7.14 (d, J=5.1 Hz, 2H), 7.95 (d, J=5.1 Hz, 1H), 8.10 (d, J=15.6 Hz, 1H); ESI-MS (m/z) 474.19 (M+H)$^+$.

Example 7

7-[(E)-2-(2-Cyclopropylmethoxy-3-methoxyphenyl)-1-ethenyl]-6-(4-hydroxyphenyl)-5H-[1,3]thiazolo[3,2-a]pyrimidin-5-one A solution of Intermediate 2 (500 mg, 1.040 mmol), 4-hydroxyphenylboronic acid (172 mg, 1.249 mmol), Pd[($C_6H_5$)$_3$P]$_4$ (120 mg, 0.104 mmol) and cesium fluoride (506 mg, 3.331 mmol) in dry THF was heated to reflux for 4.0 h. After completion of reaction, the mixture was concentrated in vacuo. The residue was dissolved in ethyl acetate, washed with water, brine and dried over anhydrous $Na_2SO_4$ to afford a crude residue which was purified using 1% $CH_3OH$ in $CHCl_3$ to afford 271 mg of the desired compound as a yellow solid; $^1$H NMR (300 MHz, DMSO-$d_6$) δ 0.26-0.28 (m, 2H), 0.48-0.54 (m, 2H), 1.03-1.07 (m, 1H), 3.67-3.70 (m, 2H), 3.76 (s, 3H), 6.81-6.92 (m, 3H), 6.97-7.03 (m, 3H), 7.10-7.13 (m, 2H), 7.47 (d, J=4.5 Hz, 1H), 7.95 (d, J=5.1 Hz, 1H), 8.10 (d, J=15.6 Hz, 1H), 9.57 (s, 1H); ESI-MS (m/z) 447.20 (M+H)$^+$.

Example 8

7-[(E)-2-(2-Cyclopropylmethoxy)-3-methoxyphenyl)-1-ethenyl]-6-(3,5-difluoro phenyl)-5H-[1,3]thiazolo[3,2-a]pyrimidin-5-one A solution of Intermediate 3 (200 mg, 0.719 mmol), 2-(cyclopropylmethoxy)-3-methoxybenzaldehyde (205 mg, 1.078 mmol) and sodium ethoxide (98 mg, 1.438 mmol) in ethanol (20 ml) was refluxed for 15 h. The reaction mixture was concentrated, the residue extracted with ethyl acetate, washed with water and brine to afford crude solid which was purified by column chromatography using 10% ethyl acetate in chloroform to afford 145 mg of the desired compound as a yellow solid; $^1$H NMR (300 MHz, $CDCl_3$) δ 0.29-0.33 (m, 2H), 0.57-0.59 (m, 2H), 1.20-1.30 (m, 1H), 3.79 (d, J=7.2 Hz, 1H), 3.83 (s, 3H), 6.80-6.86 (m, 2H), 6.90-7.23 (m, 6H), 7.93 (d, J=4.8 Hz, 1H), 8.32 (d, J=15.3 Hz, 1H); ESI-MS (m/z) 467.31 (M+H)$^+$.

Example 9

4-{7-[(E)-2-(2-Butoxy-3-methoxyphenyl)-1-ethenyl]-5-oxo-5H-[1,3]thiazolo[3,2-a]pyrimidin-6-yl}benzonitrile The title compound was prepared using Intermediate 4 (350 mg, 1.304 mmol, (2-butoxy-3-methoxy)benzaldehyde (354 mg, 1.601 mmol) and sodium ethoxide (176 mg, 2.301 mmol) in ethanol (25 ml) according to the procedure described in Example 8 to afford a crude product which was purified by silica gel column chromatography using 1% acetone in chloroform to give 260 mg of the product as a light yellow solid; $^1$H NMR (300 MHz, DMSO-$d_6$) δ 0.92-0.99 (m, 3H), 1.45-1.52 (m, 4H), 3.77 (s, 3H), 3.80-3.85 (m, 2H), 6.88 (d, J=15.6 Hz, 1H), 6.95-7.01 (m, 3H), 7.52-7.57 (m, 3H), 7.92 (d, J=8.4 Hz, 1H), 8.01 (d, J=4.8 Hz, 1H), 8.10 (d, J=15.6 Hz, 1H); ESI-MS (m/z) 458.12 (M+H)$^+$.

Examples 10-22 mentioned in Table 2 below were prepared using Intermediate 4 and the appropriate aldehydes according to the procedure described in Example 9

TABLE 2

Structural details of Examples 10-22

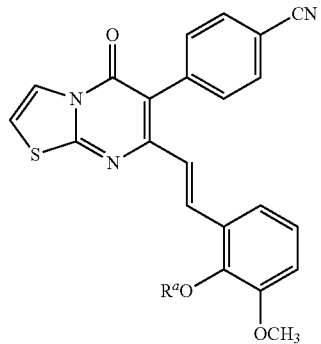

| Example | $R^a$ | Mol. Formula |
|---|---|---|
| Example 10 | n-pentyl | $C_{27}H_{25}N_3O_3S$ |
| Example 11 | $CH_2CH_2CH(CH_3)_2$ | $C_{27}H_{25}N_3O_3S$ |
| Example 12 | $CH_2CH(CH_3)_2$ | $C_{26}H_{23}N_3O_3S$ |
| Example 13 | $CH_2C(CH_3)_3$ | $C_{27}H_{25}N_3O_3S$ |
| Example 14 | $CH_2CH_2OCH_3$ | $C_{25}H_{21}N_3O_4S$ |
| Example 15 | $CH_2CH_2OC_2H_5$ | $C_{26}H_{23}N_3O_4S$ |

TABLE 2-continued

Structural details of Examples 10-22

| Example | $R^a$ | Mol. Formula |
|---|---|---|
| Example 16 | cyclopropylmethyl | $C_{26}H_{21}N_3O_3S$ |
| Example 17 | cyclobutylmethyl | $C_{27}H_{23}N_3O_3S$ |
| Example 18 | cyclopentyl | $C_{27}H_{23}N_3O_3S$ |
| Example 19 | cyclohexylmethyl | $C_{29}H_{27}N_3O_3S$ |
| Example 20 | 3-fluorobenzyl | $C_{29}H_{20}FN_3O_3S$ |
| Example 21 | (pyridin-2-yl)methyl | $C_{28}H_{20}N_4O_3S$ |
| Example 22 | $CH_2(CH_2)_2CN$ | $C_{26}H_{20}N_4O_3S$ |

Example 10

4-{7-[(E)-2-(3-Methoxy-2-pentyloxyphenyl)-1-ethenyl]-5-oxo-5H-[1,3]-thiazolo[3,2-a]pyrimidin-6-yl}benzonitrile The title compound was prepared from Intermediate 4 (400 mg, 1.4 mmol), (3-methoxy-2-pentyloxy)benzaldehyde (498 mg, 2.22 mmol) and sodium ethoxide (190 mg, 2.8 mmol) in ethanol (25 ml) according to procedure described in Example 9 to give 300 mg of the product as a light yellow solid; $^1$H NMR (300 MHz, DMSO-$d_6$) δ 0.90-1.00 (m, 3H), 1.25-1.45 (m, 4H), 1.46-1.60 (m, 2H), 3.77 (s, 3H), 3.65-3.85 (m, 2H), 6.87 (d, J=16.2 Hz, 1H), 6.96-7.00 (m, 3H), 7.54-7.57 (m, 3H), 7.93 (d, J=7.5 Hz, 1H), 8.00-8.01 (m, 2H), 8.09 (d, J=14.7 Hz, 1H); ESI-MS (m/z) 472.27 (M+H)$^+$.

Example 11

4-{7-[(E)-2-(2-Isopentyloxy-3-methoxyphenyl)-1-ethenyl]-5-oxo-5H-[1,3]thiazolo[3,2-a]pyrimidin-6-yl}benzonitrile The title compound was prepared by condensation of Intermediate 4 (350 mg, 1.305 mmol) with (2-isopentyloxy-3-methoxy)benzaldehyde (436 mg, 1.961 mmol) in presence of sodium ethoxide (178 mg, 2.604 mmol) according to the procedure described in Example 9 to give 256 mg of the desired product as a light yellow solid; $^1$H NMR (300 MHz, DMSO-$d_6$) δ 0.94 (d, J=6.3 Hz, 6H), 1.43 (d, J=5.7 Hz, 2H), 1.88 (br s, 1H), 3.77 (s, 3H), 3.85 (br s, 2H), 6.88 (d, J=16.2 Hz, 1H), 6.91-7.00 (m, 3H), 7.53-7.58 (m, 3H), 7.92-8.04 (m, 3H), 8.09 (d, J=15.0 Hz, 1H); ESI-MS (m/z) 472.30 (M+H)$^+$.

Example 12

4-{7-[(E)-2-(2-Isobutoxy-3-methoxyphenyl)-1-ethenyl]-5-oxo-5H-[1,3]thiazolo[3,2-a]-pyrimidin-6-yl}benzonitrile The title compound was prepared by the reaction of Intermediate 4 (350 mg, 1.325 mmol) with 2-isobutoxy-3-methoxybenzaldehyde (409 mg, 1.961 mmol) in presence of sodium ethoxide (178 mg, 2.264 mmol) according to the procedure described in Example 9 to give 270 mg of the desired product as a light yellow solid; $^1$H NMR (300 MHz, DMSO-$d_6$) δ 1.85 (d, J=3.9 Hz, 4H), 2.03 (d, J=7.8 Hz, 3H), 3.77 (s, 3H), 3.83 (d, J=6.3 Hz, 2H), 6.84 (d, J=15.6 Hz, 1H), 6.95-7.00 (m, 3H), 7.50-7.58 (m, 3H), 7.92-8.04 (m, 3H), 8.14 (d, J=15.3 Hz, 1H); ESI-MS (m/z) 470.45 (M+H)$^+$.

Example 13

4-{7-[(E)-2-(3-Methoxy-2-neopentyloxyphenyl)-1-ethenyl]-5-oxo-5H-[1,3]thiazolo[3,2-a]pyrimidin-6-yl}benzonitrile The title compound was prepared from Intermediate 4 (400 mg, 1.496 mmol), 3-methoxy-2-neopentyloxybenzaldehyde (465 mg, 2.094 mmol) and sodium ethoxide (203 mg, 2.992 mmol) in ethanol (25 ml) according to the procedure described in Example 9 to give 290 mg of the product as a light yellow solid; $^1$H NMR (300 MHz, DMSO-$d_6$) δ 1.03 (s, 9H), 3.53 (s, 2H), 3.77 (s, 3H), 6.77 (d, J=15.6 Hz, 1H), 6.99 (br s, 3H), 7.51-7.57 (m, 3H), 7.91-7.99 (m, 3H), 8.26 (d, J=15.0 Hz, 1H); ESI-MS (m/z) 472.26 (M+H)$^+$.

Example 14

4-{7-[(E)-2-(3-Methoxy-2-(2-methoxyethoxy)phenyl]-1-ethenyl}-5-oxo-5H-[1,3]-thiazolo[3,2-a]pyrimidin-6-yl}benzonitrile The title compound was prepared by condensation of Intermediate 4 (350 mg, 1.312 mmol) with 3-methoxy-2-(2-methoxyethoxy)benzaldehyde (385 mg, 1.833 mmol) in presence of sodium ethoxide (178 mg, 2.624 mmol) according to the procedure outlined in Example 9 to afford 243 mg of the desired product as an off-white solid; $^1$H NMR (300 MHz, DMSO-$d_6$) δ 3.47-3.53 (m, 2H), 3.70 (s, 3H), 3.78 (s, 3H), 3.99-4.05 (m, 2H), 6.79 (d, J=15.6 Hz, 1H), 6.93-7.01 (m, 3H), 7.50-7.58 (m, 3H), 7.92 (d, J=8.1 Hz, 2H), 8.01 (d, J=4.8 Hz, 1H), 8.22 (d, J=15.9 Hz, 1H); ESI-MS (m/z) 460.50 (M+H)$^+$.

Example 15

4-{7-[(E)-2-(2-Ethoxyethoxy-3-methoxyphenyl]-1-ethenyl}-5-oxo-5H-[1,3]thiazolo[3,2-a]pyrimidin-6-yl}benzonitrile The title compound was prepared by condensation of Intermediate 4 (335 mg, 1.252 mmol) with 2-(2-ethoxyethoxy)-3-methoxy-benzaldehyde (339 mg, 1.753 mmol) in presence of sodium ethoxide (170 mg, 2.506 mmol) according to the procedure described in Example 9 to yield 231 mg of the desired product as a light yellow solid; $^1$H NMR (300 MHz, DMSO-$d_6$) δ 1.16 (t, J=6.6 Hz, 3H), 3.45-3.52 (m, 4H), 3.78 (s, 3H), 4.00-4.08 (m, 2H), 6.78 (d, J=15.6 Hz, 1H), 6.94-7.01 (m, 3H), 7.50-7.58 (m, 3H), 7.92 (d, J=7.8 Hz, 2H), 8.02 (d, J=4.8 Hz, 1H), 8.20 (d, J=15.6 Hz, 1H); ESI-MS (m/z) 474.45 (M+H)$^+$.

Example 16

4-{7-[(E)-2-[2-(Cyclopropylmethoxy)-3-methoxyphenyl]-1-ethenyl}-5-oxo-5H-[1,3]thiazolo[3,2-a]pyrimidin-6-yl}benzonitrile The title compound was prepared from Intermediate 4 (180 mg, 0.673 mmol), 2-(cyclopropylmethoxy)-3-methoxybenzaldehyde (192 mg, 1.010 mmol) and sodium ethoxide (92 mg, 1.346 mmol) in ethanol (15 ml) according to the procedure described in Example 9 to give 135 mg of the product as a light yellow solid; $^1$H NMR (300 MHz, DMSO-$d_6$) δ 0.25-0.27 (m, 2H), 0.49-0.51 (m, 2H), 0.90-1.10 (m, 1H), 3.68 (d, J=7.8 Hz, 2H), 3.77 (s, 3H), 6.85 (d, J=15.6 Hz, 1H), 6.96-7.00 (m, 3H), 7.51-7.57 (m, 3H), 7.92 (d, J=7.8 Hz, 2H), 8.01 (d, J=5.1 Hz, 2H), 8.17 (d, J=15.6 Hz, 1H); ESI-MS (m/z) 456.23 (M+H)$^+$.

Example 17

4-{7-[(E)-2-(2-Cyclobutylmethoxy-3-methoxy)phenyl-1-ethenyl]-5-oxo-5H-[1,3]-thiazolo[3,2-a]pyrimidin-6-yl}benzonitrile The title compound was prepared by the reaction of Intermediate 4 (350 mg, 1.304 mmol), 2-cyclobutylmethoxy-3-methoxybenzaldehyde (374 mg, 1.713 mmol) and sodium ethoxide (176 mg, 2.604 mmol) in ethanol (15 ml) according to the procedure described in Example 9 to give 240 mg of the desired product as a light yellow solid; $^1$H NMR (300 MHz, DMSO-$d_6$) δ 1.84 (d, J=3.9 Hz, 4H), 2.03 (d, J=7.8 Hz, 3H), 7.50-7.58 (m, 3H), 7.92-8.04 (m, 3H), 8.14 (d, J=15.3 Hz, 1H); ESI-MS (m/z) 470.45 (M+H)$^+$.

Example 18

4-{7-[(E)-2-(2-Cyclopentyloxy-3-methoxy)phenyl-1-ethenyl]-5-oxo-5H-[1,3]thiazolo-[3,2-a]pyrimidin-6-yl}benzonitrile The title compound was prepared by condensation of Intermediate 4 (300 mg, 1.122 mmol) with 2-(cyclopentyloxy)-3-methoxybenzaldehyde (310 mg, 1.683 mmol) in presence of sodium ethoxide (152 mg, 2.242 mmol) in ethanol (15 ml) according to the procedure outlined in Example 9 to give 181 mg of the desired product as a light yellow solid; $^1$H NMR (300 MHz, DMSO-$d_6$) δ 1.50-1.60 (m, 6H), 1.78-1.85 (m, 2H), 3.78 (s, 3H), 4.83-4.89 (m, 1H), 6.80 (d, J=15.0 Hz, 1H), 6.89-6.99 (m, 3H), 7.51-7.57 (m, 3H), 7.93 (d, J=8.4 Hz, 2H), 8.00 (d, J=4.8 Hz, 1H), 8.14 (d, J=15.6 Hz, 1H); ESI-MS (m/z) 485.18 (M+H)$^+$.

Example 19

4-{7-[(E)-2-(2-Cyclohexylmethoxy-3-methoxy)phenyl-1-ethenyl]-5-oxo-5H-[1,3]-thiazolo[3,2-a]pyrimidin-6-yl}benzonitrile The title compound was prepared by the reaction of Intermediate 4 (325 mg, 1.212 mmol) with 2-(cyclohexylmethoxy)-3-methoxybenzaldehyde (422 mg, 1.103 mmol) in presence of sodium ethoxide (165 mg, 2.484 mmol) according to the procedure described in Example 9 to give 256 mg of the desired product as a light yellow solid; $^1$H NMR (300 MHz, DMSO-$d_6$) δ 1.08 (t, J=7.2 Hz, 3H), 1.22-1.30 (m, 3H), 1.65-1.85 (m, 5H), 3.32-3.40 (m, 1H), 3.65 (d, J=6.6 Hz, 1H), 3.76 (s, 3H), 6.81 (d, J=15.6 Hz, 1H), 6.94-7.00 (m, 3H), 7.50-7.58 (m, 3H), 7.92 (d, J=8.4 Hz, 2H), 8.00 (d, J=4.8 Hz, 1H), 8.19 (d, J=15.6 Hz, 1H); ESI-MS (m/z) 498.37 (M+H)$^+$.

Example 20

4-{7-[(E)-2-[2-(3-Fluorobenzyloxy)-3-methoxyphenyl-1-ethenyl]-5-oxo-5H-[1,3]-thiazolo[3,2-a]pyrimidin-6-yl}benzonitrile The title compound was prepared by condensation of Intermediate 4 (350 mg, 1.009 mmol) with 2-(3-fluorobenzyloxy-3-methoxy)benzaldehyde (477 mg, 1.833 mmol) in presence of sodium ethoxide (178 mg, 2.618 mmol) in ethanol (15 ml) according to the procedure described in Example 9 to give 241 mg of the desired product as a light yellow solid; $^1$H NMR (300 MHz, DMSO-$d_6$) δ 3.83 (s, 3H), 4.94 (s, 2H), 6.76 (d, J=16.2 Hz, 1H), 6.90-6.98 (m, 1H), 7.02-7.09 (m, 2H), 7.17-7.26 (m, 3H), 7.38-7.44 (m, 1H), 7.50-7.55 (m, 3H), 7.86 (d, J=7.8 Hz, 2H), 8.00 (d, J=5.1 Hz, 1H), 8.09 (d, J=15.6 Hz, 1H); ESI-MS (m/z) 526.15 (M+H)$^+$.

Example 21

4-{7-[(E)-2-{3-Methoxy-2-(2-pyridinylmethoxy)phenyl]-1-ethenyl}-5-oxo-5H-[1,3]-thiazolo[3,2-a]pyrimidin-6-yl}benzonitrile The title compound was prepared by condensation of Intermediate 4 (400 mg, 1.496 mmol) with 3-methoxy-2-(pyridinylmethoxy)benzaldehyde (546 mg, 2.244 mmol) in presence of sodium ethoxide (200 mg, 2.939 mmol) in ethanol (15 ml) according to the procedure described in Example 9 to give 275 mg of the desired product as a light yellow solid; IR (KBr) 2837, 2226, 1652, 1478, 1270 cm$^{-1}$; $^1$H NMR (300 MHz, DMSO-$d_6$) δ 3.81 (s, 3H), 4.99 (s, 2H), 6.78 (d, J=15.6 Hz, 1H), 6.97-7.06 (m, 3H), 7.30-7.36 (m, 1H), 7.45-7.59 (m, 4H), 7.80-7.88 (m, 3H), 8.00 (d, J=5.9 Hz, 1H), 8.08 (d, J=15.0 Hz, 1H) 8.49-8.55 (m, 1H); ESI-MS (m/z) 493.56 (M+H)$^+$.

Example 22

4-{7-[(E)-2-{2-(3-Cyanopropoxy)-3-(methoxyphenyl)-1-ethenyl]}-5-oxo-5H-[1,3]thiazolo[3,2-a]pyrimidin-6-yl}benzonitrile The title compound was prepared by condensation of Intermediate 4 (400 mg, 1.496 mmol) with 2-(3-cyanopropoxy)-

3-methoxybenzaldehyde (492 mg, 2.244 mmol) in presence of sodium ethoxide (203 mg, 2.990 mmol) in ethanol (15 ml) according to the procedure outlined in Example 9 to give 270 mg of the desired product as a light yellow solid; $^1$H NMR (300 MHz, DMSO-$d_6$) δ 1.84-1.90 (m, 2H), 2.68-2.78 (m, 2H), 3.79 (s, 3H), 3.89-3.95 (m, 2H), 6.84 (d, J=15.6 Hz, 1H), 6.98-7.05 (m, 3H), 7.52-7.60 (m, 3H), 7.93 (d, J=6.9 Hz, 2H), 8.00-8.08 (m, 2H); ESI-MS (m/z) 469.12 (M+H)$^+$.

Example 23

4-{5-Oxo-7-[(E)-2-(3-pyridyl)-1-ethenyl]-5H-[1,3] thiazolo[3,2-a]pyrimidin-6-yl}-benzonitrile

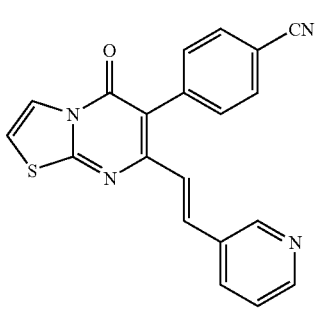

The title compound was prepared by condensation of Intermediate 4 (350 mg, 1.309 mmol) with nicotinaldehyde (196 mg, 1.833 mmol) in presence of sodium ethoxide (178 mg, 2.618 mmol) in ethanol (15 ml) according to the procedure outlined in Example 9 to give 266 mg of the desired product as a light yellow solid; $^1$H NMR (300 MHz, DMSO-$d_6$) δ 6.88 (d, J=15.6 Hz, 1H), 7.30-7.38 (m, 1H), 7.50-7.58 (m, 3H), 7.84-7.93 (m, 4H), 8.02 (d, J=4.8 Hz, 1H), 8.47 (d, J=3.9 Hz, 1H), 8.70 (s, 1H); ESI-MS (m/z) 357.32 (M+H)$^+$.

Example 24

7-[(E)-2-(2-Cyclopropylmethoxy)-1-ethenyl]-6-[4-(trifluoromethyl)phenyl]-5H-[1,3]-thiazolo[3,2-a]pyrimidin-5-one

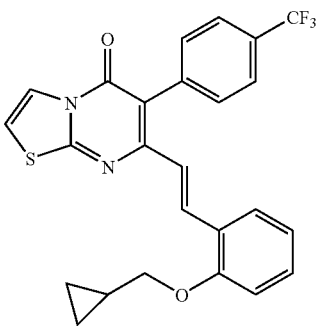

A solution of Intermediate 5 (400 mg, 1.289 mmol), (2-cyclopropylmethoxy)benzaldehyde (356 mg, 2.025 mmol) and sodium ethoxide (183 mg, 2.108 mmol) in ethanol (20 ml) was refluxed for 15 h. The reaction mixture was concentrated, the residue extracted with ethyl acetate, washed with water and brine to afford crude solid which was purified by column chromatography to afford 241 mg of the desired compound as an off-white solid; $^1$H NMR (300 MHz, DMSO-$d_6$) δ 0.12-0.20 (m, 2H), 0.27-0.32 (m, 2H), 0.78-0.83 (m, 1H), 3.74 (d, J=6.9 Hz, 2H), 6.90-6.97 (m, 2H), 7.18-7.26 (m, 2H), 7.39 (d, J=6.9 Hz, 1H), 7.52 (d, J=4.8 Hz, 1H), 7.58 (d, J=7.8 Hz, 2H), 7.80 (d, J=7.5 Hz, 2H), 7.91-7.97 (m, 1H), 8.00 (d, J=4.5 Hz, 1H); ESI-MS (m/z) 469.22 (M+H)$^+$.

Examples 25-36, outlined in Table 3, were prepared in a single step from Intermediate 5 and the appropriate aldehydes using procedures described herein

TABLE 3

Structural details of Examples 25-36

| Example | R$^3$ | Mol formula |
|---|---|---|
| Example 25 | $CH_2CH_2CH_3$ | $C_{25}H_{21}F_3N_2O_3S$ |
| Example 26 | $CH_2(CH_2)_2CH_3$ | $C_{26}H_{23}F_3N_2O_3S$ |
| Example 27 | $CH_2CH(CH_3)_2$ | $C_{26}H_{23}F_3N_2O_3S$ |
| Example 28 | $CH_2CH_2CH(CH_3)_2$ | $C_{27}H_{25}F_3N_2O_3S$ |
| Example 29 | $CH_2C(CH_3)_3$ | $C_{27}H_{25}F_3N_2O_3S$ |
| Example 30 | $CH_2(CH_2)_2CN$ | $C_{26}H_{20}F_3N_3O_3S$ |
| Example 31 | $CH_2CH_2OCH_3$ | $C_{25}H_{21}F_3N_2O_4S$ |
| Example 32 | $CH_2CH_2OC_2H_5$ | $C_{26}H_{23}F_2N_2O_4S$ |
| Example 33 | (cyclopropylmethyl) | $C_{26}H_{21}F_3N_2O_3S$ |
| Example 34 | (cyclobutylmethyl) | $C_{27}H_{23}F_3N_2O_3S$ |
| Example 35 | (cyclopentylmethyl) | $C_{27}H_{23}F_3N_2O_3S$ |
| Example 36 | (2-pyridylmethyl) | $C_{28}H_{20}F_3N_3O_3S$ |

Example 25

7-[(E)-2-(3-Methoxy-2-propoxyphenyl)-1-ethenyl]-6-[4-(trifluoromethyl)phenyl]-5H-[1,3]thiazolo[3,2-a]pyrimidin-5-one The title compound was prepared by condensation of Intermediate 5 (400 mg, 1.289 mmol) with 3-methoxy-2-propoxy-benzaldehyde (375 mg, 1.933 mmol) in presence of sodium ethoxide (175 mg, 2.578 mmol) in ethanol (15 ml) according to the procedure described in Example 24 to give 310 mg of the desired product as an off-white solid; $^1$H NMR (300 MHz, DMSO-d$_6$) δ 0.93 (t, J=6.6 Hz, 3H), 1.48 (q, J=6.9 Hz, 2H), 3.77 (s, 5H), 6.93-7.00 (m, 4H), 7.52-7.59 (m, 3H), 7.82 (d, J=7.8 Hz, 2H), 7.98-8.02 (m, 2H); ESI-MS (m/z) 487.35 (M+H)$^+$.

Example 26

7-[(E)-2-(2-Butoxy-3-methoxyphenyl)-1-ethenyl]-6-[4-(trifluoromethyl)phenyl]-5H-[1,3]thiazolo[3,2-a]pyrimidin-5-one The title compound was prepared by condensation of Intermediate 5 (400 mg, 1.289 mmol) with 2-butoxy-3-methoxybenzaldehyde (400 mg, 1.922 mmol) in presence of sodium ethoxide (175 mg, 2.578 mmol) in ethanol (15 ml) according to the procedure described in Example 24 to afford 271 mg of the desired product as an off-white solid; $^1$H NMR (300 MHz, DMSO-d$_6$) δ 0.95 (t, J=6.3 Hz, 3H), 1.42-1.48 (m, 4H), 3.77 (s, 3H), 3.79-3.85 (m, 2H), 6.91-7.01 (m, 4H), 7.52 (d, J=4.8 Hz, 1H), 7.58 (d, J=7.8 Hz, 2H), 7.82 (d, J=8.4 Hz, 2H), 8.01 (d, J=4.8 Hz, 1H), 8.08 (d, J=15.6 Hz, 1H); ESI-MS (m/z) 501.18 (M+H)$^+$.

Example 27

7-[(E)-2-(2-Isobutoxy-3-methoxyphenyl)-1-ethenyl]-6-[4-(trifluoromethyl)phenyl]-5H-[1,3]thiazolo[3,2-a]pyrimidin-5-one The title compound was prepared by condensation of Intermediate 5 (400 mg, 1.289 mmol) with 2-isobutoxy-3-methoxybenzaldehyde (400 mg, 1.922 mmol) in presence of sodium ethoxide (175 mg, 2.578 mmol) in ethanol (15 ml) according to the procedure described in Example 24 to give 285 mg of the desired product as a light yellow solid; $^1$H NMR (300 MHz, DMSO-d$_6$) δ 0.93 (d, J=3.6 Hz, 6H), 1.72 (br s, 1H), 3.58 (br s, 2H), 3.77 (s, 3H), 6.91-7.00 (m, 4H), 7.53-7.58 (m, 3H), 7.78-7.84 (m, 2H), 8.00 (br s, 1H), 8.12 (d, J=15.3 Hz, 1H); ESI-MS (m/z) 501.24 (M+H)$^+$.

Example 28

7-[(E)-2-(2-Isopentyloxy-3-methoxyphenyl)-1-ethenyl]-6-[4-(trifluoromethyl)phenyl]-5H-[1,3]thiazolo[3,2-a]pyrimidin-5-one The title compound was synthesized by condensation of Intermediate 5 (400 mg, 1.289 mmol) with 2-isopentyloxy-3-methoxybenzaldehyde (400 mg, 1.812 mmol) in presence of sodium ethoxide (163 mg, 2.418 mmol) in ethanol (15 ml) according to the procedure described in Example 24 to give 308 mg of the desired product as an off-white solid; $^1$H NMR (300 MHz, DMSO-d$_6$) δ 0.92 (d, J=6.3 Hz, 6H), 1.42 (q, J=6.3 Hz, 2H), 1.80-1.90 (m, 1H), 3.77 (s, 3H), 3.84 (t, J=6.3 Hz, 2H), 6.90-7.00 (m, 4H), 7.51 (d, J=4.8 Hz, 1H), 7.58 (d, J=7.8 Hz, 2H), 7.83 (d, J=7.8 Hz, 2H), 8.01 (d, J=4.8 Hz, 1H), 8.09 (d, J=15.6 Hz, 1H); ESI-MS (m/z) 515.52 (M+H)$^+$.

Example 29

7-[(E)-2-(3-Methoxy-2-neopentyloxy)phenyl-1-ethenyl]-6-(4-(trifluoromethyl)phenyl]-5H-[1,3]thiazolo[3,2-a]pyrimidin-5-one The title compound was synthesized by condensation of Intermediate 5 (400 mg, 1.350 mmol) with 3-methoxy-2-neopentyloxybenzaldehyde (419 mg, 1.890 mmol) in presence of sodium ethoxide (183 mg, 2.70 mmol) in ethanol (15 ml) according to the procedure described in Example 24 to give 290 mg of the desired product; $^1$H NMR (300 MHz, DMSO-d$_6$) δ 1.00 (s, 9H), 3.52 (s, 2H), 3.77 (s, 3H), 6.82 (d, J=15.9 Hz, 1H), 6.95-6.99 (m, 3H), 7.50 (d, J=3.9 Hz 1H), 7.57-7.59 (m, 2H), 7.81-7.83 (m, 2H), 8.00 (d, J=3.9 Hz, 1H), 8.25 (m, J=15.0 Hz, 1H); ESI-MS (m/z) 515.45 (M+H)$^+$.

Example 30

3-{2-Methoxy-6-{[(E)-2-{5-oxo-6-[4-(trifluoromethyl)phenyl]-5H-[1,3]thiazolo[3,2-a]pyrimidin-7-yl}-1-ethenyl]phenoxy)propyl cyanide The title compound was prepared by condensation of Intermediate 5 (330 mg, 1.114 mmol) with 4-(2-formyl-6-methoxyphenoxy) butyronitrile (366 mg, 1.671 mmol) in presence of sodium ethoxide (152 mg, 2.247 mmol) in ethanol (15 ml) according to the procedure described in Example 24 to give 222 mg of the desired product as a pale yellow solid; $^1$H NMR (300 MHz, DMSO-d$_6$) δ 1.82 (t, J=6.0 Hz, 2H), 2.67 (t, J=6.6 Hz, 2H), 3.79 (s, 3H), 3.85-3.91 (m, 2H), 6.86-6.91 (m, 2H), 6.96-7.02 (m, 2H), 7.54 (d, J=4.8 Hz, 1H), 7.58 (d, J=7.8 Hz, 2H), 7.83 (d, J=7.8 Hz, 2H), 8.03-8.08 (m, 2H); ESI-MS (m/z) 512.18 (M+H)$^+$.

Example 31

{7-[(E)-2-(2-Methoxyethoxy-3-methoxy)phenyl}vinyl]-6-[4-(trifluoromethyl)phenyl]-5H-[1,3]thiazolo[3,2-a]pyrimidin-5-one The title compound was prepared by condensation of Intermediate 5 (400 mg, 1.281 mmol) with (2-methoxyethoxy)-3-methoxy)benzaldehyde (406 mg, 1.932 mmol) in presence of sodium ethoxide (175 mg, 2.573 mmol) in ethanol (15 ml) according to the procedure described in Example 24 to afford 107 mg of the desired product as a pale yellow solid; $^1$H NMR (300 MHz, CDCl$_3$) δ 3.46-3.52 (m, 3H), 3.60-3.70 (m, 2H), 3.80-3.89 (m, 3H), 4.10-4.20 (m, 2H), 6.86-6.95 (m, 5H), 7.49-7.56 (m, 2H), 7.65-7.71 (m, 2H), 7.90-7.97 (m, 1H), 8.30-8.40 (m, 1H); ESI-MS (m/z) 503.43 (M+H)$^+$ Example 32

{7-[(E)-2-(2-Ethoxyethoxy)-3-methoxy)phenyl-1-ethenyl]-6-[4-(trifluoro methyl)phenyl]-5H-[1,3]thiazolo[3,2-a]pyrimidin-5-one The title compound was prepared by condensation of Intermediate 5 (350 mg, 1.072 mmol) with (2-ethoxyethoxy)-3-methoxy)benzaldehyde (372 mg, 1.501 mmol) in presence of sodium ethoxide (146 mg, 2.147 mmol) in ethanol (15 ml) according to the procedure described in Example 24 to afford 261 mg of the desired product as a pale yellow solid; $^1$H NMR (300 MHz, DMSO-d$_6$) δ 1.15 (t, J=6.6 Hz, 3H), 3.44-3.53 (m, 4H), 3.77 (s, 3H), 4.00-4.06 (m, 2H), 6.79 (d, J=15.0 Hz, 1H), 6.88 (d, J=5.1 Hz, 1H), 6.99 (d, J=4.5 Hz, 2H), 7.52 (d, J=5.1 Hz, 1H), 7.58 (d, J=7.8 Hz, 2H), 7.82 (d, J=8.1 Hz, 2H), 8.01 (d, J=5.1 Hz, 1H), 8.19 (d, J=15.6 Hz, 1H); ESI-MS (m/z) 515.80 (M+H)$^+$.

Example 33

{7-[(E)-2-(2-Cyclopropylmethoxy)-3-methoxyphenyl]-1-ethenyl]-6-[4-(trifluoro methyl)phenyl]-5H-[1,3]thiazolo[3,2-a]pyrimidin-5-one The title compound was prepared by condensation of Intermediate 5 (210 mg, 0.670 mmol) with 2-cyclopropylmethoxy-3-methoxybenzaldehyde (207 mg, 1.00 mmol) in presence of sodium ethoxide (91 mg, 1.310 mmol) in ethanol (15 ml) according to the procedure described in Example 24 to yield 106 mg of the desired product as a pale yellow solid; $^1$H NMR (300 MHz, DMSO-$d_6$) δ 0.23-0.25 (m, 2H), 0.46-0.49 (m, 2H), 3.65-3.68 (m, 2H), 3.76 (s, 3H), 6.88-6.98 (m, 4H), 7.51-7.59 (m, 3H), 7.80-7.83 (m, 2H), 7.99-8.01 (m, 1H), 8.16 (d, J=16.2 Hz, 1H); ESI-MS (m/z) 499.36 (M+H)$^+$.

Example 34

7-[(E)-2-(2-Cyclobutylmethoxy-3-methoxyphenyl)-1-ethenyl]-6-[4-(trifluoro methyl)phenyl]-5H-[1,3]thiazolo[3,2-a]pyrimidin-5-one The title compound was synthesized by condensation of Intermediate 5 (400 mg, 1.289 mmol) with 2-cyclobutyl-methoxy-3-methoxybenzaldehyde (368 mg, 1.603 mmol) in the presence of sodium ethoxide (163 mg, 2.411 mmol) in ethanol (15 ml) according to the procedure described in Example 24 to give 310 mg of the desired product as an off-white solid; $^1$H NMR (300 MHz, DMSO-$d_6$) δ 1.80-1.86 (m, 5H), 1.98-2.04 (m, 2H), 3.77 (s, 3H), 3.82 (d, J=6.9 Hz, 2H), 6.87-7.00 (m, 4H), 7.51 (d, J=7.5 Hz, 1H), 7.59 (d, J=7.8 Hz, 2H), 7.84 (d, J=7.8 Hz, 2H), 8.01 (d, J=4.8 Hz, 1H) 8.14 (d, J=15.6 Hz, 1H); ESI-MS (m/z) 513.30 (M+H)$^+$.

Example 35

7-[(E)-2-(2-Cyclopentyloxy-3-methoxyphenyl)-1-ethenyl]-6-[4-(trifluoro methyl)phenyl]-5H-[1,3]thiazolo[3,2-a]pyrimidin-5-one The title compound was prepared by condensation of Intermediate 5 (400 mg, 1.289 mmol) with 2-cyclopentyloxy-3-methoxybenzaldehyde (398 mg, 1.813 mmol) in presence of sodium ethoxide (163 mg, 2.411 mmol) in ethanol (15 ml) according to the procedure described in Example 24 to afford 296 mg of the desired product as an off-white solid; $^1$H NMR (300 MHz, DMSO-$d_6$) δ 1.50-1.60 (m, 6H), 1.74-1.81 (m, 2H), 3.77 (s, 3H), 4.83 (s, 1H), 6.85-6.99 (m, 4H), 7.51 (d, J=5.1 Hz, 1H), 7.58 (d, J=8.1 Hz, 2H), 7.83 (d, J=7.2 Hz, 2H), 8.00 (d, J=4.8 Hz, 1H), 8.12 (d, J=15.6 Hz, 1H); ESI-MS (m/z) 529.30 (M+H)$^+$.

Example 36

7-[(E)-2-{3-Methoxy-2-(pyridin-2-ylmethoxy)phe-nylvinyl]-6-[4-(trifluoro methyl)phenyl]-5H-[1,3]thiazolo[3,2-a]pyrimidin-5-one The title compound was synthesized by condensation of Intermediate 5 (350 mg, 1.127 mmol) with 3-methoxy-2-(pyridin-2-ylmethoxy)benzaldehyde (411 mg, 1.692 mmol) in presence of sodium ethoxide (153 mg, 2.207 mmol) in ethanol (20 ml) according to the procedure described in Example 24 to give 289 mg of the desired product as an off-white solid; $^1$H NMR (300 MHz, DMSO-$d_6$) δ 3.81 (s, 3H), 5.00 (s, 2H), 6.79 (d, J=16.2 Hz, 1H), 6.90-6.98 (m, 1H), 7.05 (d, J=4.5 Hz, 2H), 7.30-7.36 (m, 1H), 7.46-7.60 (m, 4H), 7.72-7.84 (m, 3H), 7.99-8.04 (m, 1H), 8.10 (d, J=15.6 Hz, 1H), 8.48-8.56 (m, 1H); ESI-MS (m/z) 512.18 (M+H)$^+$.

Example 37

7-[(E)-2-(3-Cyclopropylmethoxy-4-methoxyphenyl)-1-ethenyl]-6-[4-(trifluoro methyl)-phenyl]-5H-[1,3]thiazolo[3,2-a]pyrimidin-5-one

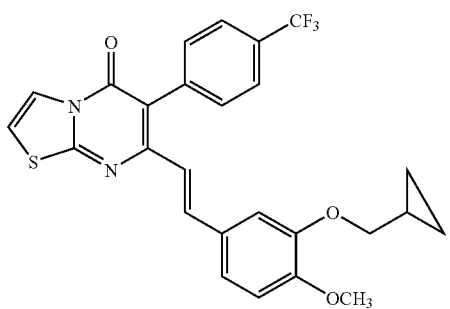

The title compound was synthesized by condensation of Intermediate 5 (400 mg, 1.350 mmol) with 3-cyclopropyl-methoxy-4-methoxybenzaldehyde (417 mg, 2.025 mmol) in presence of sodium ethoxide (183 mg, 2.701 mmol) in ethanol (20 ml) according to the procedure described in Example 24 to give 289 mg of the desired product as an off-white solid; $^1$H NMR (300 MHz, DMSO-$d_6$) δ 0.23-0.30 (m, 2H), 0.50-0.58 (m, 2H), 1.12-1.18 (m, 1H), 3.72-3.80 (m, 5H), 6.60 (d, J=15.6 Hz, 1H) 6.94-7.00 (m, 3H), 7.48-7.53 (m, 1H), 7.58-7.64 (m, 2H), 7.78-7.84 (m, 3H), 7.98-8.05 (m, 1H); ESI-MS (m/z) 499.12 (M+H)$^+$.

Example 38

7-[(E)-2-(4-Cyclopropylmethoxy-3-methoxyphenyl)-1-ethenyl]-6-[4-(trifluoro methyl)-phenyl]-5H-[1,3]thiazolo[3,2-a]pyrimidin-5-one

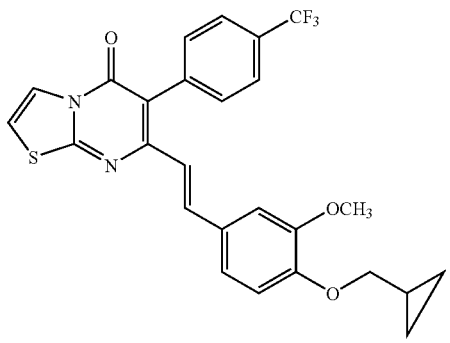

The title compound was synthesized by condensation of Intermediate 5 (400 mg, 1.289 mmol) with 4-cyclopropyl-methoxy-3-methoxybenzaldehyde (345 mg, 1.602 mmol) in presence of sodium ethoxide (163 mg, 2.418 mmol) in ethanol (20 ml) according to the procedure described in Example 24 to give 297 mg of the desired product as an off-white solid; $^1$H NMR (300 MHz, DMSO-$d_6$) δ 0.35 (d, J=4.2 Hz, 2H), 0.64 (d, J=7.8 Hz, 2H), 1.30-1.38 (m, 1H), 3.83 (s, 3H), 3.84 (d, J=8.7 Hz, 2H), 6.70 (d, J=15.6 Hz, 1H), 6.80 (d, J=8.1 Hz, 1H), 6.85-6.92 (m, 1H), 6.94-7.00 (m, 2H), 7.53 (d, J=8.1 Hz, 2H), 7.71 (d, J=7.8 Hz, 2H), 7.84 (d, J=15.0 Hz, 1H), 7.95 (d, J=5.1 Hz, 1H); ESI-MS (m/z) 499.32 (M+H)+.

Example 39

7-[(E)-2-Pyridin-3-ylvinyl]-6-[4-(trifluoromethyl)phenyl]-5H-[1,3]thiazolo[3,2-a]pyrimidin-5-one

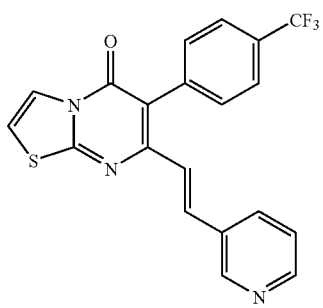

The title compound was synthesized by condensation of Intermediate 5 (400 mg, 1.289 mmol) with pyridine-3-carbaldehyde (200 mg, 1.867 mmol) in presence of sodium ethoxide (175 mg, 2.578 mmol) in ethanol (20 ml) according to the procedure described in Example 24 to give 267 mg of the desired product as a pale yellow solid; ¹H NMR (300 MHz, DMSO-d₆) δ 6.91 (d, J=15.6 Hz, 1H), 7.31-7.38 (m, 1H), 7.55-7.61 (m, 3H), 7.80-7.88 (m, 4H), 8.00-8.06 (m, 1H), 8.41-8.49 (m, 1H), 8.65-8.72 (m, 1H); ESI-MS (m/z) 400.25 (M+H)+.

Example 40

7-[(E)-2-(2-Cyclopropylmethoxy-3-methoxyphenyl)-1-ethenyl]-6-[3-(trifluoro methyl)phenyl]-5H-[1,3]thiazolo[3,2-a]pyrimidin-5-one

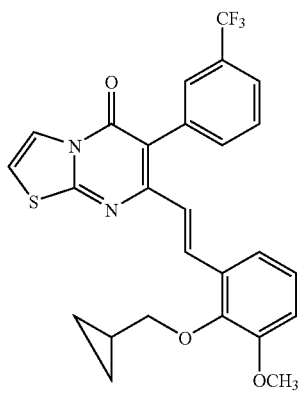

The title compound was prepared by condensation of Intermediate 6 (175 mg, 0.561 mmol) with 2-cyclopropylmethoxy-3-methoxybenzaldehyde (150 mg, 0.783 mmol) in presence of sodium ethoxide (76 mg, 1.118 mmol) in ethanol (10 ml) according to the procedure of Example 24 afforded 115 mg of the desired product as an off-white solid; ¹H NMR (300 MHz, DMSO-d₆) δ 0.24 (d, J=4.2 Hz, 2H), 0.48 (d, J=5.7 Hz, 2H), 0.93-0.99 (m, 1H), 3.67 (d, J=6.6 Hz, 2H), 3.77 (s, 3H), 6.85-7.01 (m, 4H), 7.53 (d, J=4.8 Hz, 1H), 7.66-7.76 (m, 4H), 8.00 (d, J=4.8 Hz, 1H), 8.16 (d, J=15.3 Hz, 1H); ESI-MS (m/z) 499.13 (M+H)+.

Example 41

6-(4-Dimethylaminophenyl)-7-[(E)-2-(2-isobutoxy-3-methoxyphenyl)-1-ethenyl]-5H-[1,3]thiazolo[3,2-a]pyrimidin-5-one

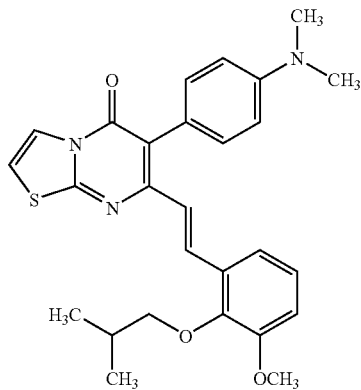

The title compound was prepared from Intermediate 7 (100 mg, 0.207 mmol), 4-N,N-dimethylaminophenylboronic acid (47 mg, 0.290 mmol), Pd[(C₆H₅)₃P]₄ (10 mg, 0.009 mmol) and sodium carbonate (131 mg, 1.244 mmol) in a mixture of toluene, ethanol and water according to the procedure outlined in Example 1 to afford a crude product which was purified by silica gel column chromatography using 10% ethyl acetate in chloroform to give 75 mg of the product; ¹H NMR (300 MHz, DMSO-d₆) δ 0.98 (d, J=6.9 Hz, 6H), 1.85-1.89 (m, 1H), 2.95 (s, 6H), 3.62 (d, J=6.3 Hz, 2H), 3.77 (s, 3H), 6.77 (d, J=9.0 Hz, 2H), 6.82-6.92 (m, 1H), 6.98-7.04 (m, 3H), 7.15 (d, J=9.0 Hz, 1H), 7.45 (d, J=4.8 Hz, 1H), 7.95 (d, J=4.8 Hz, 1H), 8.08 (d, J=15.6 Hz, 1H); ESI-MS (m/z) 476.46 (M+H)+.

Example 42

6-(4-Dimethylaminophenyl)-7-[(E)-2-(3-methoxy-2-neopentyloxy)phenyl-1-ethenyl]-5H-[1,3]thiazolo[3,2-a]pyrimidin-5-one

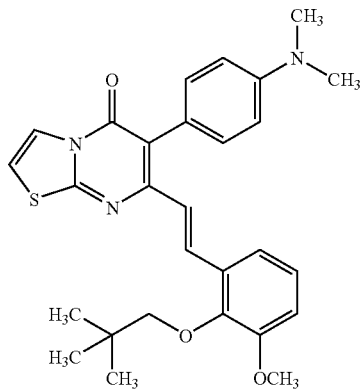

The title compound was prepared from Intermediate 8 (100 mg, 0.207 mmol), 4-N,N-dimethylaminophenylboronic acid (36 mg, 0.221 mmol), Pd[(C₆H₅)₃P]₄ (9 mg, 0.008 mmol) and sodium carbonate (133 mg, 1.244 mmol) in a mixture of toluene, ethanol and water according to the procedure outlined in Example 1 to afford a crude product which was purified by silica gel column chromatography using 50% ethyl acetate in DCM to give 79 mg of the product; $^1$H NMR (300 MHz, DMSO-$d_6$) δ 1.04 (s, 9H), 2.96 (s, 6H), 3.53 (s, 2H), 3.77 (s, 3H), 6.82 (s, 1H), 6.87-6.89 (m, 2H), 6.90-6.98 (m, 3H), 7.14-7.17 (m, 2H), 7.44 (d, J=4.8 Hz, 1H), 7.94 (d, J=4.2 Hz, 1H), 8.16-8.21 (m, 1H); ESI-MS (m/z) 490.43 (M+H)$^+$.

Example 43

7-[(E)-2-(2-Cyclopropylmethoxy-3-methoxyphenyl)-1-ethenyl]-6-(4-methoxy-phenyl)-5H-[1,3]thiazolo[3,2-a]pyrimidin-5-one

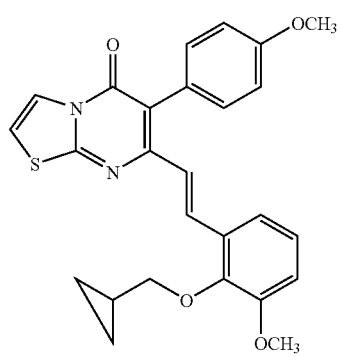

The title compound was prepared by condensation of Intermediate 9 (350 mg, 1.283 mmol) with 2-cyclopropylmethoxy-3-methoxybenzaldehyde (371 mg, 1.799 mmol) in presence of sodium ethoxide (174 mg, 2.570 mmol) in ethanol (10 ml) according to the procedure of Example 24 afforded 255 mg of the desired product as a pale yellow solid; $^1$H NMR (300 MHz, DMSO-$d_6$) δ 0.25-0.27 (m, 2H), 0.49-0.51 (m, 2H), 1.03-1.05 (m, 1H), 3.67-3.70 (m, 2H), 3.77-3.81 (m, 3H), 6.89-6.91 (m, 2H), 6.98-7.02 (m, 4H), 7.23-7.26 (m, 2H), 7.47-7.49 (m, 1H), 7.96-8.10 (m, 1H), 8.10-8.15 (m, 1H); ESI-MS (m/z) 461.39 (M+H)$^+$.

Example 44

7-[(E)-2-(2-Cyclopropylmethoxy-3-methoxyphenyl)-1-ethenyl]-6-(4-ethoxy phenyl)-5H-[1,3]thiazolo[3,2-a]pyrimidin-5-one

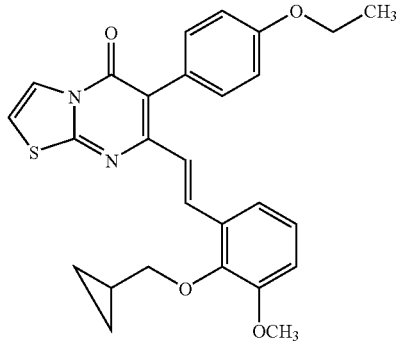

The title compound was prepared by condensation of Intermediate 10 (300 mg, 1.047 mmol) with 2-cyclopropylmethoxy-3-methoxybenzaldehyde (302 mg, 1.466 mmol) in presence of sodium ethoxide (142 mg, 2.090 mmol) in ethanol (10 ml) according to the procedure of Example 24 to afford 200 mg of the desired product as a pale yellow solid; $^1$H NMR (300 MHz, DMSO-$d_6$) δ 0.25-0.27 (m, 2H), 0.49-0.51 (m, 2H), 1.03-1.05 (m, 1H), 3.67-3.70 (m, 2H), 3.77-3.81 (m, 3H), 6.89-6.91 (m, 2H), 6.98-7.02 (m, 4H), 7.23-7.26 (m, 2H), 7.47-7.49 (m, 1H), 7.96-8.10 (m, 1H), 8.10-8.15 (m, 1H); ESI-MS (m/z) 461.39 (M+H)$^+$.

Example 45

7-[(E)-2-(2-Cyclopropylmethoxy-3-methoxyphenyl)-1-ethenyl]-6-(4-(2,2,2-tri fluoroethoxy)phenyl]-5H-[1,3]thiazolo[3,2-a]pyrimidin-5-one

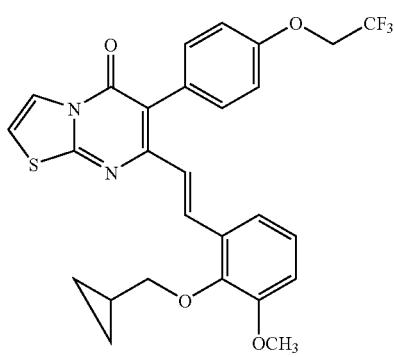

The title compound was synthesized by condensation of Intermediate 11 (325 mg, 0.95 mmol) with 2-cyclopropylmethoxy-3-methoxybenzaldehyde (255 mg, 1.20 mmol) in presence of sodium ethoxide (129 mg, 1.90 mmol) in ethanol (25 ml) according to the procedure of Example 24 to give 235 mg of the desired product; $^1$H NMR (300 MHz, DMSO-$d_6$) δ 0.27 (br s, 2H), 0.51 (br s, 2H), 1.04-1.06 (m, 1H), 3.68-3.70 (m, 2H), 3.77 (m, 3H), 4.81-4.83 (m, 2H), 6.89-6.98 (m, 4H), 7.13-7.15 (m, 2H), 7.27-7.29 (m, 2H), 7.49 (br s, 1H), 7.98 (br s, 1H), 8.14 (d, J=16.2 Hz, 1H); ESI-MS (m/z) 529.23 (M+H)$^+$.

Example 46

3-4-{7-[(E)-2-(2-Cyclopropylmethoxy-3-methoxyphenyl)-1-ethenyl]-5H-[1,3]thiazolo-[3,2-a]pyrimidin-6-yl}phenoxy)propyl cyanide

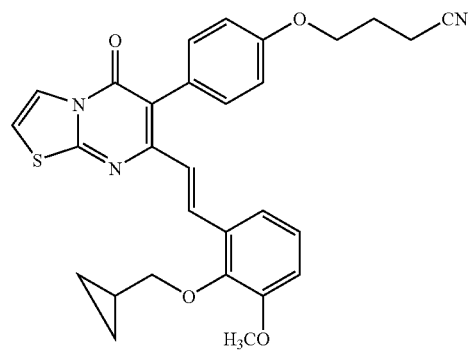

The title compound was synthesized by condensation of Intermediate 12 (200 mg, 0.614 mmol) with 2-cyclopropylmethoxy-3-methoxybenzaldehyde (27 mg, 0.676 mmol) in presence of sodium hydride (16 mg, 0.676 mmol) according to the procedure of Example 24 to give 106 mg of the desired product; $^1$H NMR (300 MHz, DMSO-$d_6$) δ 0.25-0.27 (m, 2H), 0.49-0.51 (m, 2H), 1.02-1.06 (m, 1H), 2.04-2.06 (m, 2H), 2.66-2.71 (m, 2H), 3.67-3.69 (m, 2H), 3.76 (s, 3H), 4.07-4.08 (m, 2H), 6.80-6.91 (m, 2H), 6.96-7.03 (m, 4H), 7.23-7.26 (m, 2H), 7.47-7.49 (m, 1H), 7.96-7.98 (m, 1H), 8.12 (d, J=15.9 Hz, 1H); ESI-MS (m/z) 514.24 (M+H)$^+$.

Example 47

7-[(E)-2-(2-Cyclopropylmethoxy-3-methoxyphenyl)-1-ethenyl]-6-(4-cyclopropyl methoxyphenyl]-5H-[1,3]thiazolo[3,2-a]pyrimidin-5-one

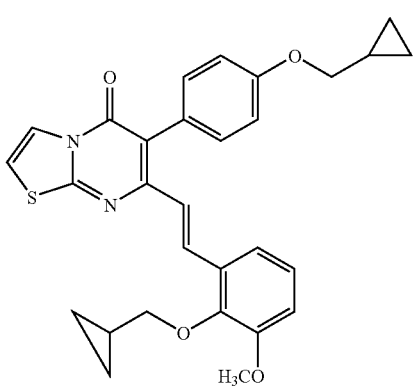

The title compound was synthesized by condensation of Intermediate 13 (475 mg, 1.5 mmol) with (2-cyclopropyl-methoxy-3-methoxybenzaldehyde (407 mg, 1.9 mmol) in the presence of sodium ethoxide (204 mg, 3.0 mmol) in ethanol (25 ml) according to the procedure of Example 24 to give 320 mg of the desired product; $^1$H NMR (300 MHz, DMSO-$d_6$) δ 0.27-0.35 (m, 4H), 0.50-0.59 (m, 4H), 1.05 (br s, 1H), 1.25 (br s, 1H), 3.69-3.85 (m, 7H), 6.8-6.99 (m, 6H), 7.22 (br s, 2H), 7.49 (br s, 1H), 7.97 (br s, 1H), 8.05-8.15 (m, 1H); ESI-MS (m/z) 501.30 (M+H)$^+$.

Example 48

7-[(E)-2-(2-Cyclopropylmethoxy-3-methoxyphenyl)-1-ethenyl]-6-(4-difluoro methoxyphenyl]-5H-[1,3]thiazolo[3,2-a]pyrimidin-5-one

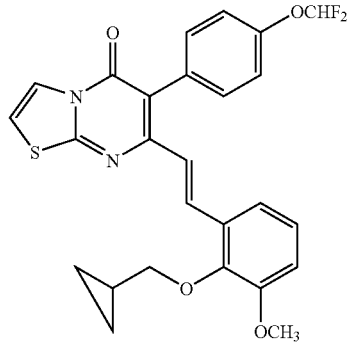

The title compound was synthesized by condensation of Intermediate 14 (250 mg, 0.811 mmol) with 2-cyclopropyl-methoxy-3-methoxybenzaldehyde (234 mg, 1.136 mmol) in presence of sodium ethoxide (110 mg, 1.623 mmol) according to the procedure of Example 23 to give 158 mg of the desired product; $^1$H NMR (300 MHz, DMSO-$d_6$) δ 0.26-0.28 (m, 2H), 0.49-0.51 (m, 2H), 1.02-1.04 (m, 1H), 3.69 (m, 2H), 3.77 (s, 3H), 6.93-7.08 (m, 4H), 7.27-7.57 (m, 6H), 7.99 (br s, 1H), 8.15 (d, J=16.2 Hz, 1H); ESI-MS (m/z) 497.28 (M+H)$^+$.

Example 49

7-[(E)-2-(2-Cyclopropylmethoxy-3-fluorophenyl)-1-ethenyl]-6-[4-(trifluoro methoxy)-phenyl]-5H-[1,3]thiazolo[3,2-a]pyrimidin-5-one

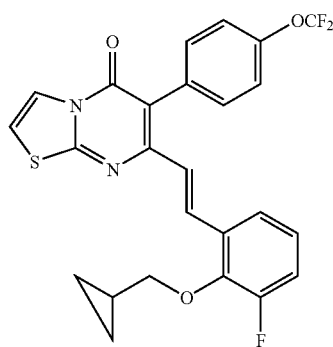

The title compound was synthesized by condensation of Intermediate 15 (350 mg, 1.071 mmol) with 2-cyclopropyl-methoxy-3-fluorobenzaldehyde (291 mg, 1.501 mmol) in presence of sodium ethoxide (146 mg, 2.147 mmol) in ethanol (15 ml) according to the procedure outlined in Example 24 to give 241 mg of the desired product as a light yellow solid; $^1$H NMR (300 MHz, DMSO-$d_6$) δ 0.23 (d, J=4.8 Hz, 2H), 0.48 (d, J=6.6 Hz, 2H), 0.95-1.05 (m, 1H), 3.77 (d, J=6.9 Hz, 2H), 7.00-7.09 (m, 2H), 7.15-7.23 (m, 2H), 7.42-7.50 (m, 4H), 7.53 (d, J=4.8 Hz, 1H), 7.98-8.08 (m, 2H); ESI-MS (m/z) 503.55 (M+H)$^+$.

Example 50

7-[(E)-2-{2-Isopentyloxy-3-methoxyphenyl}-1-ethenyl]-6-[4-(trifluoro methoxy)phenyl]-5H-[1,3]thiazolo[3,2-a]pyrimidin-5-one

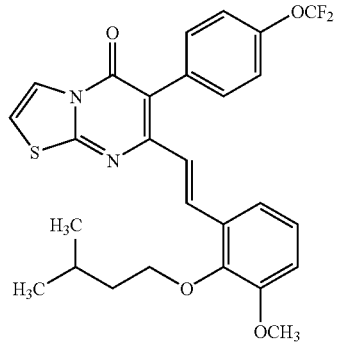

The title compound was prepared by condensation of Intermediate 15 (350 mg, 1.071 mmol) with 2-isopentyloxy-3-methoxybenzaldehyde (334 mg, 1.501 mmol) in the presence of sodium ethoxide (146 mg, 2.147 mmol) in ethanol (15 ml) according to the procedure outlined in Example 24 to afford 280 mg of the desired product as a light yellow solid; $^1$H NMR (300 MHz, DMSO-d$_6$) δ 0.93 (d, J=6.3 Hz, 6H), 1.45 (q, J=6.6 Hz, 2H), 1.85-1.91 (m, 1H), 3.77 (s, 3H), 3.86 (t, J=6.6 Hz, 2H), 6.86-6.94 (m, 2H), 7.00-7.06 (m, 2H), 7.46-7.51 (m, 5H), 7.99 (d, J=4.8 Hz, 1H), 8.07 (d, J=15.6 Hz, 1H); ESI-MS (m/z) 531.20 (M+H)$^+$.

Examples 51-69, outlined in Table 4, were prepared in a single step from Intermediate 15 and the appropriate aldehydes using procedure similar to that for Example 24

TABLE 4

Structural details of Examples 51-74

| Example | $R^{a1}$ | $R^{a2}$ | Mol. Formula |
|---|---|---|---|
| Example 51 | CH$_2$CH(CH$_3$)$_2$ | CH$_3$ | C$_{26}$H$_{23}$F$_3$N$_2$O$_4$S |
| Example 52 | CH$_2$C(CH$_3$)$_3$ | CH$_3$ | C$_{27}$H$_{25}$F$_3$N$_2$O$_4$S |
| Example 53 | CH$_2$CH$_2$OC$_2$H$_5$ | CH$_3$ | C$_{26}$H$_{23}$F$_3$N$_2$O$_5$S |
| Example 54 | CH$_2$CH$_2$CH$_3$ | CH$_3$ | C$_{25}$H$_{21}$F$_3$N$_2$O$_4$S |
| Example 55 | CH$_2$(CH$_2$)$_3$CH$_3$ | CH$_3$ | C$_{27}$H$_{25}$F$_3$N$_2$O$_4$S |
| Example 56 | CH$_2$(CH$_2$)$_3$F | CH$_3$ | C$_{26}$H$_{22}$F$_4$N$_2$O$_4$S |
| Example 57 | CH$_2$(CH$_2$)$_2$CH$_3$ | CH$_3$ | C$_{26}$H$_{23}$F$_3$N$_2$O$_4$S |
| Example 58 | cyclopropyl-CH$_2$-C(CH$_3$)- | CH$_3$ | C$_{26}$H$_{21}$F$_3$N$_2$O$_4$S |
| Example 59 | H | H | C$_{21}$H$_{13}$F$_3$N$_2$O$_4$S |
| Example 60 | cyclopropyl-CH$_2$-C(CH$_3$)- | H | C$_{25}$H$_{19}$F$_3$N$_2$O$_4$S |
| Example 61 | cyclopropyl-CH$_2$-C(CH$_3$)- | C$_2$H$_5$ | C$_{27}$H$_{23}$F$_3$N$_2$O$_4$S |
| Example 62 | cyclopropyl-CH$_2$-C(CH$_3$)- | CH$_2$CH$_2$OC$_2$H$_5$ | C$_{29}$H$_{27}$F$_3$N$_2$O$_5$S |
| Example 63 | cyclopropyl-CH$_2$-C(CH$_3$)- | CHF$_2$ | C$_{26}$H$_{19}$F$_5$N$_2$O$_4$S |
| Example 64 | cyclopropyl-CH$_2$-C(CH$_3$)- | cyclopropyl-CH$_2$-C(CH$_3$)- | C$_{29}$H$_{25}$F$_3$N$_2$O$_4$S |
| Example 65 | cyclopropyl-CH$_2$-C(CH$_3$)- | CH$_2$(CH$_2$)$_2$CN | C$_{29}$H$_{24}$F$_3$N$_3$O$_4$S |
| Example 66 | cyclopropyl-CH$_2$-C(CH$_3$)- | CH$_2$CH$_2$CH$_3$ | C$_{28}$H$_{25}$F$_3$N$_2$O$_4$S |
| Example 67 | cyclobutyl-CH$_2$-C(CH$_3$)- | CH$_3$ | C$_{27}$H$_{23}$F$_3$N$_2$O$_4$S |
| Example 68 | cyclopentyl-C(CH$_3$)- | CH$_3$ | C$_{27}$H$_{23}$F$_3$N$_2$O$_4$S |
| Example 69 | H | CH$_3$ | C$_{22}$H$_{15}$F$_3$N$_2$O$_4$S |
| Example 70 | CH$_2$CH$_2$CF$_3$ | CH$_3$ | C$_{25}$H$_{18}$F$_6$N$_2$O$_4$S |

TABLE 4-continued

Structural details of Examples 51-74

| Example | $R^{a1}$ | $R^{a2}$ | Mol. Formula |
|---|---|---|---|
| Example 71 | cyclohexyl-CH₂-CH(—)— (with wavy bond) | CH₃ | $C_{29}H_{27}F_3N_2O_4S$ |
| Example 72 | cyclohexyl-CH(—)(CH₃)— | CH₃ | $C_{28}H_{25}F_3N_2O_4S$ |
| Example 73 | CH₂CH₂OCH₃ | CH₃ | $C_{25}H_{21}F_3N_2O_5S$ |
| Example 74 | CH₂(CH₂)₂CN | CH₃ | $C_{26}H_{20}F_3N_3O_4S$ |

Example 51

7-[(E)-2-(2-Isobutoxy-3-methoxyphenyl)-1-ethenyl]-6-[4-(trifluoromethoxy)phenyl]-5H-[1,3]thiazolo[3,2-a]pyrimidin-5-one The title compound was synthesized by condensation of Intermediate 15 (350 mg, 1.071 mmol) with 2-isobutoxy-3-methoxybenzaldehyde (312 mg, 1.516 mmol) in the presence of sodium ethoxide (146 mg, 2.147 mmol) in ethanol (15 ml) according to the procedure of Example 24 to give 187 mg of the desired product as a light yellow solid; $^1$H NMR (300 MHz, DMSO-d$_6$) δ 0.90-0.99 (m, 6H), 1.80-1.86 (m, 1H), 3.58-3.65 (m, 2H), 3.77 (s, 3H), 6.85-6.93 (m, 2H), 6.99-7.06 (m, 2H), 7.40-7.50 (m, 5H), 7.96-8.02 (m, 1H), 8.09-8.14 (m, 1H); ESI-MS (m/z) 517.18 (M+H)$^+$.

Example 52

7-[(E)-2-{3-Methoxy-2-neopentyloxyphenyl}-1-ethenyl]-6-[4-(trifluoromethoxy)phenyl]-5H-[1,3]thiazolo[3,2-a]pyrimidin-5-one The title compound was prepared by condensation of Intermediate 15 (400 mg, 1.225 mmol) with 3-methoxy-2-neopentyloxybenzaldehyde (353 mg, 1.50 mmol) in the presence of sodium ethoxide (163 mg, 2.40 mmol) in ethanol (15 ml) according to the procedure outlined in Example 24 to afford 320 mg of the desired product as a pale yellow solid; $^1$H NMR (300 MHz, DMSO-d$_6$) δ 1.01 (s, 9H), 3.52 (s, 2H), 3.77 (s, 3H), 6.82 (d, J=16.2 Hz, 1H), 6.92-6.94 (m, 1H), 6.99 (s, 2H), 7.48 (m, 5H), 7.98 (d, J=5.1 Hz, 1H), 8.22 (d, J=15.6 Hz, 1H); ESI-MS (m/z) 531.35 (M+H)$^+$.

Example 53

7-[(E)-2-{2-(2-Ethoxyethoxy)-3-methoxyphenyl}-1-ethenyl]-6-[4-(trifluoro methoxy)phenyl]-5H-[1,3]thiazolo[3,2-a]pyrimidin-5-one The title compound was synthesized by condensation of Intermediate 15 (400 mg, 1.225 mmol) with [2-(2-ethoxyethoxy)-3-methoxy]benzaldehyde (384 mg, 1.716 mmol) in presence of sodium ethoxide (166 mg, 2.471 mmol) in ethanol (15 ml) according to the procedure of Example 24 to give 291 mg of the desired product as a pale yellow solid; $^1$H NMR (300 MHz, DMSO-d$_6$) δ 1.15 (t, J=7.2 Hz, 3H), 3.45-3.51 (m, 4H), 3.78 (s, 3H), 4.00-4.08 (m, 2H), 6.80 (d, J=15.6 Hz, 1H), 6.82-6.89 (m, 1H), 6.99 (d, J=4.8 Hz, 1H), 7.00 (d, J=4.2 Hz, 2H), 7.40-7.48 (m, 4H), 7.51 (d, J=6.3 Hz, 1H), 8.00 (d, J=7.2 Hz, 1H), 8.17 (d, J=15.6 Hz, 1H); ESI-MS (m/z) 533.25 (M+H)$^+$.

Example 54

7-[(E)-2-(3-Methoxy-2-propoxyphenyl)-1-ethenyl]-6-[4-(trifluoromethoxy)phenyl]-5H-[1,3]thiazolo[3,2-a]pyrimidin-5-one The title compound was prepared by condensation of Intermediate 15 (400 mg, 1.225 mmol) with 3-methoxy-2-propoxybenzaldehyde (333 mg, 1.716 mmol) in the presence of sodium ethoxide (176 mg, 2.301 mmol) in ethanol (25 ml) according to the procedure outlined in Example 24 to give 295 mg of the desired product as a light yellow solid; $^1$H NMR (300 MHz, DMSO-d$_6$) δ 0.94 (t, J=7.2 Hz, 3H), 1.53 (q, J=6.9 Hz, 2H), 3.31 (s, 1H), 3.77 (s, 3H), 3.80 (s, 1H), 6.91-6.99 (m, 4H), 7.40-7.46 (m, 4H), 7.50 (d, J=4.8 Hz, 1H), 7.95-8.07 (m, 2H); ESI-MS (m/z) 503.51 (M+H)$^+$.

Example 55

7-[(E)-2-(3-Methoxy-2-pentyloxyphenyl)-1-ethenyl]-6-[4-(trifluoromethoxy)phenyl]-5H-[1,3]thiazolo[3,2-a]pyrimidin-5-one The title compound was synthesized by condensation of Intermediate 15 (350 mg, 1.071 mmol) with 3-methoxy-2-pentyloxybenzaldehyde (333 mg, 1.501 mmol) in presence of sodium ethoxide (146 mg, 2.147 mmol) in ethanol (15 ml) according to the procedure of Example 24 to give 261 mg of the desired product as a light yellow solid; $^1$H NMR (300 MHz, DMSO-d$_6$) δ 0.91 (t, J=6.6 Hz, 3H), 1.33-1.42 (m, 4H), 1.50-1.58 (m, 2H), 3.77 (s, 3H), 3.83 (t, J=6.3 Hz, 2H), 6.85-6.90 (m, 2H), 6.96-7.02 (m, 2H), 7.40-7.47 (m, 4H), 7.51-7.90 (m, 1H), 7.95-8.02 (m, 1H), 8.06-8.12 (m, 1H); ESI-MS (m/z) 531.26 (M+H)$^+$.

Example 56

4-7-[(E)-2-{2-(4-Fluorobutoxy)-3-methoxyphenyl}-1-ethenyl]-6-[4-(trifluoro methoxy)phenyl]-5H-[1,3]thiazolo[3,2-a]pyrimidin-5-one The title compound was prepared by condensation of Intermediate 15 (400 mg, 1.225 mmol) with [2-(4-fluorobutoxy)-

3-methoxy]benzaldehyde (384 mg, 1.716 mmol) in presence of sodium ethoxide (166 mg, 2.471 mmol) in ethanol (25 ml) according to the procedure of Example 24 to give 321 mg of the desired product as a pale yellow solid; $^1$H NMR (300 MHz, DMSO-d$_6$) δ 1.60-1.67 (m, 2H), 1.79-1.88 (m, 2H), 3.77 (s, 3H), 3.86 (t, J=6.0 Hz, 2H), 4.42 (t, J=5.4 Hz, 1H), 4.58 (t, J=6.0 Hz, 1H), 6.85-6.91 (m, 2H), 6.99-7.05 (m, 2H), 7.40-7.48 (m, 4H), 7.51 (d, J=4.8 Hz, 1H), 7.95-8.02 (m, 1H), 8.06-8.12 (m, 2H); ESI-MS (m/z) 536.00 (M+H)$^+$.

Example 57

7-[(E)-2-(2-Butoxy-3-methoxyphenyl)-1-ethenyl]-6-[4-(trifluoromethoxy)phenyl]-5H-[1,3]thiazolo[3,2-a]pyrimidin-5-one The title compound was synthesized by the condensation of Intermediate 15 (400 mg, 1.225 mmol) with 2-butoxy-3-methoxybenzaldehyde (337 mg, 1.716 mmol) in presence of sodium ethoxide (166 mg, 2.457 mmol) in ethanol (25 ml) according to the procedure described in Example 24 to give 281 mg of the desired product as a light yellow solid; $^1$H NMR (300 MHz, DMSO-d$_6$) δ 0.94 (t, J=6.9 Hz, 3H), 1.40-1.52 (m, 4H), 3.77 (s, 3H), 3.80-3.90 (m, 2H), 6.80-6.90 (m, 2H), 6.98-7.05 (m, 2H), 7.40-7.46 (m, 4H), 7.50 (d, J=4.8 Hz, 1H), 7.99 (d, J=6.0 Hz, 1H), 8.07 (d, J=15.6 Hz, 1H); ESI-MS (m/z) 517.15 (M+H)$^+$.

Example 58

7-{(E)-2-[2-(Cyclopropylmethoxy)-3-methoxyphenyl}-1-ethenyl]-6-(4-trifluoro methoxyphenyl)-5H-[1,3]thiazolo[3,2-a]pyrimidin-5-one The title compound was prepared by condensation of Intermediate 15 (370 mg, 1.132 mmol) with 2-cyclopropylmethoxy-3-methoxybenzaldehyde (327 mg, 1.583 mmol) and sodium ethoxide (154 mg, 2.264 mmol) in ethanol (15 ml) according to the procedure described in Example 24 to afford 276 mg of the desired product as a light yellow solid; $^1$H NMR (300 MHz, CDCl$_3$) δ 0.30-0.34 (m, 2H), 0.54-0.60 (m, 2H), 1.17-1.24 (m, 1H), 3.79 (d, J=7.2 Hz, 2H), 3.84 (s, 3H), 6.84-6.87 (m, 1H) 6.96-7.00 (m, 4H) 7.31 (d, J=8.4 Hz, 2H), 7.44 (d, J=8.7 Hz, 2H), 7.96 (d, J=4.8 Hz), 8.33 (d, J=15.6 Hz, 1H); ESI-MS (m/z) 515.18 (M+H)$^+$.

Example 59

7-{(E)-(2,3-Dihydroxy)phenyl}-1-ethenyl]-6-(4-trifluoromethoxy-phenyl)-5H-[1,3]thiazolo[3,2-a]pyrimidin-5-one To a solution of Example 58 (0.500 g, 0.971 mmol) in DCM cooled to −75° C. was added slowly BBr$_3$ in DCM and stirred for 0.5 h. The reaction mixture was then allowed to rise to room temperature and stirred for further 2.0 h. The mixture was concentrated in vacuo. The residue was neutralized with saturated NaHCO$_3$ and extracted with ethyl acetate. The organic layer was dried over anhydrous Na$_2$SO$_4$ and the solvent distilled to afford the desired compound: $^1$H NMR (300 MHz, DMSO-d$_6$) δ 6.54-6.59 (m, 1H), 6.67-6.73 (m, 2H), 6.81 (d, J=15.6 Hz, 1H), 7.37-7.51 (m, 5H), 7.99 (d, J=4.8 Hz, 1H), 8.09 (d, J=15.6 Hz, 1H), 8.87 (br s, 1H), 9.56 (br s, 1H); ESI-MS (m/z) 447.24 (M+H)$^+$.

Example 60

7-{(E)-(2-Cyclopropylmethoxy-3-hydroxy)phenyl]-1-ethenyl}-6-(4-trifluoro-methoxyphenyl)-5H-[1,3]thiazolo[3,2-a]pyrimidin-5-one A solution of Example 59 (850 mg, 1.9 mmol), bromomethylcyclopropane (283 mg, 2.0 mmol) and K$_2$CO$_3$ (315 mg, 2.2 mmol) in DMF was heated at 60° C. for 18.0 h overnight. The reaction mixture was diluted with water, extracted into ethyl acetate. The organic layer was washed with brine, dried, and purified by column chromatography to afford 560 mg of the desired compound; $^1$H NMR (300 MHz, DMSO-d$_6$) 0.26 (d, J=3.6 Hz, 2H), 0.48 (d, J=6.9 Hz, 2H), 1.0-1.10 (m, 1H), 3.68 (d, J=6.9 Hz, 2H), 6.76-6.91 (m, 4H), 7.46-7.50 (m, 5H), 8.00 (d, J=4.8 Hz, 1H), 8.13 (d, J=16.2 Hz, 1H), 9.42 (s, 1H).

Example 61

7-{(E)-2-[2-(Cyclopropylmethoxy)-3-ethoxyphenyl}-1-ethenyl]-6-(4-trifluoro methoxy-phenyl)-5H-[1,3]thiazolo[3,2-a]pyrimidin-5-one A solution of Example 60 (60 mg, 0.119 mmol) in DMF (5 ml) was treated with NaH (6 mg, 0.167 mmol) at 0° C. followed by the addition of ethyl iodide (26 mg, 0.167 mmol). The reaction mixture was then allowed to warm to room temperature and then to 60° C. at which it was heated for 1.0 h. The reaction mixture was diluted with ethyl acetate, washed with water and brine and purified by column chromatography using 5% ethyl acetate in chloroform to afford 30 mg of the desired compound; $^1$H NMR (300 MHz, DMSO-d$_6$) δ 0.25 (d, J=4.5 Hz, 2H), 0.48 (d, J=7.2 Hz, 2H), 0.90-1.01 (m, 1H), 1.33 (t, J=6.9 Hz, 3H), 3.70 (d, J=7.2 Hz, 2H), 4.00 (q, J=6.6 Hz, 2H), 6.89-6.96 (m, 3H), 7.46 (s, 3H), 7.51 (d, J=4.8 Hz, 1H), 7.99 (d, J=5.1 Hz, 1H), 8.12 (d, J=15.3 Hz, 1H); ESI-MS (m/z) 529.43 (M+H)$^+$.

Example 62

7-{(E)-2-[2-(Cyclopropylmethoxy)-3-(2-ethoxyethoxy)phenyl]-1-ethenyl}-6-(4-tri fluoro-methoxyphenyl)-5H-[1,3]thiazolo[3,2-a]pyrimidin-5-one The title compound was synthesized by the reaction of Example 60 (70 mg, 0.130 mmol) with 2-bromoethylethyl ether (29 mg, 0.191 mmol) in the presence of sodium hydride (7 mg, 0.19 mmol) in DMF (2 ml) according to the procedure outlined in Example 61 to give 50 mg of the desired product as a pale yellow solid; $^1$H NMR (300 MHz, DMSO-d$_6$) δ 0.23 (d, J=4.2 Hz, 2H), 0.47 (d, J=7.2 Hz, 2H), 0.96-0.99 (m, 1H), 1.118 (t, J=6.3 Hz 3H), 3.50 (q, J=6.3 Hz, 2H), 3.69-3.73 (m, 4H), 4.07 (s, 2H), 6.92-6.98 (m, 4H), 7.46 (s, 3H), 7.51 (d, J=4.2 Hz, 2H), 8.00 (d, J=3.9 Hz, 1H), 8.12 (d, J=15.6 Hz, 1H); ESI-MS (m/z) 573.76 (M+H)$^+$.

Example 63

7-{(E)-2-[2-(Cyclopropylmethoxy)-3-difluoromethoxyphenyl]-1-ethenyl}-6-(4-tri fluoromethoxyphenyl)-5H-[1,3]thiazolo[3,2-a]pyrimidin-5-one The title compound was prepared using Example 60 (70 mg, 0.13 mmol), Cs$_2$CO$_3$ (84 mg, 0.26 mmol) and ClCHF$_2$ gas in DMF (2 ml) according to the procedure described in Intermediate 14 to afford 58 mg of the desired compound; $^1$H NMR (300 MHz, DMSO-d$_6$) δ 0.25-0.28 (m, 2H), 0.51 (d, J=7.8 Hz, 2H), 0.80-1.10 (m, 1H), 3.69 (d, J=6.9 Hz, 2H), 6.90-7.00 (m, 1H), 7.10-7.15 (m, 2H), 7.27 (d, J=6.9 Hz, 1H), 7.46-7.53 (m, 5H), 8.00 (d, J=4.2 Hz, 1H), 8.09 (d, J=15.0 Hz, 1H); ESI-MS (m/z) 551.36 (M+H)$^+$.

Example 64

7-{(E)-2-[2-(Cyclopropylmethoxy)-3-(cyclopropylmethoxy)phenyl]-1-ethenyl}-6-(4-trifluoromethoxyphenyl)-5H-[1,3]thiazolo[3,2-a]pyrimidin-5-one The title compound was prepared by condensation of Example 60 (70 mg, 0.13 mmol) with bromomethylcyclopropane (26 mg, 0.19 mmol) in DMF (2 ml) using $Cs_2CO_3$ (84 mg, 0.26 mmol) according to the procedure outlined in Example 61 to afford 60 mg of the desired compound; $^1$H NMR (300 MHz, DMSO-$d_6$) δ 0.29 (d, J=3.9 Hz, 2H), 0.31 (d, J=3.9 Hz, 2H), 0.48 (d, J=6.9 Hz, 2H), 0.56 (d, J=7.2 Hz, 3H), 0.90-1.10 (m, 1H), 1.20-1.30 (m, 1H) 3.73 (d, J=6.9 Hz, 2H), 3.81 (d, J=6.3 Hz, 2H) 6.90-6.95 (m, 4H), 7.46-7.52 (m, 5H), 8.00 (d, J=4.8 Hz, 1H), 8.13 (d, J=15.6 Hz, 1H); ESI-MS (m/z) 555.40 (M+H)$^+$.

Example 65

7-{(E)-2-[2-(Cyclopropylmethoxy)-3-(3-cyanopropoxy)phenyl]-1-ethenyl}-6-(4-tri fluoromethoxyphenyl)-5H-[1,3]thiazolo[3,2-a]pyrimidin-5-one The title compound was synthesized by the reaction of Example 60 (60 mg, 0.130 mmol) with NaH and 4-Bromobutyronitrile (28 mg, 0.191 mmol) according to the procedure outlined in Example 61 to afford 50 mg of the desired compound; $^1$H NMR (300 MHz, DMSO-$d_6$) δ 0.25-0.26 (m, 2H), 0.50 (d, J=7.8 Hz, 2H), 0.90-1.10 (m, 1H), 2.04 (t, J=5.7 Hz 2H), 2.65 (t, J=6.9 Hz 2H) 3.70 (d, J=6.9 Hz, 2H), 4.03 (t, J=5.1 Hz 2H), 6.89-7.01 (m, 4H), 7.46-7.52 (m, 5H), 8.00 (d, J=4.8 Hz, 1H), 8.15 (d, J=15.9 Hz, 1H); ESI-MS (m/z) 568.64 (M+H)$^+$.

Example 66

7-{(E)-2-[2-(Cyclopropylmethoxy)-3-propoxyphenyl]-1-ethenyl]-6-(4-trifluoro methoxy-phenyl)-5H-[1,3]thiazolo[3,2-a]pyrimidin-5-one The title compound was synthesized by the reaction of Example 60 (70 mg, 1.3 mmol) with 1-Bromopropane (24 mg, 1.9 mmol) using NaH (7 mg, 0.19 mmol) in DMF according to the procedure described Example 61 to afford 55 mg of the desired compound; $^1$H NMR (300 MHz, DMSO-$d_6$) δ 0.24-0.26 (m, 2H), 0.49 (d, J=7.2 Hz, 2H), 0.99 (t, J=7.5 Hz, 3H), 1.70-1.77 (m, 2H), 3.70 (d, J=3.9 Hz, 2H), 3.89-3.93 (m, 2H), 6.89-6.97 (m, 4H), 7.46-7.52 (s, 5H), 8.00 (d, J=4.5 Hz, 1H), 8.13 (d, J=16.2 Hz, 1H); ESI-MS (m/z) 543.26 (M+H)$^+$.

Example 67

7-[(E)-2-{2-Cyclobutylmethoxy-3-methoxyphenyl}-1-ethenyl]-6-[4-(trifluoro methoxy)-phenyl]-5H-[1,3]thiazolo[3,2-a]pyrimidin-5-one The title compound was prepared by condensation of Intermediate 15 (350 mg, 1.012 mmol) with 2-cyclobutylmethoxy-3-methoxybenzaldehyde (330 mg, 1.501 mmol) in the presence of sodium ethoxide (146 mg, 2.147 mmol) in ethanol (15 ml) according to the procedure described in Example 24 to give 292 mg of the desired product as an off-white solid; $^1$H NMR (300 MHz, DMSO-$d_6$) δ 1.80-1.90 (m, 5H), 2.00-2.08 (m, 2H), 3.77 (s, 3H), 3.83 (d, J=6.9 Hz, 2H), 6.80-6.87 (m, 2H), 6.91-6.99 (m, 2H), 7.40-7.46 (m, 4H), 7.51 (d, J=4.8 Hz, 1H), 7.99 (d, J=3.6 Hz, 1H), 8.12 (d, J=15.6 Hz, 1H); ESI-MS (m/z) 529.13 (M+H)$^+$.

Example 68

7-[(E)-2-{2-(Cyclopentyloxy-3-methoxyphenyl}-1-ethenyl]-6-[4-(trifluoro methoxy)-phenyl]-5H-[1,3]thiazolo[3,2-a]pyrimidin-5-one The title compound was synthesized by condensation of Intermediate 15 (350 mg, 1.012 mmol) with 2-cyclopentyloxy-3-methoxybenzaldehyde (330 mg, 1.501 mmol) in presence of sodium ethoxide (146 mg, 2.147 mmol) in ethanol (15 ml) according to the procedure of Example 24 to give 251 mg of the desired product as a pale yellow solid; $^1$H NMR (300 MHz, DMSO-$d_6$) δ 1.54-1.62 (m, 6H), 1.75-1.82 (m, 2H), 3.77 (s, 3H), 4.80-4.87 (m, 1H), 6.84-6.93 (m, 2H), 6.98 (d, J=4.8 Hz, 2H), 7.46-7.52 (m, 5H), 7.98 (d, J=4.2 Hz, 1H), 8.10 (d, J=15.6 Hz, 1H); ESI-MS (m/z) 529.49 (M+H)$^+$.

Example 69

7-[(E)-2-(2-Hydroxy-3-methoxyphenyl)-1-ethenyl]-6-[4-(trifluoromethoxy)phenyl]-5H-[1,3]thiazolo[3,2-a]pyrimidin-5-one The title compound was prepared by treatment of Example 68 (38 mg, 0.071 mmol) with 48% hydrogen bromide and acetic acid (1:1) (2 ml) to afford 14 mg of the desired product as a pale yellow solid; $^1$H NMR (300 MHz, DMSO-$d_6$) δ 3.78 (s, 3H), 6.71 (t, J=8.1 Hz, 1H), 6.85-6.91 (m, 4H), 7.40-7.46 (m, 3H), 7.51 (d, J=6.1 Hz, 1H), 8.00 (d, J=4.8 Hz, 1H), 8.10 (d, J=15.6 Hz, 1H) 9.17 (br s, 1H); ESI-MS (m/z) 461.35 (M+H)$^+$.

Example 70

7-[(E)-2-{3-Methoxy-2-(2-trifluoromethylethoxy)phenyl}-1-ethenyl]-6-[4-(trifluoromethoxy)phenyl]-5H-[1,3]thiazolo[3,2-a]pyrimidin-5-one The title compound was prepared by treatment of Example 69 (100 mg, 0.210 mmol) with $Cs_2CO_3$ (136 mg, 0.421 mmol) and 1,1,1-trifluoro-3-iodopropane (121 mg, 0.542 mmol) in DMF (3 ml) according to the procedure described in Example 61 to afford the desired compound; $^1$H NMR (300 MHz, DMSO-$d_6$) δ 2.25-2.63 (m, 2H), 3.80 (s, 3H), 4.04-4.08 (m, 2H), 6.89-6.98 (m, 2H), 6.98-7.08 (m, 2H), 7.49-7.54 (m, 5H), 8.01-8.03 (m, 1H), 8.09 (d, J=15.6 Hz, 1H); ESI-MS (m/z) 558.81 (M+H)$^+$.

Example 71

7-[(E)-2-(2-Cyclohexylmethoxy-3-methoxyphenyl)-1-ethenyl]-6-[4-(trifluoro methoxy)phenyl]-5H-[1,3]thiazolo[3,2-a]pyrimidin-5-one The title compound was prepared by condensation of Intermediate 15 (350 mg, 1.072 mmol) with 2-cyclohexylmethoxy-3-methoxybenzaldehyde (372 mg, 1.501 mmol) in presence of sodium ethoxide (146 mg, 2.147 mmol) in ethanol (15 ml) according to the procedure outlined in Example 24 to give 281 mg of the desired product as a pale yellow solid; ¹H NMR (300 MHz, DMSO-d₆) δ 1.03-1.10 (m, 2H), 1.18-1.25 (m, 3H), 1.68-1.79 (m, 6H), 3.60-3.68 (m, 2H), 3.77 (s, 3H), 6.81-6.88 (m, 2H), 6.91-6.96 (m, 3H), 7.40-7.46 (m, 5H), 7.98 (d, J=6.3 Hz, 1H), 8.14 (d, J=15.0 Hz, 1H); ESI-MS (m/z) 557.44 (M+H)⁺.

Example 72

7-[(E)-2-(2-Cyclohexyloxy-3-methoxyphenyl)-1-ethenyl]-6-[4-(trifluoro methoxy)phenyl]-5H-[1,3]thiazolo[3,2-a]pyrimidin-5-one The title compound was synthesized by condensation of Intermediate 15 (350 mg, 1.072 mmol) with (2-cyclohexyloxy-3-methoxy)benzaldehyde (351 mg, 1.501 mmol) in presence of sodium ethoxide (146 mg, 2.147 mmol) in ethanol (15 ml) according to the procedure outlined in Example 24 to give 251 mg of the desired product as a pale yellow solid; ¹H NMR (300 MHz, DMSO-d₆) δ 1.15-1.21 (m, 4H), 1.33-1.49 (m, 2H), 1.68-1.79 (m, 2H), 1.76-1.83 (m, 2H), 3.74 (s, 3H), 3.95-4.05 (m, 1H), 6.87 (d, J=6.3 Hz, 2H), 6.97 (d, J=7.2 Hz, 4H), 7.40-7.46 (m, 2H), 7.50 (d, J=6.3 Hz, 1H), 7.99 (d, J=6.3 Hz, 1H), 8.08 (d, J=15.6 Hz, 1H); ESI-MS (m/z) 543.57 (M+H)⁺.

Example 73

7-[(E)-2-{3-Methoxy-2-(2-methoxyethoxy)phenyl}-1-ethenyl]-6-[4-(trifluoro methoxy)-phenyl]-5H-[1,3]thiazolo[3,2-a]pyrimidin-5-one The title compound was synthesized by condensation of Intermediate 15 (350 mg, 1.072 mmol) with 3-methoxy-2-(2-methoxyethoxy)benzaldehyde (316 mg, 1.501 mmol) in presence of sodium ethoxide (146 mg, 2.147 mmol) in ethanol (15 ml) according to the procedure of Example 24 to give 286 mg of the desired product as a pale yellow solid; ¹H NMR (300 MHz, DMSO-d₆) δ 3.33-3.40 (m, 3H), 3.45-3.51 (m, 2H), 3.78 (s, 3H), 3.95-4.03 (m, 2H), 6.82 (d, J=15.6 Hz, 1H), 6.85-6.91 (m, 1H), 7.00 (d, J=4.2 Hz, 2H), 7.45-7.52 (m, 5H), 8.00 (d, J=4.8 Hz, 1H), 8.19 (d, J=15.6 Hz, 1H); ESI-MS (m/z) 518.19 (M+H)⁺.

Example 74

7-[(E)-2-{(3-Cyanopropoxy)-3-methoxy}phenylvinyl]-6-[4-(trifluoromethoxy)phenyl]-5H-[1,3]thiazolo[3,2-a]pyrimidin-5-one The title compound was synthesized by condensation of Intermediate 15 (350 mg, 1.012 mmol) with 2-(3-cyanopropoxy)-3-methoxy-benzaldehyde (329 mg, 1.501 mmol) in presence of sodium ethoxide (145 mg, 2.145 mmol) according to the procedure outlined in Example 24 to give 250 mg of the desired product as a pale yellow solid; ¹H NMR (300 MHz, DMSO-d₆) δ 1.82-1.87 (m, 2H), 2.67 (t, J=7.2 Hz, 2H), 3.89 (t, J=6.9 Hz, 1H), 6.86-6.91 (m, 2H), 7.02 (s, 2H), 7.46 (s, 4H), 7.52 (d, J=4.8 Hz, 2H), 7.99-8.03 (m, 2H); ESI-MS (m/z) 528.48 (M+H)⁺.

Example 75

7-[(E)-2-(2-Cyclopropylmethoxy-3-methoxyphenyl)-1-ethenyl]-2-methyl-6-[4-(tri fluoromethoxy)phenyl]-5H-[1,3]thiazolo[3,2-a]pyrimidin-5-one

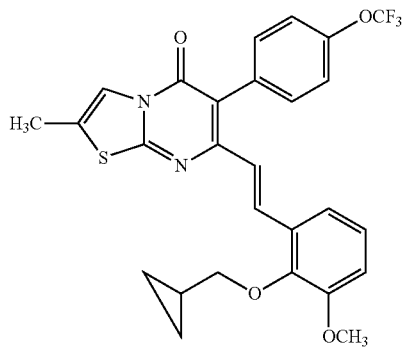

The title compound was prepared from Intermediate 16 (100 mg, 0.202 mmol) and 4-trifluoromethoxyphenylboronic acid (58 mg, 0.283 mmol) using Pd[(C₆H₅)₃P]₄ (90 mg, 0.008 mmol) and sodium carbonate (128 mg, 1.213 mmol) in toluene (10 ml) and ethanol (5 ml) and water (4 ml) according to the procedure outlined in Example 1 to afford crude residue which was purified by column chromatography to afford 60 mg of the desired product; ¹H NMR (300 MHz, DMSO-d₆) δ 0.22-0.27 (m, 2H), 0.46-0.52 (m, 3H), 0.98-1.01 (m, 1H), 2.44 (s, 3H), 3.67 (d, J=6.9 Hz, 2H), 3.76 (s, 3H), 6.86-6.92 (m, 2H), 6.99-7.00 (m, 2H), 7.45 (m, 1H), 7.84 (s, 1H), 8.12 (d, J=15.6 Hz, 1H); ESI-MS (m/z) 529.23 (M+H)⁺.

Example 76

7-[(E)-2-(2-Cyclopropylmethoxy-3-methoxyphenyl)-1-ethenyl]-3-methyl-6-[4-(tri fluoromethoxy)phenyl]-5H-[1,3]thiazolo[3,2-a]pyrimidin-5-one

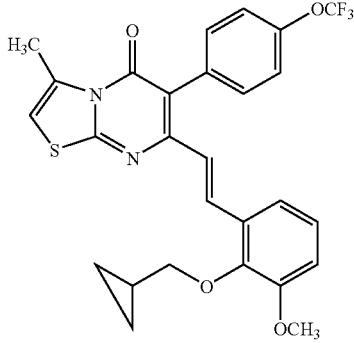

The title compound was prepared from Intermediate 17 (100 mg, 0.202 mmol) and 4-trifluoromethoxyphenylboronic acid (58 mg, 0.283 mmol) using Pd[(C₆H₅)₃P]₄ (90 mg, 0.008 mmol) and sodium carbonate (128 mg, 1.213 mmol) in toluene (10 ml) and ethanol (5 ml) and water (4 ml) according to the procedure outlined in Example 1 to afford crude residue which was purified by column chromatography using 10% ethyl acetate in petroleum ether to afford 50 mg of the desired product; $^1$H NMR (300 MHz, DMSO-d$_6$) δ 0.24-0.26 (m, 2H), 0.48-0.50 (m, 2H), 0.90-1.10 (m, 1H), 2.65 (s, 3H), 3.67 (d, J=6.9 Hz, 2H), 3.76 (s, 3H), 6.83 (d, J=15.6 Hz, 2H), 6.90-6.91 (m, 2H), 6.98-7.01 (m, 4H), 7.43 (s, 4H), 8.10 (d, J=15.6 Hz, 1H); ESI-MS (m/z) 529.19 (M+H)$^+$.

Example 77

7-[(E)-2-(2-Cyclopropylmethoxy-3-methoxyphenyl)-1-ethenyl]-2,3-dimethyl-6-[4-(trifluoromethoxy) phenyl]-5H-[1,3]thiazolo[3,2-a]pyrimidin-5-one

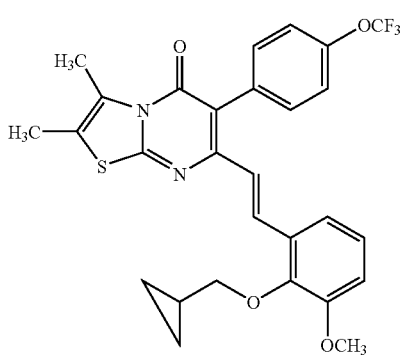

The title compound was prepared from Intermediate 18 (100 mg, 0.196 mmol) and 4-trifluoromethoxyphenylboronic acid (56 mg, 0.275 mmol) using Pd[(C$_6$H$_5$)$_3$P]$_4$ (90 mg, 0.009 mmol) and sodium carbonate (125 mg, 1.187 mmol) in toluene (10 ml) and ethanol (5 ml) and water (4 ml) according to the procedure outlined in Example 1 to afford crude residue which was purified by column chromatography using 10% ethyl acetate in petroleum ether to afford 80 mg of the desired product; $^1$H NMR (300 MHz, DMSO-d$_6$) δ 0.25-0.28 (m, 2H), 0.46-0.52 (m, 2H), 0.90-1.01 (m, 1H), 2.30 (s, 3H), 2.59 (s, 3H), 3.67 (d, J=7.5 Hz, 2H), 3.76 (s, 3H), 6.82 (d, J=15.6 Hz, 2H), 6.88-6.91 (m, 1H), 6.98-7.00 (m, 4H), 7.43 (s, 4H), 8.08 (d, J=15.6 Hz, 1H); ESI-MS (m/z) 543.19 (M+H)$^+$.

Example 78

2-Chloro-7-[(E)-2-(2-(2,2-dimethylpropoxy)-3-methoxyphenyl)vinyl]-6-[4-(tri fluoromethoxy)phenyl]-5H-[1,3]thiazolo[3,2-a]pyrimidin-5-one

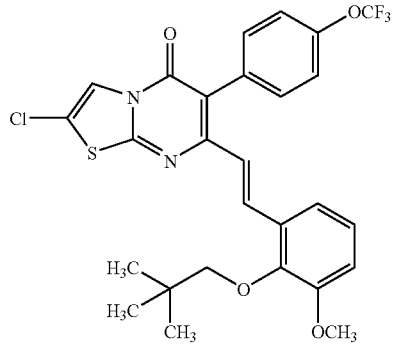

The title compound was prepared from Intermediate 19 (65 mg, 0.122 mmol) and 4-trifluoromethoxyphenyl boronic acid (27 mg, 0.132 mmol) using Pd[(C$_6$H$_5$)$_3$P]$_4$ (5 mg, 0.004 mmol) in toluene (10 ml) and ethanol (5 ml) followed by sodium carbonate (77 mg, 0.734 mmol) in water (5 ml) according to the procedure outlined in Example 1 to afford 75 mg of the desired compound; $^1$H NMR (300 MHz, DMSO-d$_6$) δ 0.99 (s, 9H), 3.50 (s, 2H), 3.76 (s, 3H), 6.81 (d, J=16.2 Hz, 1H), 6.88-6.94 (m, 1H), 6.99 (d, J=4.2 Hz, 2H), 7.42-7.48 (m, 4H), 8.18 (d, J=15.6 Hz, 1H), 8.26 (s, 1H); ESI-MS (m/z) 565.55, 567 (M+H)$^+$.

Example 79

2-Chloro-6-[4-(dimethylamino)phenyl]-7-[(E)-2-(2-(2,2-dimethylpropoxy)-3-methoxy-phenyl)vinyl]-5H-[1,3]thiazolo[3,2-a]pyrimidin-5-one

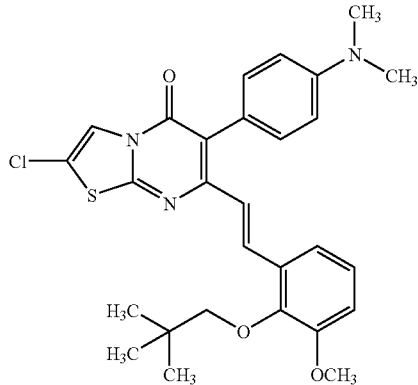

The title compound was prepared from Intermediate 19 (100 mg, 0.181 mmol) and 4-N,N-dimethylaminophenyl boronic acid (34 mg, 0.210 mmol) using Pd[(C$_6$H$_5$)$_3$P]$_4$ (8 mg, 0.007 mmol) in toluene (5 ml) and ethanol (2 ml) followed by sodium carbonate (119 mg, 1.110 mmol) in water (2 ml) according to the procedure outlined in Example 1 to afford 120 mg of the desired compound; $^1$H NMR (300 MHz, DMSO-d$_6$) δ 1.06 (s, 9H), 2.99 (s, 6H), 3.54 (s, 2H), 3.79 (s, 3H), 6.75 (d, J=9.0 Hz, 2H), 6.88-6.96 (m, 3H), 7.15 (d, J=8.1 Hz, 2H), 8.05 (s, 1H), 8.14 (s, 2H); ESI-MS (m/z) 524.49, 526 (M+H)$^+$.

Example 80

4-{2-Chloro-7-[(E)-2-(2-(2,2-dimethylpropoxy)-3-methoxyphenyl)vinyl]-5-oxo-5H-[1,3]thiazolo[3,2-a] pyrimidin-6-yl}benzonitrile

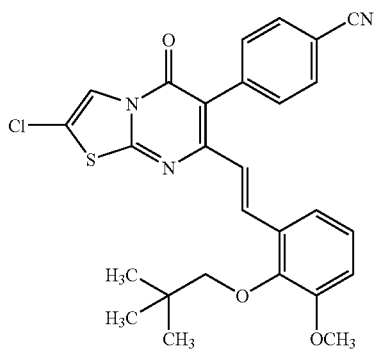

The title compound was prepared from Intermediate 19 (100 mg, 0.181 mmol) and 4-cyanophenylboronic acid (30 mg, 0.200 mmol) using Pd[(C$_6$H$_5$)$_3$P]$_4$ (9 mg, 0.007 mmol) in toluene (5 ml) and ethanol (2 ml) followed by sodium carbonate (119 mg, 1.110 mmol) in water (2 ml) according to the procedure outlined in Example 1 to afford 137 mg of the desired compound; $^1$H NMR (300 MHz, DMSO-d$_6$) δ 1.01 (s, 9H), 3.52 (s, 2H), 3.76 (s, 3H), 6.75 (d, J=15.6 Hz, 1H), 6.96-7.02 (m, 3H), 7.53 (d, J=8.4 Hz, 2H), 7.93 (d, J=8.4 Hz, 2H), 8.22 (d, J=15.6 Hz, 1H), 8.28 (s, 1H); ESI-MS (m/z) 506.55, 508 (M+H)$^+$.

Example 81

2-Chloro-6-[4-(dimethylamino)phenyl]-7-[(E)-2-(2-isobutoxy-3-methoxyphenyl)vinyl]-5H-[1,3]thiazolo[3,2-a]pyrimidin-5-one

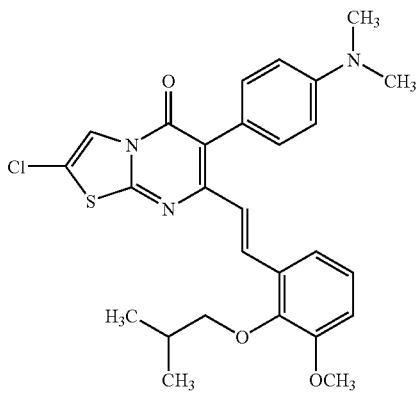

The title compound was prepared by the coupling reaction of Intermediate 20 (150 mg, 2.912 mmol), 4-N,N-dimethylaminophenylboronic acid (52 mg, 3.142 mmol), Pd[(C$_6$H$_5$)$_3$P]$_4$ (13 mg, 0.001 mmol) and sodium carbonate (193 mg, 1.820 mmol) in a mixture of toluene (10 ml), ethanol (3 ml) and water (3 ml) according to the procedure described in Example 1 to afford 210 mg of the desired compound; $^1$H NMR (300 MHz, DMSO-d$_6$) δ 1.06 (d, J=6.3 Hz, 6H), 2.06 (br s, 1H), 3.00 (s, 6H), 3.69 (d, J=6.9 Hz, 2H), 3.82 (s, 3H), 6.78-6.84 (m, 3H), 6.90-7.08 (m, 4H), 7.20-7.26 (m, 1H), 7.80 (s, 1H), 8.19 (d, J=16.2 Hz, 1H); ESI-MS (m/z) 510.76, 512 (M+H)$^+$.

Example 82

4-{7-[(E)-2-(3-Methoxy-2-neopentyloxyphenyl)-1-ethenyl]-5-oxo-3-(trifluoro methyl)-5H-[1,3]thiazolo[3,2-a]pyrimidin-6-yl}benzonitrile

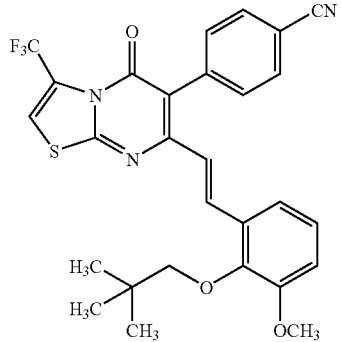

This compound was prepared from Intermediate 21 (100 mg, 0.197 mmol) and 4-cyanophenylboronic acid (35 mg, 0.204 mmol) using Pd[(C$_6$H$_5$)$_3$P]$_4$ (8 mg, 0.007 mmol) and sodium carbonate (112 mg, 1.053 mmol) in toluene (10 ml) and ethanol (5 ml) and water (4 ml) according to the procedure outlined in Example 1 to afford crude residue which was purified by column chromatography using 1% ethyl acetate in chloroform to afford 70 mg of the desired product; $^1$H NMR (300 MHz, DMSO-d$_6$) δ 1.03 (s, 9H), 3.53 (m, 2H), 3.77 (m, 2H), 6.72-6.77 (m, 1H), 6.98-7.02 (m, 2H), 7.52-7.55 (m, 2H), 7.91-7.94 (m, 2H), 8.24 (s, 1H), 8.30 (s, 2H); ESI-MS (m/z) 540.53 (M+H)$^+$.

Examples 83-90, outlined in Table 5, were prepared from Intermediate 22 and the appropriate aldehydes using procedure similar to that for Example 24

TABLE 5

Structural details of Examples 83-90

| Example | $R^{a1}$ | Mol. Formula |
|---|---|---|
| Example 83 | CH$_2$CH$_2$CH$_2$CN | C$_{30}$H$_{22}$N$_4$O$_3$S |
| Example 84 | CH$_2$CH$_2$OCH$_3$ | C$_{29}$H$_{23}$N$_3$O$_4$S |
| Example 85 | CH$_2$CH$_2$OCH$_2$CH$_3$ | C$_{30}$H$_{25}$N$_3$O$_4$S |
| Example 86 | cyclopropylmethyl | C$_{30}$H$_{23}$N$_3$O$_3$S |
| Example 87 | CH$_2$CH$_2$CH$_2$CH$_3$ | C$_{30}$H$_{25}$N$_3$O$_3$S |
| Example 88 | CH$_2$CH$_2$CH(CH$_3$)$_2$ | C$_{31}$H$_{27}$N$_3$O$_3$S |
| Example 89 | cyclobutylmethyl | C$_{31}$H$_{25}$N$_3$O$_3$S |
| Example 90 | pyridin-2-ylmethyl | C$_{32}$H$_{22}$N$_4$O$_3$S |

Example 83

4-(2-{(E)-2-[2-(3-Cyanopropoxy)-3-methoxyphenyl}-1-ethenyl}-4-oxo-4H-benzo[4,5]-[1,3]thiazolo-[3,2]pyrimidin-3-yl)benzonitrile The title compound was prepared by condensation of Intermediate 22 (350 mg, 1.102 mmol) with 4-(2-formyl-6-methoxyphenoxy)butanenitrile (338 mg, 1.543 mmol) in presence of sodium ethoxide (150 mg, 2.203 mmol) in ethanol (15 ml) according to the procedure outlined in Example 24 to give 281 mg of the desired product as a pale yellow solid; $^1$H NMR (300 MHz, DMSO-d$_6$) δ 1.88 (t, J=7.2 Hz, 2H), 2.71 (t, J=7.2 Hz, 2H), 3.79 (s, 3H), 3.93 (t, J=7.5 Hz, 2H), 6.84 (d, J=15.3

Hz, 1H), 6.98-7.06 (m, 3H), 7.55-7.61 (m, 4H), 7.96 (d, J=8.4 Hz, 2H), 8.06-8.12 (m, 2H), 8.80-8.89 (m, 1H); ESI-MS (m/z) 519.24 (M+H)+.

Example 84

4-(2-{(E)-2-[3-Methoxy-2-(methoxyethoxy)phenyl}-1-ethenyl]-4-oxo-4H-benzo[4,5]-[1,3]thiazolo-[3,2] pyrimidin-3-yl)benzonitrile The title compound was synthesized by condensation of Intermediate 22 (340 mg, 1.072 mmol) with 3-methoxy-[2-(2-methoxyethoxy)]benzaldehyde (315 mg, 1.501 mmol) in presence of sodium ethoxide (146 mg, 2.147 mmol) in ethanol (15 ml) according to the procedure outlined in Example 24 to give 261 mg of the desired product as a pale yellow solid; $^1$H NMR (300 MHz, DMSO-$d_6$) δ 3.37 (s, 3H), 3.51 (s, 2H), 3.78 (s, 3H), 4.04 (s, 2H), 6.78 (d, J=15.6 Hz, 1H), 6.97-7.03 (m, 3H), 7.57-7.61 (m, 4H), 7.95 (d, J=8.4 Hz, 2H), 8.02-8.08 (m, 1H), 8.27 (d, J=15.6 Hz, 1H), 8.43-8.49 (m, 1H); ESI-MS (m/z) 510.47 (M+H)+.

Example 85

4-{2-[(E)-2-[2-(2-Ethoxyethoxy)-3-methoxy]phenyl}-1-ethenyl]-4-oxo-4H-benzo[4,5]-[1,3]thiazolo-[3,2]pyrimidin-3-yl)benzonitrile The title compound was prepared by condensation of Intermediate 22 (400 mg, 1.262 mmol with 2-(2-ethoxyethoxy)-3-methoxy)benzaldehyde (395 mg, 1.762 mmol) in presence of sodium ethoxide (171 mg, 2.527 mmol) in ethanol (15 ml) according to the procedure outlined in Example 24 to give 310 mg of the desired product as a pale yellow solid; $^1$H NMR (300 MHz, DMSO-$d_6$) δ 1.20 (t, J=6.9 Hz, 3H), 3.50-3.56 (m, 4H), 3.78 (s, 3H), 4.04-4.10 (m, 2H), 6.76 (d, J=15.6 Hz, 1H), 6.95-7.01 (m, 3H), 7.54-7.61 (m, 4H), 7.95 (d, J=8.4 Hz, 2H), 8.04-8.10 (m, 1H), 8.23 (d, J=15.6 Hz, 1H), 8.80-8.90 (m, 1H); ESI-MS (m/z) 523.67 (M+H)+.

Example 86

4-{2-[(E)-2-[2-Cyclopropylmethoxy-3-methoxy] phenyl}-1-ethenyl]-4-oxo-4H-benzo[4,5]-[1,3]thiazolo-[3,2]pyrimidin-3-yl)benzonitrile The title compound was synthesized by condensation of Intermediate 22 (350 mg, 1.102 mmol) with 2-cyclopropylmethoxy-3-methoxybenzaldehyde (341 mg, 1.653 mmol) in presence of sodium ethoxide (150 mg, 2.047 mmol) in ethanol (15 ml) according to the procedure outlined in Example 24 to give 251 mg of the desired product as a pale yellow solid; $^1$H NMR (300 MHz, DMSO-$d_6$) δ 0.25-0.33 (m, 2H), 0.50-0.54 (m, 2H), 1.10-1.20 (m, 1H), 3.71 (d, J=3.6 Hz, 2H), 3.77 (s, 3H), 6.83 (d, J=15.6 Hz, 1H), 6.95-7.09 (m, 3H), 7.53-7.60 (m, 4H), 7.90-7.99 (m, 2H), 8.02-8.08 (m, 1H), 8.22 (d, J=15.6 Hz, 1H), 8.80-8.90 (m, 1H); ESI-MS (m/z) 506.27 (M+H)+.

Example 87

4-{2-[(E)-2-[2-Butoxy-3-methoxy]phenyl}-1-ethenyl]-4-oxo-4H-benzo[4,5]-[1,3]thiazolo-[3,2]pyrimidin-3-yl)benzonitrile The title compound was synthesized by condensation of Intermediate 22 (250 mg, 0.783 mmol) with (2-butoxy-3-methoxy)benzaldehyde (229 mg, 1.104 mmol) in presence of sodium ethoxide (107 mg, 1.572 mmol) in ethanol (15 ml) according to the procedure outlined in Example 24 to give 251 mg of the desired product as a pale yellow solid; $^1$H NMR (300 MHz, DMSO-$d_6$) δ 0.98-1.04 (m, 3H), 1.53 (s, 4H), 3.77 (s, 3H), 3.85 (s, 2H), 6.88 (d, J=15.6 Hz, 1H), 6.95-7.09 (m, 2H), 7.54-7.61 (m, 5H), 7.96 (d, J=8.4 Hz, 2H), 8.02-8.09 (m, 1H), 8.15 (d, J=15.6 Hz, 1H), 8.82-8.88 (m, 1H); ESI-MS (m/z) 508.31 (M+H)+.

Example 88

4-{2-[(E)-2-[2-(3-Methylbutoxy-3-methoxy]phenyl}-1-ethenyl]-4-oxo-4H-benzo[4,5]-[1,3]thiazolo-[3,2]pyrimidin-3-yl)benzonitrile The title compound was synthesized by condensation of Intermediate 22 (250 mg, 0.781 mmol) with 2-(3-Methylbutoxy-3-methoxy)benzaldehyde (215 mg, 1.102 mmol) in presence of sodium ethoxide (107 mg, 1.572 mmol) in ethanol (15 ml) according to the procedure outlined in Example 24 to give 212 mg of the desired product as a pale yellow solid; $^1$H NMR (300 MHz, DMSO-$d_6$) δ 0.98 (d, J=6.9 Hz, 6H), 1.46 (q, J=6.3 Hz, 2H), 3.15 (d, J=5.4 Hz, 1H), 3.78 (s, 3H), 3.88 (t, J=6.3 Hz, 2H), 6.87 (d, J=15.6 Hz, 1H), 6.95-7.09 (m, 3H), 7.53-7.60 (m, 4H), 7.95 (d, J=8.4 Hz, 2H), 8.04-8.10 (m, 1H), 8.14 (d, J=15.6 Hz, 1H), 8.80-8.90 (m, 1H); ESI-MS (m/z) 522.29 (M+H)+.

Example 89

4-{2-[(E)-2-[2-Cyclobutylmethoxy-3-methoxy]phenyl}-1-ethenyl]-4-oxo-4H-benzo[4,5]-[1,3]thiazolo-[3,2]pyrimidin-3-yl)benzonitrile The title compound was synthesized by condensation of Intermediate 22 (250 mg, 0.781 mmol) with 2-(Cyclobutylmethoxy-3-methoxy)benzaldehyde (243 mg, 1.101 mmol) in presence of sodium ethoxide (107 mg, 1.571 mmol) in ethanol (15 ml) according to the procedure outlined in Example 24 to give 227 mg of the desired product as a pale yellow solid; $^1$H NMR (300 MHz, DMSO-$d_6$) δ 1.85-1.92 (m, 5H), 1.98-2.11 (m, 2H), 3.78 (s, 3H), 3.85 (d, J=6.0 Hz, 2H) 6.84 (d, J=15.6 Hz, 1H), 6.98-7.05 (m, 3H), 7.56-7.62 (m, 4H), 7.96 (d, J=7.8 Hz, 2H), 8.03-8.09 (m, 1H), 8.20 (d, J=15.6 Hz, 1H), 8.80-8.89 (m, 1H); ESI-MS (m/z) 520.28 (M+H)+.

Example 90

4-{2-[(E)-2-[3-Methoxy-2-pyridin-2-ylmethoxy] phenyl}-1-ethenyl]-4-oxo-4H-benzo[4,5]-[1,3]thiazolo-[3,2]pyrimidin-3-yl)benzonitrile The title compound was synthesized by condensation of Intermediate 22 (350 mg, 1.102 mmol) with 3-Methoxy-2-(pyridin-2-ylmethoxy)benzaldehyde (376 mg, 1.541 mmol) in presence of sodium ethoxide (150 mg, 2.201 mmol) in ethanol (15 ml) according to the procedure outlined in Example 24 to give 296 mg of the desired product as a pale yellow solid; $^1$H NMR (300 MHz, DMSO-$d_6$) δ 3.82 (s, 3H), 5.01 (s, 2H), 6.77 (d, J=15.6 Hz, 1H), 6.98-7.06 (m, 3H), 7.36 (t, J=5.4 Hz, 1H), 7.54-7.62 (m, 5H), 7.88 (d, J=8.1 Hz, 3H), 8.00-8.08 (m, 1H), 8.13 (d, J=15.6 Hz, 1H), 8.56 (d, J=3.9 Hz, 1H), 8.80-8.86 (m, 1H); ESI-MS (m/z) 543.28 (M+H)+.

Examples 91-94, outlined in Table 6, were prepared from Intermediate 23 and the appropriate aldehydes using procedure similar to that for Example 24

TABLE 6

Structural details of Examples 91-94

| Example | R$^{a1}$ | Mol. Formula |
|---------|----------|--------------|
| Example 91 | (cyclopropylmethyl) | C$_{30}$H$_{23}$F$_3$N$_2$O$_3$S |
| Example 92 | CH$_2$CH$_2$OCH$_3$ | C$_{29}$H$_{23}$F$_3$N$_2$O$_4$S |
| Example 93 | CH$_2$CH$_2$OCH$_2$CH$_3$ | C$_{30}$H$_{25}$F$_3$N$_2$O$_4$S |
| Example 94 | CH$_2$CH$_2$CH$_2$CN | C$_{30}$H$_{22}$F$_3$N$_3$O$_3$S |

Example 91

2-{(E)-2-[(2-Cyclopropylmethoxy)-3-methoxyphenyl]-1-ethenyl}-3-(4-trifluoro methyl-phenyl)-4H-benzo[4,5][1,3]thiazolo-[3,2-a]pyrimidin-4-one The title compound was synthesized by condensation of Intermediate 23 (250 mg, 0.690 mmol) with 2-Cyclopropylmethoxy-3-methoxybenzaldehyde (200 mg, 0.970 mmol) in presence of sodium ethoxide (94 mg, 1.380 mmol) in ethanol (15 ml) according to the procedure outlined in Example 24 to give 160 mg of the desired product as a pale yellow solid; $^1$H NMR (300 MHz, DMSO-d$_6$) δ 0.28-0.30 (m, 2H), 0.51-0.53 (m, 2H), 0.90-1.01 (m, 1H), 3.69 (d, J=7.5 Hz, 2H), 3.77 (s, 3H), 6.92 (d, J=15.6 Hz, 2H), 6.98-7.00 (m, 2H), 7.56-7.64 (m, 4H), 7.84-7.86 (m, 2H), 8.06-8.08 (m, 1H), 8.22 (d, J=15.6 Hz, 1H), 8.84-8.86 (m, 1H); ESI-MS (m/z) 549.36 (M+H)$^+$.

Example 92

2-{(E)-2-[(2-Methoxyethoxy)-3-methoxyphenyl]-1-ethenyl}-3-(4-trifluoro methylphenyl)-4H-benzo[4,5][1,3]thiazolo-[3,2-a]pyrimidin-4-one The title compound was synthesized by condensation of Intermediate 23 (250 mg, 0.690 mmol) with 2-(2-methoxyethoxy)-3-methoxybenzaldehyde (218 mg, 0.970 mmol) in presence of sodium ethoxide (94 mg, 1.380 mmol) in ethanol (15 ml) according to the procedure outlined in Example 24 to give 178 mg of the desired product as a pale yellow solid; $^1$H NMR (300 MHz, DMSO-d$_6$) δ 3.37 (s, 3H), 3.50 (br s, 2H), 3.78 (s, 3H), 4.04 (br s, 2H), 6.82 (d, J=15.6 Hz, 1H), 6.94-6.95 (m, 1H), 7.00-7.02 (m, 2H), 7.55-7.57 (m, 2H), 7.62-7.64 (m, 2H), 7.84-7.86 (m, 2H), 8.05-8.07 (m, 1H), 8.27 (d, J=15.6 Hz, 1H), 8.85-8.87 (m, 1H); ESI-MS (m/z) 553.81 (M+H)$^+$.

Example 93

2-{(E)-2-[(2-Ethoxyethoxy)-3-methoxyphenyl]-1-ethenyl}-3-(4-trifluoromethyl-phenyl)-4H-benzo[4,5][1,3]thiazolo-[3,2-a]pyrimidin-4-one The title compound was synthesized by condensation of Intermediate 23 (250 mg, 0.690 mmol) with 2-(2-ethoxyethoxy)-3-methoxybenzaldehyde (204 mg, 0.970 mmol) in presence of sodium ethoxide (94 mg, 1.380 mmol) in ethanol (15 ml) according to the procedure outlined in Example 24 to give 178 mg of the desired product as a pale yellow solid; $^1$H NMR (300 MHz, DMSO-d$_6$) δ 1.91 (t, J=6.9 Hz, 3H), 3.48-3.55 (m, 4H), 3.78 (s, 3H), 4.06 (br s, 2H), 6.81 (d, J=15.6 Hz, 1H), 6.92-6.94 (m, 1H), 7.00-7.02 (m, 1H), 7.55-7.57 (m, 2H), 7.61-7.64 (m, 2H), 7.84-7.87 (m, 2H), 8.07-8.09 (m, 1H), 8.23 (d, J=15.6 Hz, 1H), 8.84-8.87 (m, 1H); ESI-MS (m/z) 567.21 (M+H)$^+$.

Example 94

2-{(E)-2-[(3-Cyanopropoxy-3-methoxy)phenyl]-1-ethenyl}-3-(4-trifluoro methyl-phenyl)-4H-benzo[4,5][1,3]thiazolo-[3,2-a]pyrimidin-4-one The title compound was synthesized by condensation of Intermediate 23 (250 mg, 0.690 mmol) with 2-(3-Cyanopropoxy)-3-methoxybenzaldehyde (213 mg, 0.970 mmol) in presence of sodium ethoxide (94 mg, 1.380 mmol) in ethanol (15 ml) according to the procedure outlined in Example 24 to give 168 mg of the desired product as a pale yellow solid; $^1$H NMR (300 MHz, DMSO-d$_6$) δ 1.81-1.85 (m, 2H), 2.65-2.70 (m, 2H), 3.79 (s, 3H), 3.89-3.90 (m, 2H), 6.90 (d, J=16.2 Hz, 1H), 6.99-7.03 (m, 3H), 7.55-7.64 (m, 4H), 7.85-7.88 (m, 2H), 8.04-8.09 (m, 2H), 8.84-8.86 (m, 1H); ESI-MS (m/z) 562.36 (M+H)$^+$.

Example 95

2-{(E)-2-2-Cyclopropylmethoxy-3-methoxy phenyl]-1-ethenyl}-3-(4-trifluoro methoxy-phenyl)-4H-benzo[4,5][1,3]thiazolo-[3,2-a]pyrimidin-4-one

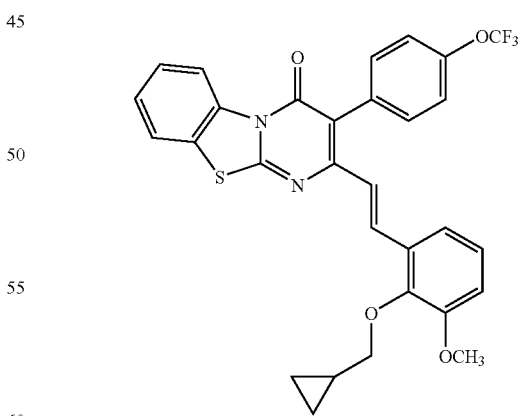

The title compound was synthesized by condensation of Intermediate 24 (300 mg, 0.796 mmol) with (2-cyclopropylmethoxy-3-methoxy)benzaldehyde (230 mg, 1.115 mmol) in presence of sodium ethoxide (108 mg, 1.593 mmol) according to the procedure described in Example 24 to give 210 mg of the desired product; $^1$H NMR (300 MHz, DMSO-d$_6$) δ

0.29-0.30 (m, 1H), 0.51-0.54 (m, 2H), 1.50-1.51 (m, 1H), 3.15 (s, 3H), 3.70 (d, J=6.9 Hz, 2H), 3.77 (s, 3H), 6.88-7.00 (m, 4H), 7.49-7.54 (m, 6H), 8.01-8.06 (m, 1H), 8.20 (d, J=15.6 Hz, 1H), 8.83-8.85 (m, 1H); ESI-MS (m/z) 565.25 (M+H)$^+$.

Example 96

2-{(E)-2-[3-Methoxy-2-(2-methoxyethoxy)phenyl]-1-ethenyl}-3-(4-trifluoro methoxy-phenyl)-4H-benzo[4,5][1,3]thiazolo-[3,2-a]pyrimidin-4-one

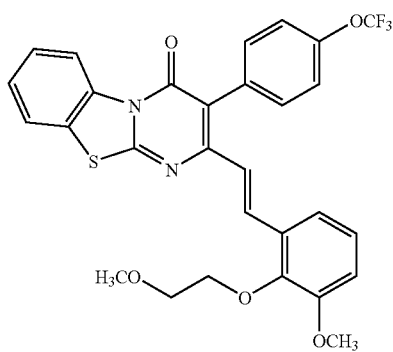

The title compound was prepared by condensation of Intermediate 24 (250 mg, 0.663 mmol) with 2-(2 methoxyethoxy)-3-methoxy)benzaldehyde (195 mg, 0.929 mmol) in presence of sodium ethoxide (90 mg, 1.327 mmol) in ethanol (10 ml) according to the procedure outlined in Example 24 to give 167 mg of the desired product; $^1$H NMR (300 MHz, DMSO-d$_6$) δ 3.37 (s, 1H), 3.51 (br s, 2H), 3.78 (s, 3H), 4.03 (br s, 2H), 6.82 (d, J=15.6 Hz, 1H), 6.91-6.93 (m, 1H), 7.00-7.02 (m, 2H), 7.49-7.54 (m, 6H), 8.05-8.06 (m, 1H), 8.25 (d, J=15.9 Hz, 1H), 8.83-8.85 (m, 1H); ESI-MS (m/z) 569.14 (M+H)$^+$.

Example 97

2-{(E)-2-[(2-Ethoxyethoxy)-3-methoxyphenyl]-1-ethenyl}-3-(4-trifluoro methoxy-phenyl)-4H-benzo[4,5][1,3]thiazolo-[3,2-a]pyrimidin-4-one

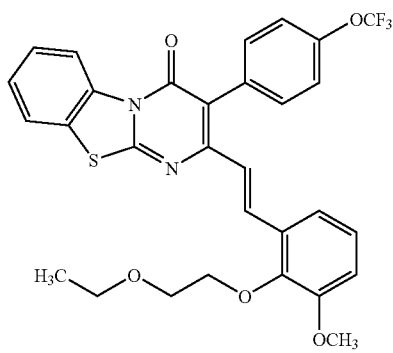

The title compound was prepared by condensation of Intermediate 24 (290 mg, 0.770 mmol) with 2-(2-ethoxyethoxy)-3-methoxy)benzaldehyde (242 mg, 1.07 mmol) in presence of sodium ethoxide (105 mg, 1.540 mmol) in ethanol (10 ml) according to the procedure outlined in Example 24 to give 225 mg of the desired product as a yellow solid; $^1$H NMR (300 MHz, DMSO-d$_6$) δ 1.91 (t, J=6.6 Hz, 3H), 3.48-3.54 (m, 4H), 3.78 (s, 3H), 4.01-4.06 (m, 2H), 6.80 (d, J=15.6 Hz, 1H), 6.90-6.92 (m, 1H), 7.00-7.01 (m, 2H), 7.4-7.55 (m, 6H), 8.05-8.06 (m, 1H), 8.20 (d, J=15.6 Hz, 1H), 8.84-8.85 (m, 1H); ESI-MS (m/z) 583.21 (M+H)$^+$.

Example 98

2-[(E)-2-(2-Cyclopropylmethoxy-3-methoxyphenyl)vinyl]-3-(4-trifluoro methoxyphenyl)-10-methylpyrimido[1,2-a]benzimidazol-4(10H)-one

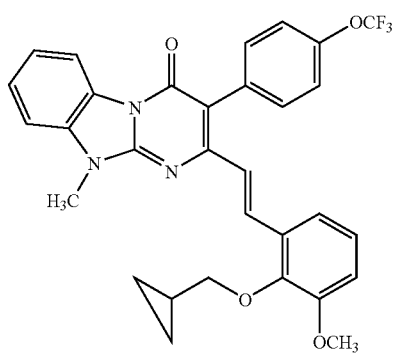

The title compound was synthesized by condensation of Intermediate 25 (300 mg, 0.801 mmol) with 2-cyclopropylmethoxy-3-methoxy benzaldehyde (215 mg, 1.010 mmol) in presence of sodium ethoxide (108 mg, 1.610 mmol) in ethanol (25 ml) according to the procedure described in Example 24 to afford crude product which was purified by column chromatography to give 416 mg of the desired compound; $^1$H NMR (300 MHz, DMSO-d$_6$) δ 0.23-0.32 (m, 2H), 0.49-0.56 (m, 2H), 1.12 (br s, 1H), 3.70-3.78 (m, 6H), 3.87 (s, 2H), 6.91-6.99 (m, 3H), 7.20-7.26 (m, 1H), 7.32-7.38 (m, 1H), 7.45-7.54 (m, 5H), 7.68 (d, J=8.4 Hz, 1H), 8.27 (d, J=16.2 Hz, 1H), 8.37-8.43 (m, 1H); APCI-MS (m/z) 562.49 (M+H)$^+$.

Pharmacological Activity

The illustrative examples of the present invention are screened for TRPV3 activity according to a modified procedure described in Tóth, A., Kedei, N., Wang, Y. and Blumberg, P. M. *Life Sciences* (2003), 73, 487-498. The screening of the compounds can be carried out by other methods and procedures known to a person skilled in the art. Such screening methods may be found in (a) Hu, H.-Z. et al. *J. Biol. Chem.* (2004), 279, 35741-35747; (b) Smith, G. D. et al. *Nature* (2002), 418, 186-190; (c) Peier, A. M. et al. *Science* (2002), 296, 2046-2049.

Screening for TRPV3 Antagonist Using the $^{45}$Calcium Uptake Assay:

The inhibition of TRPV3 receptor activation was followed as inhibition of 2-aminoethoxydiphenylborate (2-APB) induced cellular uptake of radioactive calcium. Test compounds were dissolved in dimethyl sulfoxide (DMSO) to prepare 20 mM stock solution and then diluted using plain medium with DMEM/F-12 containing 1.8 mM CaCl$_2$ to get desired concentration. Final concentration of DMSO in the reaction was 0.5% (v/v). Human TRPV3 expressing CHO cells were grown in DMEM/F-12 medium with 10% FBS, 1% penicillin-streptomycin solution, 400 µg/ml of G-418. Cells were seeded 24 h prior to the assay in 96 well plates so as to get ~50,000 cells per well on the day of experiment. Cells were treated with test compounds for 10 minutes followed by addition of 2-APB at a final concentration of 500 µM and 5 µCi/ml $^{45}Ca^{+2}$ for 4 minutes. Cells were washed and lysed using buffer containing 1% Triton X-100, 0.1% deoxycholate and 0.1% SDS. Radioactivity in the lysate was measured in Packardt Top count after addition of liquid scintillant. Concentration response curves were plotted as a % of maximal response obtained in the absence of test antagonist. $IC_{50}$ value was calculated from concentration response curve by nonlinear regression analysis using GraphPad PRISM software.

The compounds prepared were tested using the above assay procedure and the results obtained are given in Table 6. Percentage inhibition at concentrations of 1.0 µM and 10.0 µM are given in the table along with $IC_{50}$ (nM) values for selected examples.

The $IC_{50}$ (nM) values of the compounds are set forth in Table 6 wherein "A" refers to an $IC_{50}$ value of less than 250.0 nM, "B" refers to $IC_{50}$ value in range of 250.1 to 500.0 nM, "C" refers to an $IC_{50}$ value in range of 500.1 to 1000 nM and D refers to an $IC_{50}$ value in range of 1000.1 nM to 10,000 nM. Group of compounds structurally disclosed herein with $IC_{50}$ of less than 250 nM, less than 500 nM, and less than 1000 nM are separately comtemplated.

TABLE 6

In-vitro screening results of compounds of invention

| Examples | Percentage inhibition at 1.0 µM | at 10.0 µM | $IC_{50}$ |
|---|---|---|---|
| Example 1 | 6.9 | 14.4 | — |
| Example 2 | 10.45 | 73.07 | D |
| Example 3 | 20.1 | 89.3 | — |
| Example 4 | 66.5 | 84.7 | B |
| Example 5 | 60.3 | 95.1 | — |
| Example 6 | 76.0 | 95.3 | B |
| Example 7 | 12.0 | 69.3 | — |
| Example 8 | 2.0 | 20.5 | — |
| Example 9 | 71.6 | 91.9 | C |
| Example 10 | 74.8 | 92.9 | B |
| Example 11 | 76.2 | 90.0 | A |
| Example 12 | 74.7 | 94.8 | A |
| Example 13 | 91.9 | 95.4 | A |
| Example 14 | 41.0 | 88.1 | — |
| Example 15 | 73.1 | 94.8 | C |
| Example 16 | 59.3 | 91.7 | C |
| Example 17 | 73.0 | 91.1 | A |
| Example 18 | 85.0 | 94.2 | A |
| Example 19 | 74.6 | 88.4 | B |
| Example 20 | 56.5 | 79.3 | — |
| Example 21 | 14.88 | 11.60 | — |
| Example 22 | 16.1 | 24.5 | — |
| Example 23 | 15.4 | 1.2 | — |
| Example 24 | 36.3 | 67.4 | — |
| Example 25 | 70.7 | 89.9 | C |
| Example 26 | 56.6 | 84.5 | — |
| Example 27 | 69.6 | 88.0 | A |
| Example 28 | 59.7 | 85.3 | — |
| Example 29 | 86.5 | 93.7 | A |
| Example 30 | 45.2 | 75.9 | — |
| Example 31 | 66.92 | 97.15 | B |
| Example 32 | 89.3 | 97.7 | B |
| Example 33 | 85.3 | 97.4 | A |
| Example 34 | 43.1 | 78.4 | — |
| Example 35 | 29.4 | 68.5 | — |
| Example 36 | 11.2 | 0.0 | — |
| Example 37 | 39.6 | 88.1 | — |
| Example 38 | 28.6 | 50.2 | — |
| Example 39 | 4.11 | 15.21 | — |
| Example 40 | 4.6 | 31.3 | — |
| Example 41 | 75.5 | 84.5 | B |
| Example 42 | 62.7 | 78.5 | — |
| Example 43 | 63.4 | 94.0 | C |
| Example 44 | 44.0 | 88.6 | — |
| Example 45 | 30.7 | 77.5 | — |
| Example 46 | 10.0 | 52.8 | — |
| Example 47 | 43.73 | 69.25 | — |
| Example 48 | 80.0 | 95.1 | A |
| Example 49 | 41.3 | 77.3 | — |
| Example 50 | 81.9 | 89.8 | A |
| Example 51 | 89.1 | 95.6 | A |
| Example 52 | 78.4 | 90.3 | A |
| Example 53 | 89.9 | 95.9 | A |
| Example 54 | 72.8 | 95.3 | A |
| Example 55 | 81.7 | 92.8 | A |
| Example 56 | 80.9 | 93.5 | B |
| Example 57 | 79.4 | 91.9 | A |
| Example 58 | 92.8 | 95.9 | A |
| Example 59 | 3.68 | 0.00 | — |
| Example 60 | 41.32 | 81.57 | — |
| Example 61 | 22.7 | 60.6 | — |
| Example 62 | 30.6 | 55.9 | — |
| Example 63 | 81.4 | 91.8 | A |
| Example 64 | 16.3 | 21.1 | — |
| Example 65 | 15.43 | 21.96 | — |
| Example 66 | 23.40 | 34.14 | — |
| Example 67 | 80.2 | 92.2 | A |
| Example 68 | 75.8 | 83.6 | A |
| Example 69 | 51.5 | 91.5 | — |
| Example 70 | 90.81 | 97.86 | A |
| Example 71 | 61.1 | 80.8 | — |
| Example 72 | 58.1 | 82.1 | B |
| Example 73 | 79.2 | 94.9 | B |
| Example 74 | 30.20 | 86.42 | — |
| Example 75 | 86.3 | 90.4 | A |
| Example 76 | 61.9 | 79.3 | — |
| Example 77 | 24.7 | 44.0 | — |
| Example 78 | 27.1 | 47.5 | — |
| Example 79 | 57.9 | — | — |
| Example 80 | 69.1 | 87.7 | C |
| Example 81 | 64.3 | 78.5 | B |
| Example 82 | 57.4 | 70.3 | — |
| Example 83 | 23.6 | 57.1 | — |
| Example 84 | 83.8 | 93.7 | B |
| Example 85 | 81.8 | 91.9 | A |
| Example 86 | 45.5 | 75.6 | — |
| Example 87 | 34.44 | 60.79 | — |
| Example 88 | 32.87 | 51.88 | — |
| Example 89 | 26.90 | 57.53 | — |
| Example 90 | 51.24 | 81.57 | — |
| Example 91 | 4.98 | 19.85 | — |
| Example 92 | 23.11 | 47.48 | — |
| Example 93 | 6.53 | 40.18 | — |
| Example 94 | 5.84 | 10.03 | — |
| Example 95 | 10.87 | 23.74 | — |
| Example 96 | 24.8 | 67.7 | — |
| Example 97 | 20.18 | 39.34 | — |
| Example 98 | 23.04 | 29.98 | — |

The invention claimed is:
1. A compound of the formula (I):

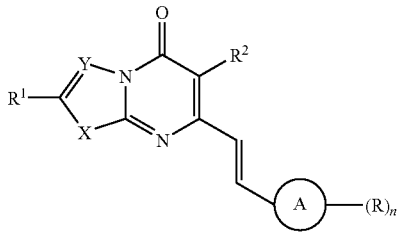

wherein X is O, S or NR$^b$;
Y is CR$^3$ or N;
ring A is phenyl or pyridine;
at each occurrence, R, which may be the same or different, is selected from hydrogen, halogen, or —OR$^a$;
R$^1$ is hydrogen, halogen or substituted or unsubstituted alkyl; R$^3$ is hydrogen, substituted or unsubstituted alkyl, or R$^1$ and R$^3$ together with the carbon atoms to which they were attached may form a fused phenyl ring;
R$^2$ is phenyl or pyridine, each of which may be optionally mono- or polysubstituted with substituent(s) independently selected from the group consisting of halogen, hydroxyl, nitro, cyano, —COOH, —NR$^4$R$^5$, acyl, substituted or unsubstituted alkyl, alkenyl, alkoxy, cyanoalkoxy, haloalkyl, haloalkyloxy, cycloalkyl, cycloalkylalkyl, cycloalkylalkoxy, aryl, heterocyclic group or heteroaryl;
at each occurrence, R$^a$, which may be the same or different, is selected from the group consisting of hydrogen, substituted or unsubstituted alkyl, haloalkyl, cyanoalkyl, alkenyl, cycloalkyl, alkoxyalkyl, aryl, heteroaryl, heterocyclic group, cycloalkylalkyl, arylalkyl, heteroarylalkyl, or heterocyclylalkyl;
at each occurrence, R$^b$ is selected from hydrogen, substituted or unsubstituted alkyl, or arylalkyl;
at each occurrence, R$^4$ and R$^5$, which may be the same or different, are independently selected from hydrogen, substituted or unsubstituted alkyl, alkenyl, cycloalkyl, cycloalkylalkyl, cycloalkenyl, aryl, arylalkyl, heteroaryl, heteroarylalkyl, heterocyclic group, or heterocyclylalkyl;
'n' is an integer ranging from 0 to 5, inclusive; and
'p' is an integer ranging from 0 to 2, inclusive;
or a pharmaceutically acceptable salt thereof.
2. The compound of claim 1 having the formula (IIa):

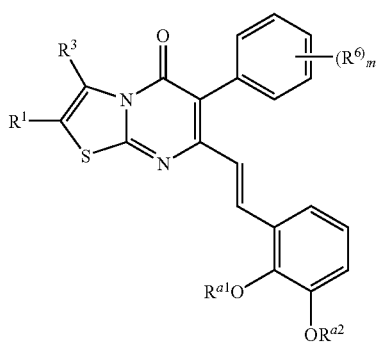

R$^1$ is hydrogen, halogen or substituted or unsubstituted alkyl; R$^3$ is hydrogen, or substituted or unsubstituted alkyl, or R$^1$ and R$^3$ together with the carbon atoms to which they were attached may form a fused phenyl ring;
each of R$^{a1}$ and R$^{a2}$, which may be the same or different, is selected from hydrogen, substituted or unsubstituted alkyl, haloalkyl, cyanoalkyl, alkenyl, cycloalkyl, alkoxyalkyl, aryl, heteroaryl, heterocyclic group, cycloalkylalkyl, arylalkyl, heteroarylalkyl, or heterocyclylalkyl;
at each occurrence, R$^6$ is independently selected from halogen, hydroxyl, nitro, cyano, —COOH, —NR$^4$R$^5$, acyl, substituted or unsubstituted alkyl, alkenyl, alkoxy, cyanoalkoxy, haloalkyl, haloalkyloxy, cycloalkyl, cycloalkylalkyl, cycloalkylalkoxy, aryl, heterocyclic group, or heteroaryl;
at each occurrence, R$^4$ and R$^5$, which may be the same or different, are independently selected from hydrogen, substituted or unsubstituted alkyl, alkenyl, cycloalkyl, cycloalkylalkyl, cycloalkenyl, aryl, arylalkyl, heteroaryl, heteroarylalkyl, heterocyclic group, or heterocyclylalkyl;
at each occurrence, R$^b$ is selected from hydrogen, substituted or unsubstituted alkyl, or arylalkyl;
'm' is an integer ranging from 0 to 3, inclusive; and
'p' is an integer ranging from 0 to 2, inclusive;
or a pharmaceutically acceptable salt thereof.
3. The compound of claim 1 having the formula (IIb):

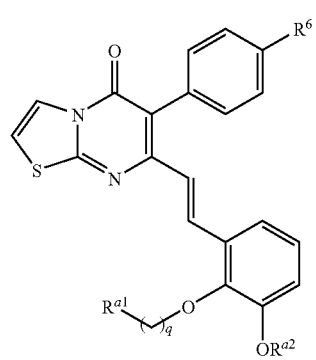

at each occurrence, R$^6$ is independently selected from halogen, hydroxyl, nitro, cyano, —COOH, —NR$^4$R$^5$, substituted or unsubstituted alkyl, alkoxy, haloalkyl, or haloalkyloxy;
R$^{a1}$ is selected from substituted or unsubstituted alkyl, alkoxy, or cycloalkyl;
R$^{a2}$ is selected from substituted or unsubstituted alkyl or haloalkyl; and
'q' is an integer ranging from 1 to 4, inclusive;
or a pharmaceutically acceptable salt thereof.

4. The compound of claim 1 having the formula (III):

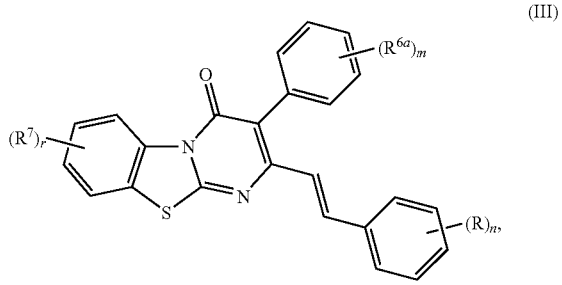

at each occurrence, R, which may be the same or different, is selected from hydrogen, halogen, or —OR$^a$;

wherein at each occurrence, R$^{6a}$, which may be the same or different, is selected independently from halogen, hydroxyl, nitro, cyano, —COOH, —NR$^4$R$^5$, acyl, substituted or unsubstituted alkyl, alkenyl, alkoxy, cyanoalkoxy, haloalkyl, haloalkyloxy, cycloalkyl, cycloalkylalkyl, cycloalkylalkoxy, aryl, heterocyclic group, or heteroaryl;

at each occurrence, R$^7$ is independently selected from halogen, nitro, cyano, substituted or unsubstituted alkyl, alkenyl, alkynyl, cycloalkyl, aryl, heteroaryl, heterocyclic group, —NR$^4$R$^5$, —S(O)$_p$NR$^4$R$^5$, or —S(O)$_p$R$^4$;

at each occurrence, R$^4$ and R$^5$, which may be the same or different, are independently selected from hydrogen, substituted or unsubstituted alkyl, alkenyl, cycloalkyl, cycloalkylalkyl, cycloalkenyl, aryl, arylalkyl, heteroaryl, heteroarylalkyl, heterocyclic group, or heterocyclylalkyl;

'n' is an integer ranging from 0 to 5, inclusive;
'p' is an integer ranging from 0 to 2, inclusive;
'm' is an integer ranging from 0 to 3; inclusive and
'r' is an integer ranging from 0 to 4;

or a pharmaceutically acceptable salt thereof.

5. The compound of claim 1, wherein R$^2$ is substituted phenyl.

6. The compound of claim 5, wherein R$^2$ is mono-para-substituted phenyl, the para-substituent being cyano, methoxy, trifluoromethyl, trifluoromethoxy, difluoromethoxy, t-butyl, or N,N-dimethylamino.

7. The compound of claim 2, wherein R$^{a1}$ is cycloalkylalkyl.

8. The compound of claim 7, wherein R$^{a1}$ cyclopropylmethyl.

9. The compound of claim 2, wherein R$^{a2}$ is alkyl.

10. The compound of claim 9, wherein R$^{a2}$ is methyl.

11. The compound of claim 1, wherein R$^2$ is halogenated phenyl or haloalkoxyphenyl.

12. The compound of claim 1, wherein R$^2$ is difluoromethoxyphenyl or trifluoromethoxyphenyl.

13. The compound of claim 1, wherein R$^2$ is substituted or unsubstituted pyridine.

14. The compound of claim 1, wherein ring A is phenyl.

15. The compound of claim 1, wherein R is halogen.

16. The compound of claim 1, wherein R is —OR$^a$.

17. The compound of claim 16, wherein R$^a$ is hydrogen.

18. The compound of claim 16, wherein R$^a$ is alkyl.

19. The compound of claim 18, wherein alkyl is methyl.

20. The compound of claim 16, wherein R$^a$ is cycloalkylalkyl.

21. The compound of claim 20, wherein cycloalkylalkyl is cyclopropylmethyl.

22. The compound of claim 1, wherein R$^3$ is hydrogen, alkyl, or haloalkyl.

23. The compound of claim 22, wherein R$^3$ is methyl.

24. The compound of claim 22, wherein R$^3$ is trifluoromethyl.

25. The compound of claim 1, wherein R$^1$ is hydrogen, halogen or methyl.

26. The compound of claim 2, wherein R$^6$ is haloalkyloxy.

27. The compound of claim 2, wherein R$^6$ is trifluoroalkoxy.

28. The compound of claim 27 wherein R$^6$ is trifluoromethoxy.

29. The compounds of claim 1 selected from
7-{(E)-2-[2-(Cyclopropylmethoxy)-3-methoxyphenyl]vinyl}-6-phenyl-5H-[1,3]thiazolo[3,2-a]pyrimidin-5-one,
6-[4-(tert-Butylphenyl)]-7-[(E)-2-(2-cyclopropylmethoxy)-3-methoxyphenyl]-1-ethenyl]-5H-[1,3]thiazolo[3,2-a]pyrimidin-5-one,
1-{4-{7-[(E)-2-(2-Cyclopropylmethoxy)-3-methoxyphenyl)-1-ethenyl]-5-oxo-5H-[1,3]thiazolo[3,2-a]pyrimidin-6-yl}phenyl}-1-ethanone,
6-(4-Dimethylaminophenyl)-7-[(E)-2-(2-cyclopropylmethoxy-3-methoxyphenyl]-1-ethenyl]-5H-[1,3]thiazolo[3,2-a]pyrimidin-5-one,
7-[(E)-2-(2-Cyclopropylmethoxy-3-methoxyphenyl)-1-ethenyl]-6-(4-hydroxyphenyl)-5H-[1,3]thiazolo[3,2-a]pyrimidin-5-one,
7-[(E)-2-(2-Cyclopropylmethoxy)-3-methoxyphenyl)-1-ethenyl]-6-(3,5-difluorophenyl)-5H-[1,3]thiazolo[3,2-a]pyrimidin-5-one, or
a pharmaceutically acceptable salt thereof.

30. 7-{(E)-2-[2-(Cyclopropylmethoxy)-3-methoxyphenyl]-1-ethenyl}-6-(4-trifluoromethoxyphenyl)-5H-[1,3]thiazolo[3,2-a]pyrimidin-5-one, or a pharmaceutically acceptable salt thereof.

31. 7-{(E)-(2-Cyclopropylmethoxy-3-hydroxy)phenyl]-ethenyl}-6-(4-trifluoro-methoxyphenyl)-5H-[1,3]thiazolo[3,2-a]pyrimidin-5-one, or a pharmaceutically acceptable salt thereof.

32. 7-{(E)-(2,3-Dihydroxy)phenyl]-1-ethenyl]-6-(4-trifluoromethoxy-phenyl)-5H-[1,3]thiazolo[3,2-a]pyrimidin-5-one, or a pharmaceutically acceptable salt thereof.

33. 7-[(E)-2-(2-Hydroxy-3-methoxyphenyl)-1-ethenyl]-6-[4-(trifluoromethoxy)phenyl]-5H-[1,3]thiazolo[3,2-a]pyrimidin-5-one, or a pharmaceutically acceptable salt thereof.

34. A pharmaceutical composition comprising one or more compounds of claim 1, and one or more pharmaceutically acceptable excipients, carriers, diluents or mixture thereof.

35. A pharmaceutical composition comprising compound of claim 30, and one or more pharmaceutically acceptable excipients, carriers, diluents or mixture thereof.

36. The compound of claim 1 selected from:
4-{7-[(E)-2-(2-Butoxy-3-methoxyphenyl)-1-ethenyl]-5-oxo-5H-[1,3]thiazolo[3,2-a]pyrimidin-6-yl}benzonitrile,
4-{7-[(E)-2-(3-Methoxy-2-pentyloxyphenyl)-1-ethenyl]-5-oxo-5H-[1,3]thiazolo[3,2-a]pyrimidin-6-yl}benzonitrile,
4-{7-[(E)-2-(3-Methoxy-2-(2-methoxyethoxy)phenyl]-1-ethenyl]-5-oxo-5H-[1,3]-thiazolo[3,2-a]pyrimidin-6-yl}benzonitrile,
4-{7-[(E)-2-(2-Ethoxyethoxy-3-methoxyphenyl)-1-ethenyl]-5-oxo-5H-[1,3]thiazolo[3,2-a]pyrimidin-6-yl}benzonitrile, 4-{7-[(E)-2-[2-(Cyclopropylmethoxy)-3-methoxyphenyl]-1-ethenyl]-5-oxo-5H-[1,3]thiazolo[3,2-a]pyrimidin-6-yl}benzonitrile, and
4-{7-[(E)-2-(2-Cyclohexylmethoxy-3-methoxy)phenyl-1-ethenyl]-5-oxo-5H-[1,3]-thiazolo[3,2-a]pyrimidin-6-yl}benzonitrile, or
a pharmaceutically acceptable salt thereof.

37. The compound of claim 1 selected from:
4-{7-[(E)-2-[2-(3-Fluorobenzyloxy)-3-methoxyphenyl-1-ethenyl]-5-oxo-5H-[1,3]-thiazolo[3,2-a]pyrimidin-6-yl}benzonitrile,
4-{7-[(E)-2-{3-Methoxy-2-(2-pyridinylmethoxy)phenyl]-1-ethenyl]}-5-oxo-5H-[1,3]-thiazolo[3,2-a]pyrimidin-6-yl}benzonitrile,
4-{7-[(E)-2-{2-(3-Cyanopropoxy)-3-(methoxyphenyl)-1-ethenyl]}-5-oxo-5H-[1,3]-thiazolo[3,2-a]pyrimidin-6-yl}benzonitrile,
7-[(E)-2-(3-Methoxy-2-propoxyphenyl)-1-ethenyl]-6-[4-(trifluoromethyl)phenyl]-5H-[1,3]thiazolo[3,2-a]pyrimidin-5-one,
7-[(E)-2-(2-Butoxy-3-methoxyphenyl)-1-etheny]-6-[4-(trifluoromethyl)phenyl]-5H-[1,3]thiazolo[3,2-a]pyrimidin-5-one, and
7-[(E)-2-(2-Isobutoxy-3-methoxyphenyl)-1-ethenyl]-6-[4-(trifluoromethyl)phenyl]-5H-[1,3]thiazolo[3,2-a]pyrimidin-5-one, or
a pharmaceutically acceptable salt thereof.

38. The compound of claim 1 selected from:
7-[(E)-2-(2-Isopentyloxy-3-methoxyphenyl)-1-ethenyl]-6-[4-(trifluoromethyl)phenyl]-5H-[1,3]thiazolo[3,2-a]pyrimidin-5-one,
3-{2-Methoxy-6-{[(E)-2-{5-oxo-6-[4-(trifluoromethyl)phenyl]-5H-[1,3]thiazolo[3,2-a]pyrimidin-7-yl}-1-ethenyl]phenoxy)propyl cyanide,
{7-[(E)-2-(2-Methoxyethoxy-3-methoxy)phenyl}vinyl]-6-[4-(trifluoromethyl)phenyl]-5H-[1,3]thiazolo[3,2-a]pyrimidin-5-one,
{7-[(E)-2-(2-Ethoxyethoxy)-3-methoxy)phenyl-1-ethenyl]-6-[4-(trifluoromethyl)phenyl]-5H-[1,3]thiazolo[3,2-a]pyrimidin-5-one,
7-[(E)-2-{3-Methoxy-2-neopentyloxyphenyl}-1-ethenyl]-6-[4-(trifluoromethoxy)-phenyl]-5H-[1,3]thiazolo[3,2-a]pyrimidin-5-one, and
7-[(E)-2-(3-Methoxy-2-neopentyloxy)phenyl-1-ethenyl]-6-(4-(trifluoromethyl)phenyl)-5H-[1,3]thiazolo[3,2-a]pyrimidin-5-one, or
a pharmaceutically acceptable salt thereof.

39. The compound of claim 1 selected from:
7-[(E)-2-{3-Methoxy-2-(2-trifluoromethylethoxy)phenyl}-1-ethenyl]-6-[4-(trifluoromethoxy)phenyl]-5H-[1,3]thiazolo[3,2-a]pyrimidin-5-one,
7-{(E)-2-[2-(Cyclopropylmethoxy)-3-methoxyphenyl]-1-ethenyl]-6-(4-trifluoromethoxy-phenyl)-5H-[1,3]thiazolo[3,2-a]pyrimidin-5-one,
7-{(E)-2-[2-(Cyclopropylmethoxy)-3-difluoromethoxyphenyl]-1-ethenyl}-6-(4-trifluoromethoxyphenyl)-5H-[1,3]thiazolo[3,2-a]pyrimidin-5-one,
7-[(E)-2-{2-Isopentyloxy-3-methoxyphenyl}-1-ethenyl]-6-[4-(trifluoromethoxy)phenyl]-5H-[1,3]thiazolo[3,2-a]pyrimidin-5-one,
4-{7-[(E)-2-(3-Methoxy-2-neopentyloxyphenyl)-1-ethenyl]-5-oxo-5H-[1,3]thiazolo[3,2-a]pyrimidin-6-yl}benzonitrile, and
7-[(E)-2-(3-Methoxy-2-pentyloxyphenyl)-1-ethenyl]-6-[4-(trifluoromethoxy)phenyl]-5H-[1,3]thiazolo[3,2-a]pyrimidin-5-one, or
a pharmaceutically acceptable salt thereof.

40. The compound of claim 1 selected from:
7-[(E)-2-(2-Isobutoxy-3-methoxyphenyl)-1-ethenyl]-6-[4-(trifluoromethoxy)phenyl]-5H-[1,3]thiazolo[3,2-a]pyrimidin-5-one,
7-[(E)-2-(2-Cyclopropylmethoxy-3-methoxyphenyl)-1-ethenyl]-2-methyl-6-[4-(trifluoro-methoxy)phenyl]-5H-[1,3]thiazolo[3,2-a]pyrimidin-5-one,
7-[(E)-2-{2-Cyclobutylmethoxy-3-methoxyphenyl}-1-ethenyl]-6-[4-(trifluoromethoxy)-phenyl]-5H-[1,3]thiazolo[3,2-a]pyrimidin-5-one,
7-[(E)-2-(2-Cyclopropylmethoxy-3-methoxyphenyl)-1-ethenyl]-6-(4-difluoromethoxy phenyl)-5H-[1,3]thiazolo[3,2-a]pyrimidin-5-one,
7-[(E)-2-(3-Methoxy-2-propoxyphenyl)-1-ethenyl]-6-[4-(trifluoromethoxy)phenyl]-5H-[1,3]thiazolo[3,2-a]pyrimidin-5-one, and
7-[(E)-2-(2-Butoxy-3-methoxyphenyl)-1-ethenyl]-6-[4-(trifluoromethoxy)phenyl]-5H-[1,3]thiazolo[3,2-a]pyrimidin-5-one, or
a pharmaceutically acceptable salt thereof.

41. The compound of claim 1 selected from:
{7-[(E)-2-(2-Cyclopropylmethoxy)-3-methoxyphenyl]-1-ethenyl]-6-[4-(trifluoromethyl)-phenyl]-5H-[1,3]thiazolo[3,2-a]pyrimidin-5-one,
4-{7-[(E)-2-(2-Isopentyloxy-3-methoxyphenyl)-1-ethenyl]-5-oxo-5H-[1,3]thiazolo[3,2-a]pyrimidin-6-yl}benzonitrile,
4-{7-[(E)-2-(2-Isobutoxy-3-methoxyphenyl)-1-ethenyl]-5-oxo-5H-[1,3]thiazolo[3,2-a]-pyrimidin-6-yl}benzonitrile,
4-{7-[(E)-2-(2-Cyclopentyloxy-3-methoxy)phenyl-1-ethenyl]-5-oxo-5H-[1,3]thiazolo-[3,2-a]pyrimidin-6-yl}benzonitrile,
4-{7-[(E)-2-(2-Cyclobutylmethoxy-3-methoxy)phenyl-1-ethenyl]-5-oxo-5H-[1,3]-thiazolo[3,2-a]pyrimidin-6-yl}benzonitrile, and
7-[(E)-2-{2-(2-Ethoxyethoxy)-3-methoxyphenyl}-1-ethenyl]-6-[4-(trifluoromethoxy)-phenyl]-5H-[1,3]thiazolo[3,2-a]pyrimidin-5-one, or
a pharmaceutically acceptable salt thereof.

42. The compound of claim 1 selected from:
7-[(E)-2-(2-Cyclobutylmethoxy-3-methoxyphenyl)-1-ethenyl]-6-[4-(trifluoromethyl)-phenyl]-5H-[1,3]thiazolo[3,2-a]pyrimidin-5-one,
7-[(E)-2-(2-Cyclopentyloxy-3-methoxyphenyl)-1-ethenyl]-6-[4-(trifluoromethyl)-phenyl]-5H-[1,3]thiazolo[3,2-a]pyrimidin-5-one,
7-[(E)-2-{3-Methoxy-2-(pyridin-2-ylmethoxy)phenylvinyl]-6-[4-(trifluoromethyl)phenyl]-5H-[1,3]thiazolo[3,2-a]pyrimidin-5-one,
7-[(E)-2-(2-Cyclopropylmethoxy-3-methoxyphenyl)-1-ethenyl]-6-[3-(trifluoromethyl)phenyl]-5H-[1,3]thiazolo[3,2-a]pyrimidin-5-one,
6-(4-Dimethylaminophenyl)-7-[(E)-2-(2-isobutoxy-3-methoxyphenyl)-1-ethenyl]-5H-[1,3]thiazolo[3,2-a]pyrimidin-5-one, and
6-(4-Dimethylaminophenyl)-7-[(E)-2-(3-methoxy-2-neopentyloxy)phenyl-1-ethenyl]-5H-[1,3]thiazolo[3,2-a]pyrimidin-5-one, or
a pharmaceutically acceptable salt thereof.

43. The compound of claim 1 selected from:
7-[(E)-2-(2-Cyclopropylmethoxy-3-methoxyphenyl)-1-ethenyl]-6-(4-methoxyphenyl)-5H-[1,3]thiazolo[3,2-a]pyrimidin-5-one,
7-[(E)-2-(2-Cyclopropylmethoxy-3-methoxyphenyl)-1-ethenyl]-6-(4-ethoxyphenyl)-5H-[1,3]thiazolo[3,2-a]pyrimidin-5-one, 7-[(E)-2-(2-Cyclopropylmethoxy-3-methoxyphenyl)-1-ethenyl]-6-(4-(2,2,2-trifluoro-ethoxy)phenyl]-5H-[1,3]thiazolo[3,2-a]pyrimidin-5-one, 3-4-{7-[(E)-2-(2-Cyclopropylmethoxy-3-methoxyphenyl)-1-ethenyl]-5H-[1,3]thiazolo-[3,2-a]pyrimidin-6-yl}phenoxy)propyl cyanide, 7-[(E)-2-(2-Cyclopropylmethoxy-3-methoxyphenyl)-1-ethenyl]-6-(4-cyclopropyl-methoxyphenyl]-5H-[1,3]thiazolo[3,2-a]pyrimidin-5-one, and 7-[(E)-2-{2-(4-Fluorobutoxy)-3-methoxyphenyl}-1-ethenyl]-6-[4-(trifluoromethoxy)-phenyl]-5H-[1,3]thiazolo[3,2-a]pyrimidin-5-one, or a pharmaceutically acceptable salt thereof.

44. The compound of claim 1 selected from:

7-{(E)-(2,3-Dihydroxy)phenyl]-1-ethenyl]-6-(4-trifluoromethoxy-phenyl)-5H-[1,3]thiazolo[3,2-a]pyrimidin-5-one, 7-{(E)-(2-Cyclopropylmethoxy-3-hydroxy)phenyl]-1-ethenyl]-6-(4-trifluoro-methoxyphenyl)-5H-[1,3]thiazolo[3,2-a]pyrimidin-5-one, 7-{(E)-2-[2-(Cyclopropylmethoxy)-3-ethoxyphenyl]-1-ethenyl]-6-(4-trifluoromethoxy-phenyl)-5H-[1,3]thiazolo[3,2-a]pyrimidin-5-one, 7-{(E)-2-[2-(Cyclopropylmethoxy)-3-(2-ethoxyethoxy)phenyl]-1-ethenyl]-6-(4-trifluoro-methoxyphenyl)-5H-[1,3]thiazolo[3,2-a]pyrimidin-5-one, 7-{(E)-2-[2-(Cyclopropylmethoxy)-3-(cyclopropylmethoxy)phenyl]-1-ethenyl]-6-(4-trifluoromethoxyphenyl)-5H-[1,3]thiazolo[3,2-a]pyrimidin-5-one, and 7-{(E)-2-[2-(Cyclopropylmethoxy)-3-(3-cyanopropoxy)phenyl]-1-ethenyl]-6-(4-trifluoromethoxyphenyl)-5H-[1,3]thiazolo[3,2-a]pyrimidin-5-one, or a pharmaceutically acceptable salt thereof.

45. The compound of claim 1 selected from:

7-{(E)-2-[2-(Cyclopropylmethoxy)-3-propoxyphenyl]-1-ethenyl]-6-(4-trifluoromethoxy-phenyl)-5H-[1,3]thiazolo[3,2-a]pyrimidin-5-one, 7-[(E)-2-{2-(Cyclopentyloxy-3-methoxyphenyl}-1-ethenyl]-6-[4-(trifluoromethoxy)-phenyl]-5H-[1,3]thiazolo[3,2-a]pyrimidin-5-one, 7-[(E)-2-(2-Hydroxy-3-methoxyphenyl)-1-ethenyl]-6-[4-(trifluoromethoxy)phenyl]-5H-[1,3]thiazolo[3,2-a]pyrimidin-5-one, 7-[(E)-2-(2-Cyclohexylmethoxy-3-methoxyphenyl)-1-ethenyl]-6-[4-(trifluoromethoxy)-phenyl]-5H-[1,3]thiazolo[3,2-a]pyrimidin-5-one, 7-[(E)-2-(2-Cyclohexyloxy-3-methoxyphenyl)-1-ethenyl]-6-[4-(trifluoromethoxy)-phenyl]-5H-[1,3]thiazolo[3,2-a]pyrimidin-5-one, and 7-[(E)-2-{3-Methoxy-2-(2-methoxyethoxy)phenyl}-1-ethenyl]-6-[4-(trifluoromethoxy)-phenyl]-5H-[1,3]thiazolo[3,2-a]pyrimidin-5-one, or a pharmaceutically acceptable salt thereof.

46. The compound of claim 1 selected from:

7-[(E)-2-{(3-Cyanopropoxy)-3-methoxy}phenylvinyl]-6-[4-(trifluoromethoxy)-phenyl]-5H-[1,3]thiazolo[3,2-a]pyrimidin-5-one, 7-[(E)-2-(2-Cyclopropylmethoxy-3-methoxyphenyl)-1-ethenyl]-3-methyl-6-[4-(trifluoro-methoxy)phenyl]-5H-[1,3]thiazolo[3,2-a]pyrimidin-5-one, 7-[(E)-2-(2-Cyclopropylmethoxy-3-methoxyphenyl)-1-ethenyl]-2,3-dimethyl-6-[4-(trifluoromethoxy)phenyl]-5H-[1,3]thiazolo[3,2-a]pyrimidin-5-one, 2-Chloro-7-[(E)-2-(2-(2,2-dimethylpropoxy)-3-methoxyphenyl)vinyl]-6-[4-(trifluoro-methoxy)phenyl]-5H-[1,3]thiazolo[3,2-a]pyrimidin-5-one, 2-Chloro-6-[4-(dimethylamino)phenyl]-7-[(E)-2-(2-(2,2-dimethylpropoxy)-3-methoxy-phenyl)vinyl]-5H-[1,3]thiazolo[3,2-a]pyrimidin-5-one, and 4-{2-Chloro-7-[(E)-2-(2-(2,2-dimethylpropoxy)-3-methoxyphenyl)vinyl]-5-oxo-5H-[1,3]thiazolo[3,2-a]pyrimidin-6-yl}benzonitrile, or a pharmaceutically acceptable salt thereof.

47. The compound of claim 1 selected from:

2-Chloro-6-[4-(dimethylamino)phenyl]-7-[(E)-2-(2-isobutoxy-3-methoxyphenyl)vinyl]-5H-[1,3]thiazolo[3,2-a]pyrimidin-5-one, 4-{7-[(E)-2-(3-Methoxy-2-neopentyloxyphenyl)-1-ethenyl]-5-oxo-3-(trifluoromethyl)-5H-[1,3]thiazolo[3,2-a]pyrimidin-6-yl}benzonitrile, 4-(2-{(E)-2-[2-(3-Cyanopropoxy)-3-methoxyphenyl]-1-ethenyl]-4-oxo-4H-benzo[4,5]-[1,3]thiazolo-[3,2]pyrimidin-3-yl)benzonitrile, 4-(2-{(E)-2-[3-Methoxy-2-(methoxyethoxy)phenyl]-1-ethenyl]-4-oxo-4H-benzo[4,5]-[1,3]thiazolo-[3,2]pyrimidin-3-yl)benzonitrile, 4-{2-[(E)-2-[2-(2-Ethoxyethoxy)-3-methoxy]phenyl]-1-ethenyl]-4-oxo-4H-benzo[4,5]-[1,3]thiazolo-[3,2]pyrimidin-3-yl)benzonitrile, and 4-{2-[(E)-2-[2-Cyclopropylmethoxy-3-methoxy]phenyl]-1-ethenyl]-4-oxo-4H-benzo[4,5]-[1,3]thiazolo-[3,2]pyrimidin-3-yl)benzonitrile, or a pharmaceutically acceptable salt thereof.

48. The compound of claim 1 selected from:

4-{2-[(E)-2-[2-Butoxy-3-methoxy]phenyl]-1-ethenyl]-4-oxo-4H-benzo[4,5]-[1,3]thiazolo-[3,2]pyrimidin-3-yl)benzonitrile, 4-{2-[(E)-2-[2-(3-Methylbutoxy-3-methoxy]phenyl]-1-ethenyl]-4-oxo-4H-benzo[4,5]-[1,3]thiazolo-[3,2]pyrimidin-3-yl)benzonitrile, 4-{2-[(E)-2-[2-Cyclobutylmethoxy-3-methoxy]phenyl]-1-ethenyl]-4-oxo-4H-benzo[4,5]-[1,3]thiazolo-[3,2]pyrimidin-3-yl)benzonitrile, 4-{2-[(E)-2-[3-Methoxy-2-pyridin-2-ylmethoxy]phenyl]-1-ethenyl]-4-oxo-4H-benzo[4,5]-[1,3]thiazolo-[3,2]pyrimidin-3-yl)benzonitrile, 2-{(E)-2-[(2-Cyclopropylmethoxy)-3-methoxy]phenyl]-1-ethenyl]-3-(4-trifluoromethyl-phenyl)-4H-benzo[4,5][1,3]thiazolo-[3,2-a]pyrimidin-4-one, and 2-{(E)-2-[(2-Methoxyethoxy)-3-methoxyphenyl]-1-ethenyl]-3-(4-trifluoromethyl-phenyl)-4H-benzo[4,5][1,3]thiazolo-[3,2-a]pyrimidin-4-one, or a pharmaceutically acceptable salt thereof.

49. The compound of claim 1 selected from:

2-{(E)-2-[(2-Ethoxyethoxy)-3-methoxyphenyl]-1-ethenyl]-3-(4-trifluoromethyl-phenyl)-4H-benzo[4,5][1,3]thiazolo-[3,2-a]pyrimidin-4-one, 2-{(E)-2-[(3-Cyanopropoxy-3-methoxy)phenyl]-1-ethenyl]-3-(4-trifluoromethyl-phenyl)-4H-benzo[4,5][1,3]thiazolo-[3,2-a]pyrimidin-4-one, 2-{(E)-2-[2-Cyclopropylmethoxy-3-methoxyphenyl]-1-ethenyl]-3-(4-trifluoromethoxy-phenyl)-4H-benzo[4,5][1,3]thiazolo-[3,2-a]pyrimidin-4-one, 2-{(E)-2-[3-Methoxy-2-(2-methoxyethoxy)phenyl]-1-ethenyl]-3-(4-trifluoromethoxy-phenyl)-4H-benzo[4,5][1,3]thiazolo-[3,2-a]pyrimidin-4-one, 2-{(E)-2-[(2-Ethoxyethoxy)-3-methoxyphenyl]-1-ethenyl]-3-(4-trifluoromethoxy-phenyl)-4H-benzo[4,5][1,3]thiazolo-[3,2-a]pyrimidin-4-one, and 7-[(E)-2-(4-Chlorophenyl)vinyl]-6-phenyl-5H-[1,3]thiazolo[3,2-a]pyrimidin-5-one, or a pharmaceutically acceptable salt thereof.

50. The compound of claim 1 selected from:

7-[(E)-2-(2-Cyclopropylmethoxy)-3-methoxyphenyl)-1-ethenyl]-6-(6-fluoro-3-pyridyl)-5H-[1,3]thiazolo[3,2-a]pyrimidin-5-one, 4-{5-oxo-7-[(E)-2-(3-pyridyl)-1-ethenyl]-5H-[1,3]thiazolo[3,2-a]pyrimidin-6-yl}-benzonitrile, 7-[(E)-2-(2-Cyclopropylmethoxy)-1-ethenyl]-6-[4-(trifluoromethyl)phenyl]-5H-[1,3]-thiazolo[3,2-a]pyrimidin-5-one, 7-[(E)-2-(3-Cyclopropylmethoxy-4-methoxyphenyl)-1-ethenyl]-6-[4-(trifluoromethyl)-phenyl]-5H-[1,3]thiazolo[3,2-a]pyrimidin-5-one, 7-[(E)-2-(4-Cyclopropylmethoxy-3-methoxyphenyl)-1-ethenyl]-6-[4-(trifluoromethyl)-phenyl]-5H-[1,3]thiazolo[3,2-a]pyrimidin-5-one, 7-[(E)-2-Pyridin-3-ylvinyl]-6-[4-(trifluoromethyl)phenyl]-5H-[1,3]thiazolo[3,2-a]pyrimidin-5-one, 7-[(E)-2-(2-Cyclopropylmethoxy-3-fluorophenyl)-1-ethenyl]-6-[4-(trifluoromethoxy)-phenyl]-5H-[1,3]thiazolo[3,2-a]pyrimidin-5-one, and 2-[(E)-2-(2-Cyclopropylmethoxy-3-methoxyphenyl)vinyl]-3-(4-trifluoromethoxyphenyl)-10-methylpyrimido[1,2-a]benzimidazol-4(10H)-one or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 8,119,647 B2 |
| APPLICATION NO. | : 12/421145 |
| DATED | : February 21, 2012 |
| INVENTOR(S) | : V. S. Prasada Rao Lingam et al. |

It is certified that error appears in the above-identified patent and that said Letters Patent is hereby corrected as shown below:

Column 7
Line 7, replace "R6" with --R6a--;
Line 31, delete "(Compound 1)".

Column 8
Line 50, before 7 delete "{";
Line 53, before 7 delete "{";
Line 56, before 7 delete "{".

Column 9
Line 18, delete "(Compound 42)";
Line 59, before 7 delete "4-{".

Column 10
Line 1, replace "7-{(E)-[(2,3-Dihydroxy)phenyl}-1-ethenyl]" with
--7-{(E)-2-[(2,3-Dihydroxy)phenyl]-1-ethenyl}--;
Line 4, replace "7-{(E)-[(2-Cyclopropylmethoxy-3-hydroxy)phenyl]-1-ethenyl}" with
--7-{(E)-2-[(2-Cyclopropylmethoxy-3-hydroxy)phenyl]-1-ethenyl}--;
Line 35, before 7 delete "4-{";
Line 35, replace "2-2-trifluoromethyl" with --2-(2-trifluoromethyl--;
Line 47, before 7 delete "4-{".

Column 11
Line 58, replace "of compounds 1 – 98" with --of the above compounds--.

Column 12
Line 20, after defined delete "ly".

Signed and Sealed this
Sixth Day of November, 2012

David J. Kappos
*Director of the United States Patent and Trademark Office*

CERTIFICATE OF CORRECTION (continued)
U.S. Pat. No. 8,119,647 B2

Column 17
Scheme 1, replace "CH3COCH2 CO2R1" with --CH3COCH2 CO2R'--.

Column 22
Line 29, replace "formula 5(b)" with --formula 5(a)--.

Column 23
Scheme 5, replace "5(a)" with --5(b)--.

Column 24
Scheme 5, replace "5(a)" with --5(b)--.

Column 29
Line 27, replace "5(a)" with --5(b)--.

Column 54
Line 27, before 7 delete "{";
Line 43, before 7 delete "{";
Line 62, before 7 delete "{".

Column 63
Line 9, replace "Examples 51-69" with --Examples 51-58, 67-68 and 71-74--;
Line 11, after Example 24, add --and other compounds were prepared by the procedure as described in scheme 7--.

Column 66
Line 62, before 7 delete "4-".

Column 67
Lines 52-54, replace "7-{(E)-[(2,3-Dihydroxy)phenyl}-1-ethenyl]-6-(4-trifluoromethoxy-phenyl)-5H-[1,3]thiazolo [3,2-a]pyrimidin-5-one" with --7-{(E)-2-[(2,3-Dihydroxy)phenyl]-1-ethenyl}-6-(4-trifluoromethoxy-phenyl)-5H-[1,3] thiazolo[3,2-a]pyrimidin-5-one--.

Column 68
Lines 3-5, replace "7-{(E)-[(2-Cyclopropylmethoxy-3-hydroxy)phenyl]-1-ethenyl}-6-(4-trifluoro-methoxyphenyl)-5H-[1,3]thiazolo[3,2-a]pyrimidin-5-one" with --7-{(E)-2-[(2-Cyclopropylmethoxy-3-hydroxy) phenyl]-1-ethenyl}-6-(4-trifluoro-methoxyphenyl)-5H-[1,3]thiazolo[3,2-a]pyrimidin-5-one--.

Column 83
Line 15, replace "Table 6" with --Table 7--;
Line 20, replace "Table 6" with --Table 7--;
Line 27, replace "Table 6:" with --Table 7--.

Column 85
In claim 1, line 48, delete "'p' is an integer ranging from 0 to 2, inclusive;".

Column 86
In claim 2, lines 28-29, delete "at each occurrence, Rb is selected from hydrogen, substituted or unsubstituted alkyl, or arylalkyl;";
In claim 2, line 32, delete "'p' is an integer ranging from 0 to 2, inclusive;".

Column 87
In claim 4, lines 25-29, delete "at each occurrence, R7, is independently selected from halogen, nitro, cyano, substituted or unsubstituted alkyl, alkenyl, alkynyl, cycloalkyl, aryl, heteroaryl, heterocyclic group, -NR4R5, -S (O)pNR4R5, or -S(O)pR4;";
In claim 4, line 39, replace "'r' is an integer ranging from 0 to 4;" with --'r' is 0;--.

Column 88
Line 39, delete claim 31 and substitute the following;
--31. 7-{(E)- 2-[( (2-Cyclopropylmethoxy-3-hydroxy)phenyl]-1-ethenyl}-6-(4-trifluoro-methoxyphenyl)-5H-[1,3] thiazolo[3,2-a]pyrimidin-5-one, or a pharmaceutically acceptable salt thereof.--;
Line 43, delete claim 31 and substitute the following:
--32. 7-{(E)- 2-[(2,3-Dihydroxy)phenyl]-1-ethenyl}-6-(4-trifluoromethoxy-phenyl)-5H-[1,3]thiazolo[3,2-a] pyrimidin-5-one, or a pharmaceutically acceptable salt thereof.--.

Column 89
In claim 38, line 35, before 7 delete "{";
In claim 38, line 38, before 7 delete "{".

Column 90
In claim 41, line 22, before 7 delete "{".